(12) United States Patent
Graham et al.

(10) Patent No.: US 6,287,805 B1
(45) Date of Patent: Sep. 11, 2001

(54) NUCLEIC ACID MOLECULES OF THE PROTEIN-COUPLED HEPTAHELICAL RECEPTOR SUPERFAMILY AND USES THEREFOR

(75) Inventors: Gerard J. Graham, Shawlands Glasgow; Robert J. Benjamin Nibbs, Glasgow, both of (GB); Jose-Angel Gonzalo, Cambridge; Jose-Carlos Gutierrez-Ramos, Swampscott, both of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/045,583

(22) Filed: Mar. 20, 1998

(51) Int. Cl.[7] ............................ C12P 21/04; C12N 15/00; C12N 15/09; C12N 15/63; C07H 21/04
(52) U.S. Cl. ................... 435/69.1; 435/325; 435/252.3; 435/254.11; 435/320.1; 536/23.5
(58) Field of Search ................................. 435/69.1, 325, 435/252.3, 254.11, 320.1; 536/23.5

(56) References Cited

U.S. PATENT DOCUMENTS 5,026,828 * 6/1991 Yamazaki ............................. 530/414
5,440,021   8/1995 Chuntharapai et al. .......... 530/388.22

FOREIGN PATENT DOCUMENTS

| WO 9217497 | 10/1992 | (WO) . |
| WO 9428931 | 12/1994 | (WO) . |
| WO 9519436 | 7/1995 | (WO) . |
| WO 9525126 | 9/1995 | (WO) . |
| WO 9623068 | 8/1996 | (WO) . |
| WO 9639434 | 12/1996 | (WO) . |
| WO 9639437 | 12/1996 | (WO) . |
| WO 9722698 | 6/1997 | (WO) . |

OTHER PUBLICATIONS

Bonini, J.A. and Steiner, D.F. "Molecular Cloning and Expression of a Novel Rat CC–Chemokine Receptor (rCCR10rR) that Binds MCP–1 and MIP–1beta with High Affinity" *DNA Cell Biol.* 16(9):1023–1030 (1997).

Bonini, J.A. et al. "Cloning, Expression, and Chromosomal Mapping of a Novel Human CC–Chemokine Receptor (CCR10) That Displays High–Affinity Binding for MCP–1 and MCP–3" *DNA Cell Biol.* 16(10):1249–1256 (1997).

Robert, J.B. Nibbs et al. "Cloning and Characterization of a Novel Promiscuous Human β–Chemokine Receptor D6" *The Journal of Biological Chemistry* 272(51):32078–32083 (1997).

Robert, J.B. Nibbs et al. "Cloning and Characterization of a Novel Murine β Chemokine Receptor, D6" *The Journal of Biological Chemistry* 272(19):12495–12504 (1997).

Damaj BB, et al. Physical association of Gi2alpha with interleukin–8 receptors. *J Biol Chem.* May 31, 1996;271(22):12783–9.

Fields S, et al. The two–hybrid system: an assay for protein–protein interactions. *Trends Genet.* Aug. 1994;10(8):286–92.

George DE et al. Current Methods or Sequence Comparison and Analysis in Macromolecular Sequencing and Synthesis—Selected Methods and Applications. Schlesinger DH (Alan R. Liss Inc., New York) pp. 121–149, 1988.*

Cunningham BC and Wells JA. High Resolution Epitope Mapping or MGH–Receptor Interactions by Alanine–Scanning Ultragenesis. Science, vol. 244 pp. 1081–1085, 1989.*

Feng L et al., "Interleukin–1x Stimulates KC Synthesis in Rat Megangial Cells Glucocorticoids Inhibit KC Induction by IL–1" American J. Physiology 266 #5 Part 2 pp. F713–F722, 1994.*

Combadiere C, et al. "Cloning and functional expression of a human eosinophil CC chemokine receptor". *J Biol Chem.* Jul. 14, 1995;270(28):16491–4.

* cited by examiner

Primary Examiner—Gary L. Kunz
Assistant Examiner—Robert S. Landsman
(74) *Attorney, Agent, or Firm*—Lahive & Cockfield, LLP; Amy E. Mandragouras; Maria C. Laccotripe

(57) ABSTRACT

Novel D6 polypeptides, proteins, and nucleic acid molecules are disclosed. In addition to isolated, full-length D6 proteins, the invention further provides isolated D6 fusion proteins, antigenic peptides and anti-D6 antibodies. The invention also provides D6 nucleic acid molecules, recombinant expression vectors containing nucleic acid molecules of the invention, host cells into which the expression vectors have been introduced and non-human transgenic animals in which a D6 gene has been introduced or disrupted. Diagnostic, screening and therapeutic methods utilizing compositions of the invention are also provided.

25 Claims, 7 Drawing Sheets

```
GGATCCTCCA AC ATG GCC GCC ACT GCC TCT CCG CAG CCA CTC GCC ACT         48
              Met Ala Ala Thr Ala Ser Pro Gln Pro Leu Ala Thr
               1               5                      10

GAG GAT GCC GAT TCT GAG AAT AGC AGC TTC TAT TAC TAT GAC TAC CTG       96
Glu Asp Ala Asp Ser Glu Asn Ser Ser Phe Tyr Tyr Tyr Asp Tyr Leu
            15                  20                  25

GAT GAA GTG GCC TTC ATG CTC TGC AGG AAG GAT GCA GTG GTG TCC TTT      144
Asp Glu Val Ala Phe Met Leu Cys Arg Lys Asp Ala Val Val Ser Phe
        30                  35                  40

GGC AAA GTC TTC CTC CCA GTC TTC TAT AGC CTG ATT TTT GTG TTG GGC      192
Gly Lys Val Phe Leu Pro Val Phe Tyr Ser Leu Ile Phe Val Leu Gly
 45                 50                  55                  60

CTC AGC GGG AAC CTC CTT CTT CTC ATG GTC TTG CTC CGT TAC GTG CCT      240
Leu Ser Gly Asn Leu Leu Leu Leu Met Val Leu Leu Arg Tyr Val Pro
                65                  70                  75

CGC AGG CGG ATG GTT GAG ATC TAT CTG CTG AAT CTG GCC ATC TCC AAC      288
Arg Arg Arg Met Val Glu Ile Tyr Leu Leu Asn Leu Ala Ile Ser Asn
            80                  85                  90

CTT CTG TTT CTG GTG ACA CTG CCC TTC TGG GGC ATC TCC GTG GCC TGG      336
Leu Leu Phe Leu Val Thr Leu Pro Phe Trp Gly Ile Ser Val Ala Trp
        95                  100                 105

CAT TGG GTC TTC GGG AGT TTC TTG TGC AAG ATG GTG AGC ACT CTT TAT      384
His Trp Val Phe Gly Ser Phe Leu Cys Lys Met Val Ser Thr Leu Tyr
    110                 115                 120

ACT ATT AAC TTT TAC AGT GGC ATC TTT TTC ATT AGC TGC ATG AGC CTG      432
Thr Ile Asn Phe Tyr Ser Gly Ile Phe Phe Ile Ser Cys Met Ser Leu
125                 130                 135                 140

GAC AAG TAC CTG GAG ATC GTT CAT GCT CAG CCC TAC CAC AGG CTG AGG      480
Asp Lys Tyr Leu Glu Ile Val His Ala Gln Pro Tyr His Arg Leu Arg
                145                 150                 155

ACC CGG GCC AAG AGC CTG CTC CTT GCT ACC ATA GTA TGG GCT GTG TCC      528
Thr Arg Ala Lys Ser Leu Leu Leu Ala Thr Ile Val Trp Ala Val Ser
            160                 165                 170

CTG GCC GTC TCC ATC CCT GAT ATG GTC TTT GTA CAG ACA CAT GAA AAT      576
Leu Ala Val Ser Ile Pro Asp Met Val Phe Val Gln Thr His Glu Asn
        175                 180                 185

CCC AAG GGT GTG TGG AAC TGC CAC GCA GAT TTC GGC GGG CAT GGG ACC      624
Pro Lys Gly Val Trp Asn Cys His Ala Asp Phe Gly Gly His Gly Thr
    190                 195                 200

ATT TGG AAG CTC TTC CTC CGC TTC CAG CAG AAC CTC CTA GGG TTT CTC      672
Ile Trp Lys Leu Phe Leu Arg Phe Gln Gln Asn Leu Leu Gly Phe Leu
205                 210                 215                 220
```

Fig. 1

```
CTT CCA CTC CTT GCC ATG ATC TTC TTC TAC TCC CGT ATT GGT TGT GTC    720
Leu Pro Leu Leu Ala Met Ile Phe Phe Tyr Ser Arg Ile Gly Cys Val
                225                 230                 235

TTG GTG AGG CTG AGG CCC GCA GGC CAG GGC CGG GCT TTA AAA ATA GCT    768
Leu Val Arg Leu Arg Pro Ala Gly Gln Gly Arg Ala Leu Lys Ile Ala
            240                 245                 250

GCA GCC TTG GTG GTG GCC TTC TTC GTG CTA TGG TTC CCA TAC AAT CTC    816
Ala Ala Leu Val Val Ala Phe Phe Val Leu Trp Phe Pro Tyr Asn Leu
                255                 260                 265

ACC TTG TTT CTG CAT ACG CTG TTG GAC CTG CAA GTA TTC GGG AAC TGT    864
Thr Leu Phe Leu His Thr Leu Leu Asp Leu Gln Val Phe Gly Asn Cys
        270                 275                 280

GAG GTC AGC CAG CAT CTA GAC TAC GCA CTC CAG GTA ACA GAG AGC ATC    912
Glu Val Ser Gln His Leu Asp Tyr Ala Leu Gln Val Thr Glu Ser Ile
285                 290                 295                 300

GCC TTC CTT CAC TGC TGC TTT TCC CCC ATC CTG TAT GCC TTC TCC AGT    960
Ala Phe Leu His Cys Cys Phe Ser Pro Ile Leu Tyr Ala Phe Ser Ser
                305                 310                 315

CAC CGC TTC CGC CAG TAC CTG AAG GCT TTC CTG GCT GCC GTG CTT GGA    1008
His Arg Phe Arg Gln Tyr Leu Lys Ala Phe Leu Ala Ala Val Leu Gly
                320                 325                 330

TGG CAC CTG GCA CCT GGC ACT GCC CAG GCC TCA TTA TCC AGC TGT TCT    1056
Trp His Leu Ala Pro Gly Thr Ala Gln Ala Ser Leu Ser Ser Cys Ser
                335                 340                 345

GAG AGC AGC ATA CTT ACT GCC CAA GAG GAA ATG ACT GGC ATG AAT GAC    1104
Glu Ser Ser Ile Leu Thr Ala Gln Glu Glu Met Thr Gly Met Asn Asp
        350                 355                 360

CTT GGA GAG AGG CAG TCT GAG AAC TAC CCT AAC AAG GAG GAT GTG GGG    1152
Leu Gly Glu Arg Gln Ser Glu Asn Tyr Pro Asn Lys Glu Asp Val Gly
365                 370                 375                 380

AAT AAA TCA GCC TGAGTGACCG CGGCCGC                                 1181
Asn Lys Ser Ala
```

Fig. 1 (continued)

| | |
|---|---:|
| CAAAAAATTG GGAAGGGGGG GTTTCGGGAA AAAGGGGGGG GGATTTGGGG AAGGGGGGAA | 60 |
| AGCAAAGCCG CCAGGGGGTG GGGGAAAGGG GAGCAGGGGA ACCAACAACC AGCATTCGGC | 120 |
| AGTTAACCAG TTAAGCCCAG TTTTTTAGCT GGGGGCAGAG ACCAGATCCT GCAAGCATCA | 180 |

```
GAGCTCGAGG AC ATG CCC ACC GTT GCT TCC CCA CTG CCT CTC ACC ACC        228
           Met Pro Thr Val Ala Ser Pro Leu Pro Leu Thr Thr
            1               5                       10

GTC GGT TCC GAG AAC AGC AGC TCC ATC TAC GAC TAC GAC TAC TTA GAT      276
Val Gly Ser Glu Asn Ser Ser Ser Ile Tyr Asp Tyr Asp Tyr Leu Asp
             15                  20                  25

GAT ATG ACC ATC TTG GTT TGC AGG AAG GAC GAG GTC CTG TCC TTT GGA      324
Asp Met Thr Ile Leu Val Cys Arg Lys Asp Glu Val Leu Ser Phe Gly
        30                  35                  40

AGA GTC TTT CTG CCG GTC GTC TAC AGC CTG ATC TTC GTG CTG GGC TTG      372
Arg Val Phe Leu Pro Val Val Tyr Ser Leu Ile Phe Val Leu Gly Leu
45                  50                  55                  60

GCT GGA AAC CTC CTC CTC CTG GTG GTG TTG CTC CAC TCT GCA CCT CGA      420
Ala Gly Asn Leu Leu Leu Leu Val Val Leu Leu His Ser Ala Pro Arg
                65                  70                  75

AGA CGG ACG ATG GAG CTT TAC CTG CTG AAC CTG GCC GTC TCC AAC CTC      468
Arg Arg Thr Met Glu Leu Tyr Leu Leu Asn Leu Ala Val Ser Asn Leu
            80                  85                  90

TTG TTT GTA GTG ACT ATG CCC TTC TGG GCC ATC TCT GTG GCC TGG CAT      516
Leu Phe Val Val Thr Met Pro Phe Trp Ala Ile Ser Val Ala Trp His
            95                  100                 105

TGG GTT TTT GGT AGT TTC CTG TGC AAG GTG ATA AGC ACT CTC TAC TCT      564
Trp Val Phe Gly Ser Phe Leu Cys Lys Val Ile Ser Thr Leu Tyr Ser
    110                 115                 120

ATT AAC TTT TAC TGT GGT ATC TTC TTC ATC ACC TGC ATG AGC CTG GAC      612
Ile Asn Phe Tyr Cys Gly Ile Phe Phe Ile Thr Cys Met Ser Leu Asp
125                 130                 135                 140

AAA TAC CTG GAG ATT GTC CAC GCT CAG CCT CTC CAC AGA CCG AAG GCC      660
Lys Tyr Leu Glu Ile Val His Ala Gln Pro Leu His Arg Pro Lys Ala
                145                 150                 155

CAG TTC AGG AAC CTG CTT CTC ATT GTC ATG GTG TGG ATC ACA TCC CTG      708
Gln Phe Arg Asn Leu Leu Leu Ile Val Met Val Trp Ile Thr Ser Leu
            160                 165                 170
```

Fig. 2

```
GCC ATC TCT GTC CCA GAA ATG GTC TTT GTG CAG ATC CAC CAG ACC TTA    756
Ala Ile Ser Val Pro Glu Met Val Phe Val Gln Ile His Gln Thr Leu
        175             180             185

GAT GGT GTG TGG CAC TGC TAT GCG GAT TTT GGC GGA CAT GCG ACC ATT    804
Asp Gly Val Trp His Cys Tyr Ala Asp Phe Gly Gly His Ala Thr Ile
        190             195             200

TGG AAG CTG TAC CTG CGC TTC CAG CTG AAC CTT CTG GGG TTT CTC CTC    852
Trp Lys Leu Tyr Leu Arg Phe Gln Leu Asn Leu Leu Gly Phe Leu Leu
205             210             215             220

CCA CTC TTG GCC ATG ATC TTC TTT TAC TCC CGC ATC GGT TGC GTT CTG    900
Pro Leu Leu Ala Met Ile Phe Phe Tyr Ser Arg Ile Gly Cys Val Leu
                225             230             235

GTC AGG CTG AGG CCG CCA GGC CAG GGC CGG GCT CTG AGG ATG GCC GCG    948
Val Arg Leu Arg Pro Pro Gly Gln Gly Arg Ala Leu Arg Met Ala Ala
        240             245             250

GCC CTG GTG ATA GTT TTC TTC ATG CTG TGG TTC CCA TAT TAC CTC ACC    996
Ala Leu Val Ile Val Phe Phe Met Leu Trp Phe Pro Tyr Tyr Leu Thr
        255             260             265

TTG TTT CTG CAC TCG TTG CTG GAC CTG CAT GTC TTT GGG AAC TGT GAG   1044
Leu Phe Leu His Ser Leu Leu Asp Leu His Val Phe Gly Asn Cys Glu
        270             275             280

ATC AGC CAC CGT CTG GAC TAT ACG TTG CAG GTG ACA GAG AGC CTG GCC   1092
Ile Ser His Arg Leu Asp Tyr Thr Leu Gln Val Thr Glu Ser Leu Ala
285             290             295             300

TTC TCC CAC TGC TGC TTC ACC CCG GTC CTC TAC GCC TTC TGC AGT CAC   1140
Phe Ser His Cys Cys Phe Thr Pro Val Leu Tyr Ala Phe Cys Ser His
                305             310             315

CGC TTC CGC CGG TAC CTG AAG GCA TTT CTG TCT GTG ATG TTG AGA TGG   1188
Arg Phe Arg Arg Tyr Leu Lys Ala Phe Leu Ser Val Met Leu Arg Trp
        320             325             330

CAC CAG GCA CCT GGC ACC CCT TCC TCT AAC CAT TCT GAG AGC AGC AGG   1236
His Gln Ala Pro Gly Thr Pro Ser Ser Asn His Ser Glu Ser Ser Arg
        335             340             345

GTT ACT GCC CAG GAA GAC GTG GTC AGC ATG AAT GAC CTT GGG GAG AGG   1284
Val Thr Ala Gln Glu Asp Val Val Ser Met Asn Asp Leu Gly Glu Arg
        350             355             360

CAG TCT GAG GAC TCC CTT AAC AAG GGG GAG ATG GGG AAT ACT            1326
Gln Ser Glu Asp Ser Leu Asn Lys Gly Glu Met Gly Asn Thr
365             370             375

TAGGCCCGAG TGATCAGCCA CGGTCTGGGA ACAGCACTGC TCTCTCTGAG GGACAGCGTG  1386

ACTGTGCTGC TCGCCCCAGT GGTTCCCAAC CACCAGCAGG CCTTACTCAT TACTGTCTCT  1446
```

Fig. 2 (continued)

```
TCCTCCTTCT GCTTCCTGGA CCCCATCCTC TCTGCTGAAC CACTTCAGCT CTTCACTGAT    1506

CTCCCTCCAC TTCCACCCCA GCGCTTCTGT GGCTTCCTGG CCCTCAGCAG CCAATGAGGT    1566

CACTCCACTC TTAGCCTTCA GACCTTCAAG GGCCATGTGA TCATTGATGT GACTTTATTT    1626

CCACCGTACT CCCTCCTGGT CTCTGGGTTC AGGGCACA                            1664
```

Fig. 2 (continued)

```
hCCR6   ----------  ---MSGESNN  FSDVFDSSED  YFVSVNTSYY  SVDSEMLLCS  LQEVRQFSRL  FVPIAYSLIC
hCCR7   MDLGKPMKSV  LVVALLVIFQ  VCLCQDEVTD  DYIGDNTTVD  YTLFES.LCS  KKDVRNFKAW  FLPIMYSIIC
hD6     ----------  --MAATASP   QPLATEDADSE N.SSFYYYDY  LDEVAFMLCR  KDAVVSFGKV  FLPVFYSLIF
mD6     ----------  --MPTVASP   LPLTTVG..SE NSSSIYDYDY  LDDMTILVCR  KDEVLSFGRV  FLPVVYSLIF
hCCR2a  ----------  -------MLS  TSRSRFIRNT  NESGEEVTTF  FDYDYGAPCH  KFDVKQIGAQ  LLPPLYSLVF
hCCR2b  ----------  -------MLS  TSRSRFIRNT  NESGEEVTTF  FDYDYGAPCH  KFDVKQIGAQ  LLPPLYSLVF
hCCR5   ----------  ----------  ---------M  DYQVSSPIYD  INYYTSEPCQ  KINVKQIAAR  LLPPLYSLVF
hCCR1   ----------  ----------  -----METPN  TTEDYDTTTE  FDYGDATPCQ  KVNERAFGAQ  LLPPLYSLVF
hCCR3   ----------  ----------  ----MTTSLD  TVETFGTTSY  YD.DVGLLCE  KADTRALMAQ  FVPPLYSLVF
hCCR4   ----------  ----------  MNPTDIADTT  LDESIYSNYY  LYESIPKPCT  KEGIKAFGEL  FLPPLYSLVF
hCCR8   ----------  ----------  ----MDYTLD  LSVTTVTDYY  YPDIFSSPCD  AELIQTNGKL  LLAVFYCLLF
                                                        C          -  ------I---
                                                        # hCCR6   VFALLGNILV  VITFAFNKKA  RSMTDVYLVN  MAIADILFVL  TLPFWAVSHA  TGAWVFSNAT  CKLLKGIYAI
hCCR7   FVGLLGNGLV  VLTYIYFKRL  KTMTDTYLLN  LAVADILFLL  TLPFWAYS.A  AKSWVFGVHF  CKLIFAIYKM
hD6     VLGLSGNLLL  LMVLLRYVPR  RRMVEIYLLN  LAISNLLFLV  TLPFWG.ISV  AWHWVFGSFL  CKMVSTLYTI
mD6     VLGLAGNLLL  LVVLLHSAPR  RRTHELYLLN  LAVSNLLFVV  THPFWA.ISV  AWHWVFGSFL  CKVISTLYSI
hCCR2a  IFGFVGNMLV  VLILINCKKL  KCLTDIYLLN  LAISDLLFLI  TLPLWAHSA.  ANEWVFGNAM  CKLFTGLYHI
hCCR2b  IFGFVGNMLV  VLILINCKKL  KCLVDIYLLN  LAISDLLFLI  TLPLWAHSA.  ANEWVFGNAM  CKLFTGLYHI
hCCR5   IFGFVGNMLV  ILILINCKRL  KSMTDIYLLN  LAISDLFFLL  TVPFWAHYA.  AAQWDFGNTM  CQLLTGLYFI
hCCR1   VIGLVGNILV  VLVLVQVKRL  KNMTSIYLLN  LAISDLLFLF  TLPFWIDYKL  KDDWVFGDAM  CKILSGFYYT
hCCR3   TVGLLGNVVV  VMILIKYRRL  RIMTNIYLLN  LAISDLLFLV  TLPFWIHYVR  GHNWVFGHGM  CKLLSGFYHT
hCCR4   VFGLLGNSVV  VLVLFKYKRL  RSMTDVYLLN  LAISDLLFVF  SLPFWGYYA.  ADQWVFGLGL  CKMISWMYLV
hCCR8   VFSLLGNSLV  ILVLVVCKKL  RSITDVYLLN  LALSDLLFVF  SFPFQTYYLL  .DQWVFGTVM  CKVVSGFYYI
        ----------  -----       -----       ------II--  --------               C  ------ hCCR6   NFNCGMLLLT  CISMDRYIAI  VQATKSFRLR  SRTLPRSKII  CLVVWGLSVI  ISSSSFVFNQ  KYNTLGSDVC
hCCR7   SFFSGMLLLL  CISIDRYVAI  VQAVSAHRHR  ARVLLISKLS  CVGIWILATV  LSIPELLYSD  LQRSSSEQAM
hD6     NFYSGIFFIS  CMSLDKYLEI  VHAQ..PYHR  LRTRAKSLLL  ATIVWAVSLA  VSIPDNVFVQ  THENPKGVWN
mD6     NFYCGIFFIT  CMSLDKYLEI  VHAQ..PLHR  PKAQFRNLLL  IVMVWITSLA  ISVPENVFVQ  IHQTLDGVWH
hCCR2a  GYFGGIFFII  LLTIDRYLAI  VHAV..FALK  ARTVTFGVVT  SVITWLVAVF  ASVPGIIFTK  C.QKEDSVYV
hCCR2b  GYFGGIFFII  LLTIDRYLAI  VHAV..FALK  ARTVTFGVVT  SVITWLVAVF  ASVPGIIFTK  C.QKEDSVYV
hCCR5   GFFSGIFFII  LLTIDRYLAV  VHAV..FALK  ARTVTFGVVT  SVITWVVAVF  ASLPGIIFTR  S.QKEGLHYT
hCCR1   GLYSEIFFII  LLTIDRYLAI  VHAV..FALR  ARTVTFGVIT  SIIIWALAIL  ASMPGLYFSK  T.QWEFTHHT
hCCR3   GLYSEIFFII  LLTIDRYLAI  VHAV..FALR  ARTVTFGVIT  SIVTWGLAVL  AALPEFIFYE  T.EELFEETL
hCCR4   GFYSGIFFVM  LMSIDRYLAI  VHAV..FSLR  ARTLTYGVIT  SLATWSVAVF  ASLPGFLFST  C.YTERNHTY
hCCR8   GFYSSMFFIT  LMSVDRYLAV  VHAV..YALK  VRTIRMGTTL  CLAVWLTAIN  ATIPLLVFYQ  V.ASEDGVLQ
        ----III---  ---                                -------    -----IV---  --------- hCCR6   EPKYQTVSVP  IRWKLLMLGL  ELLFGFFFPL  MFMIFCYTFI  VKTLVQAQN.  SKRHKAIRVI  IAVVLVFLAC
hCCR7   ..RCSLITEH  VEAFITIQVA  QMVIGFLVPL  LAMSFCYLVI  IRTLLQARN.  FERNKAIKVI  IAVVVFIVF
hD6     CHADFGGHGT  .IWKLFLRFQ  QNLLGFLLPL  LAMIFFYSRI  GCVLVRLRPA  GQG.RALKIA  AALVVAFFVL
mD6     CYADFGGHAT  .IWKLYLRFQ  LNLLGFLLPL  LAMIFFYSRI  GCVLVRLRPP  GQG.RALRMA  AALVIVFFML
hCCR2a  CGPYFP....  RGWNNFHTIM  RNILGLVLPL  LIMVICYSGI  LKTLLRCRNE  KKRHRAVRVI  FTIMIVYFLF
hCCR2b  CGPYFP....  RGWNNFHTIM  RNILGLVLPL  LIMVICYSGI  LKTLLRCRNE  KKRHRAVRVI  FTIMIVYFLF
hCCR5   CSSHFPYSQY  QFWKNFQTLK  IVILGLVLPL  LVMVICYSGI  LKTLLRCRNE  KKRHRAVRLI  FTIMIVYFLF
hCCR1   CSLHFPHESL  REWKLFQALK  LNLFGLVLPL  LVMIICYTGI  IKILLRRPNE  KK.SKAVRLI  FVIMIIFFLF
hCCR3   CSALYPEDTV  YSWRHFHTLR  NTIFCLVLPL  LVMAICYTAI  IKTLLRCPSK  KK.YKAIRLI  FVIMAVFFIF
hCCR4   CYSFYNQQTL  K.WKIFTNFK  MNILGLLIPF  TIFMFCYIKI  LHQLKRCQNH  NKT.KAIRLV  LIVVIASLLF
hCCR8   C           ------     -----V----  -----                  ----  ------VI-- hCCR6   QIPHN.MVLL  VTAANLGKMN  RSCQSEKLIG  YTKTVTEVLA  FLHCCLNPVL  YAFIGQKFRN  YFLKILKDLW
hCCR7   QLPYNGVVLA  QTVANFNITS  STCELSKQLN  IAYDVTYSLA  CVRCCVNPFL  YAFIGVKFRN  DLFKLFKDLG
hD6     WFPYYLTLFL  HSLLDLF F   .NCEISHRLD  YTLQVTESLA  FSHCCFTPVL  YAFCSHRFRQ  YLKAFLSVM.
mD6     WTPYNIVILL  NTFQEFFGLS  .NCESTSQLD  QATQVTETLG  HTHCCINPII  YAFVGEKFRS  LFHIALG.CR
hCCR2a  WTPYNIVILL  NTFQEFFGLS  .NCESTSQLD  QATQVTETLG  MTHCCINPII  YAFVGEKFRR  YLSVFFR.KH
hCCR2b  WAPYNIVLLL  NTFQEFFGLN  .NCSSSNRLD  QAMQVTETLG  MTHCCINPII  YAFVGEKFRN  YLLVFFQ.KH
hCCR5   WTPYNLTILI  SVFQDFLFTH  .ECEQSRHLD  LAVQVTEVIA  YTHCCVNPVI  YAFVGERFRK  YLRQLFH.RR
hCCR1   WTPYNVAILL  SSYQSILFGN  .DCERSKHLD  LVMLVTEVIA  YSHCCMNPVI  YAFVGERFRK  YLRHFFH.RH
hCCR3   WTPYNIVLFL  ETLVELEVLQ  .DCTFERYLD  YAIQATETLA  FVHCCVNPII  YFFLGEKFRK  YILQLFKTCR
hCCR4   WVPFNVVLFL  TSLHSMHILD  .GCSISQQLT  YATHVTEIIS  FTHCCVNPVI  YAFVGEKFKK  HLSEIFQ.KS
hCCR8   ----------              C          ---  ------VII  -----------
```

Fig. 3

```
hCCR6    CVRRKYKSSG  FSCAGRYSEN  ISRQTSETAD  NDNAVVLHYV  IES*------  -----
hCCR7    CLSQEQLRQW  SSCRHIRRSS  MSVEAETTTT  FSP*------  ----------  -----
hD6      LGWHLAPGTA  QASLSSCSES  SILTAQEEMT  GMNDLGERQS  ENYPNKEDVG  NKSA*
mD6      LRWHQAPGTP  S...SNHSES  SRVTAQEDVV  SMNDLGERQS  EDSLNKGENG  NT*--
hCCR2a   IAPLQKPVCG  GPGVRPGKNV  KVTTQGLLDG  RGKGKSIGRA  PEASLQDKEG  A*---
hCCR2b   ITKRFCKQCP  VFYRETVDGV  TSTNTPSTGE  QEVSAGL*--  ----------  -----
hCCR5    IAKRFCKCCS  IFQQEAPERA  SSVYTRSTGE  QEISVGL*--  ----------  -----
hCCR1    VAVHLVKWLP  FLSVDRLERV  SST.SPSTGE  HELSAGF*--  ----------  -----
hCCR3    LLMHLGRYIP  FLPSEKLERT  SSV.SPSTAE  PELSIVF*--  ----------  -----
hCCR4    GLFVLCQYCG  LLQIYSADTP  SSSYTQSTMD  HDLHDAL*--  ----------  -----
hCCR8    CSQIFNYLGR  QMPRESCEKS  SSCQQHSSRS  SSVDYIL*--  ----------  -----
```

Fig. 3 (continued)

SEQUENCE LISTING (1) GENERAL INFORMATION:

(iii) NUMBER OF SEQUENCES: 56

(2) INFORMATION FOR SEQ ID NO:1:

(i) SEQUENCE CHARACTERISTICS:
        (A) LENGTH: 1181 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 13..1164

(xi) SEQUENCE DESCRIPTION: SEQ ID NO:1:

```
GGATCCTCCA AC ATG GCC GCC ACT GCC TCT CCG CAG CCA CTC GCC ACT        48
              Met Ala Ala Thr Ala Ser Pro Gln Pro Leu Ala Thr
                1               5                  10

GAG GAT GCC GAT TCT GAG AAT AGC AGC TTC TAT TAC TAT GAC TAC CTG      96
Glu Asp Ala Asp Ser Glu Asn Ser Ser Phe Tyr Tyr Tyr Asp Tyr Leu
            15                  20                  25

GAT GAA GTG GCC TTC ATG CTC TGC AGG AAG GAT GCA GTG GTG TCC TTT     144
Asp Glu Val Ala Phe Met Leu Cys Arg Lys Asp Ala Val Val Ser Phe
        30                  35                  40

GGC AAA GTC TTC CTC CCA GTC TTC TAT AGC CTG ATT TTT GTG TTG GGC     192
Gly Lys Val Phe Leu Pro Val Phe Tyr Ser Leu Ile Phe Val Leu Gly
 45                  50                  55                  60

CTC AGC GGG AAC CTC CTT CTT CTC ATG GTC TTG CTC CGT TAC GTG CCT     240
Leu Ser Gly Asn Leu Leu Leu Leu Met Val Leu Leu Arg Tyr Val Pro
                    65                  70                  75

CGC AGG CGG ATG GTT GAG ATC TAT CTG CTG AAT CTG GCC ATC TCC AAC     288
Arg Arg Arg Met Val Glu Ile Tyr Leu Leu Asn Leu Ala Ile Ser Asn
                80                  85                  90
```

```
CTT CTG TTT CTG GTG ACA CTG CCC TTC TGG GGC ATC TCC GTG GCC TGG      336
Leu Leu Phe Leu Val Thr Leu Pro Phe Trp Gly Ile Ser Val Ala Trp
         95                 100                 105

CAT TGG GTC TTC GGG AGT TTC TTG TGC AAG ATG GTG AGC ACT CTT TAT      384
His Trp Val Phe Gly Ser Phe Leu Cys Lys Met Val Ser Thr Leu Tyr
    110                 115                 120

ACT ATT AAC TTT TAC AGT GGC ATC TTT TTC ATT AGC TGC ATG AGC CTG      432
Thr Ile Asn Phe Tyr Ser Gly Ile Phe Phe Ile Ser Cys Met Ser Leu
125                 130                 135                 140

GAC AAG TAC CTG GAG ATC GTT CAT GCT CAG CCC TAC CAC AGG CTG AGG      480
Asp Lys Tyr Leu Glu Ile Val His Ala Gln Pro Tyr His Arg Leu Arg
                145                 150                 155

ACC CGG GCC AAG AGC CTG CTC CTT GCT ACC ATA GTA TGG GCT GTG TCC      528
Thr Arg Ala Lys Ser Leu Leu Leu Ala Thr Ile Val Trp Ala Val Ser
            160                 165                 170

CTG GCC GTC TCC ATC CCT GAT ATG GTC TTT GTA CAG ACA CAT GAA AAT      576
Leu Ala Val Ser Ile Pro Asp Met Val Phe Val Gln Thr His Glu Asn
        175                 180                 185

CCC AAG GGT GTG TGG AAC TGC CAC GCA GAT TTC GGC GGG CAT GGG ACC      624
Pro Lys Gly Val Trp Asn Cys His Ala Asp Phe Gly Gly His Gly Thr
    190                 195                 200

ATT TGG AAG CTC TTC CTC CGC TTC CAG CAG AAC CTC CTA GGG TTT CTC      672
Ile Trp Lys Leu Phe Leu Arg Phe Gln Gln Asn Leu Leu Gly Phe Leu
205                 210                 215                 220

CTT CCA CTC CTT GCC ATG ATC TTC TTC TAC TCC CGT ATT GGT TGT GTC      720
Leu Pro Leu Leu Ala Met Ile Phe Phe Tyr Ser Arg Ile Gly Cys Val
                225                 230                 235

TTG GTG AGG CTG AGG CCC GCA GGC CAG GGC CGG GCT TTA AAA ATA GCT      768
Leu Val Arg Leu Arg Pro Ala Gly Gln Gly Arg Ala Leu Lys Ile Ala
            240                 245                 250

GCA GCC TTG GTG GTG GCC TTC TTC GTG CTA TGG TTC CCA TAC AAT CTC      816
Ala Ala Leu Val Val Ala Phe Phe Val Leu Trp Phe Pro Tyr Asn Leu
        255                 260                 265

ACC TTG TTT CTG CAT ACG CTG TTG GAC CTG CAA GTA TTC GGG AAC TGT      864
Thr Leu Phe Leu His Thr Leu Leu Asp Leu Gln Val Phe Gly Asn Cys
    270                 275                 280

GAG GTC AGC CAG CAT CTA GAC TAC GCA CTC CAG GTA ACA GAG AGC ATC      912
Glu Val Ser Gln His Leu Asp Tyr Ala Leu Gln Val Thr Glu Ser Ile
285                 290                 295                 300

GCC TTC CTT CAC TGC TGC TTT TCC CCC ATC CTG TAT GCC TTC TCC AGT      960
Ala Phe Leu His Cys Cys Phe Ser Pro Ile Leu Tyr Ala Phe Ser Ser
                305                 310                 315

CAC CGC TTC CGC CAG TAC CTG AAG GCT TTC CTG GCT GCC GTG CTT GGA     1008
His Arg Phe Arg Gln Tyr Leu Lys Ala Phe Leu Ala Ala Val Leu Gly
            320                 325                 330

TGG CAC CTG GCA CCT GGC ACT GCC CAG GCC TCA TTA TCC AGC TGT TCT     1056
Trp His Leu Ala Pro Gly Thr Ala Gln Ala Ser Leu Ser Ser Cys Ser
        335                 340                 345

GAG AGC AGC ATA CTT ACT GCC CAA GAG GAA ATG ACT GGC ATG AAT GAC     1104
Glu Ser Ser Ile Leu Thr Ala Gln Glu Glu Met Thr Gly Met Asn Asp
    350                 355                 360

CTT GGA GAG AGG CAG TCT GAG AAC TAC CCT AAC AAG GAG GAT GTG GGG     1152
Leu Gly Glu Arg Gln Ser Glu Asn Tyr Pro Asn Lys Glu Asp Val Gly
365                 370                 375                 380

AAT AAA TCA GCC TGAGTGACCG CGGCCGC                                  1181
Asn Lys Ser Ala (2) INFORMATION FOR SEQ ID NO:2:
```

(i) SEQUENCE CHARACTERISTICS:
    (A) LENGTH: 384 amino acids
    (B) TYPE: amino acid
    (D) TOPOLOGY: linear (ii) MOLECULE TYPE: protein (xi) SEQUENCE DESCRIPTION: SEQ ID NO:2:

```
Met Ala Ala Thr Ala Ser Pro Gln Pro Leu Ala Thr Glu Asp Ala Asp
 1               5                  10                  15

Ser Glu Asn Ser Ser Phe Tyr Tyr Tyr Asp Tyr Leu Asp Glu Val Ala
            20                  25                  30

Phe Met Leu Cys Arg Lys Asp Ala Val Val Ser Phe Gly Lys Val Phe
        35                  40                  45

Leu Pro Val Phe Tyr Ser Leu Ile Phe Val Leu Gly Leu Ser Gly Asn
    50                  55                  60

Leu Leu Leu Leu Met Val Leu Arg Tyr Val Pro Arg Arg Arg Met
65                  70                  75                  80

Val Glu Ile Tyr Leu Leu Asn Leu Ala Ile Ser Asn Leu Leu Phe Leu
                85                  90                  95

Val Thr Leu Pro Phe Trp Gly Ile Ser Val Ala Trp His Trp Val Phe
                100                 105                 110

Gly Ser Phe Leu Cys Lys Met Val Ser Thr Leu Tyr Thr Ile Asn Phe
            115                 120                 125

Tyr Ser Gly Ile Phe Phe Ile Ser Cys Met Ser Leu Asp Lys Tyr Leu
        130                 135                 140

Glu Ile Val His Ala Gln Pro Tyr His Arg Leu Arg Thr Arg Ala Lys
145                 150                 155                 160

Ser Leu Leu Leu Ala Thr Ile Val Trp Ala Val Ser Leu Ala Val Ser
                165                 170                 175

Ile Pro Asp Met Val Phe Val Gln Thr His Glu Asn Pro Lys Gly Val
                180                 185                 190

Trp Asn Cys His Ala Asp Phe Gly Gly His Gly Thr Ile Trp Lys Leu
            195                 200                 205

Phe Leu Arg Phe Gln Gln Asn Leu Leu Gly Phe Leu Leu Pro Leu Leu
        210                 215                 220

Ala Met Ile Phe Phe Tyr Ser Arg Ile Gly Cys Val Leu Val Arg Leu
225                 230                 235                 240

Arg Pro Ala Gly Gln Gly Arg Ala Leu Lys Ile Ala Ala Ala Leu Val
                245                 250                 255

Val Ala Phe Phe Val Leu Trp Phe Pro Tyr Asn Leu Thr Leu Phe Leu
                260                 265                 270

His Thr Leu Leu Asp Leu Gln Val Phe Gly Asn Cys Glu Val Ser Gln
            275                 280                 285

His Leu Asp Tyr Ala Leu Gln Val Thr Glu Ser Ile Ala Phe Leu His
        290                 295                 300

Cys Cys Phe Ser Pro Ile Leu Tyr Ala Phe Ser Ser His Arg Phe Arg
305                 310                 315                 320

Gln Tyr Leu Lys Ala Phe Leu Ala Ala Val Leu Gly Trp His Leu Ala
                325                 330                 335

Pro Gly Thr Ala Gln Ala Ser Leu Ser Ser Cys Ser Glu Ser Ser Ile
                340                 345                 350

Leu Thr Ala Gln Glu Glu Met Thr Gly Met Asn Asp Leu Gly Glu Arg
            355                 360                 365

Gln Ser Glu Asn Tyr Pro Asn Lys Glu Asp Val Gly Asn Lys Ser Ala
```

(2) INFORMATION FOR SEQ ID NO:3:

(i) SEQUENCE CHARACTERISTICS:
    (A) LENGTH: 1155 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..1152

(xi) SEQUENCE DESCRIPTION: SEQ ID NO:3:

```
ATG GCC GCC ACT GCC TCT CCG CAG CCA CTC GCC ACT GAG GAT GCC GAT    48
Met Ala Ala Thr Ala Ser Pro Gln Pro Leu Ala Thr Glu Asp Ala Asp
  1               5                  10                  15

TCT GAG AAT AGC AGC TTC TAT TAC TAT GAC TAC CTG GAT GAA GTG GCC    96
Ser Glu Asn Ser Ser Phe Tyr Tyr Tyr Asp Tyr Leu Asp Glu Val Ala
             20                  25                  30

TTC ATG CTC TGC AGG AAG GAT GCA GTG GTG TCC TTT GGC AAA GTC TTC   144
Phe Met Leu Cys Arg Lys Asp Ala Val Val Ser Phe Gly Lys Val Phe
         35                  40                  45

CTC CCA GTC TTC TAT AGC CTG ATT TTT GTG TTG GGC CTC AGC GGG AAC   192
Leu Pro Val Phe Tyr Ser Leu Ile Phe Val Leu Gly Leu Ser Gly Asn
     50                  55                  60

CTC CTT CTT CTC ATG GTC TTG CTC CGT TAC GTG CCT CGC AGG CGG ATG   240
Leu Leu Leu Leu Met Val Leu Leu Arg Tyr Val Pro Arg Arg Arg Met
 65                  70                  75                  80

GTT GAG ATC TAT CTG CTG AAT CTG GCC ATC TCC AAC CTT CTG TTT CTG   288
Val Glu Ile Tyr Leu Leu Asn Leu Ala Ile Ser Asn Leu Leu Phe Leu
                 85                  90                  95

GTG ACA CTG CCC TTC TGG GGC ATC TCC GTG GCC TGG CAT TGG GTC TTC   336
Val Thr Leu Pro Phe Trp Gly Ile Ser Val Ala Trp His Trp Val Phe
            100                 105                 110

GGG AGT TTC TTG TGC AAG ATG GTG AGC ACT CTT TAT ACT ATT AAC TTT   384
Gly Ser Phe Leu Cys Lys Met Val Ser Thr Leu Tyr Thr Ile Asn Phe
        115                 120                 125

TAC AGT GGC ATC TTT TTC ATT AGC TGC ATG AGC CTG GAC AAG TAC CTG   432
Tyr Ser Gly Ile Phe Phe Ile Ser Cys Met Ser Leu Asp Lys Tyr Leu
    130                 135                 140

GAG ATC GTT CAT GCT CAG CCC TAC CAC AGG CTG AGG ACC CGG GCC AAG   480
Glu Ile Val His Ala Gln Pro Tyr His Arg Leu Arg Thr Arg Ala Lys
145                 150                 155                 160

AGC CTG CTC CTT GCT ACC ATA GTA TGG GCT GTG TCC CTG GCC GTC TCC   528
Ser Leu Leu Leu Ala Thr Ile Val Trp Ala Val Ser Leu Ala Val Ser
                165                 170                 175

ATC CCT GAT ATG GTC TTT GTA CAG ACA CAT GAA AAT CCC AAG GGT GTG   576
Ile Pro Asp Met Val Phe Val Gln Thr His Glu Asn Pro Lys Gly Val
            180                 185                 190

TGG AAC TGC CAC GCA GAT TTC GGC GGG CAT GGG ACC ATT TGG AAG CTC   624
Trp Asn Cys His Ala Asp Phe Gly Gly His Gly Thr Ile Trp Lys Leu
        195                 200                 205

TTC CTC CGC TTC CAG CAG AAC CTC CTA GGG TTT CTC CTT CCA CTC CTT   672
Phe Leu Arg Phe Gln Gln Asn Leu Leu Gly Phe Leu Leu Pro Leu Leu
    210                 215                 220

GCC ATG ATC TTC TTC TAC TCC CGT ATT GGT TGT GTC TTG GTG AGG CTG   720
Ala Met Ile Phe Phe Tyr Ser Arg Ile Gly Cys Val Leu Val Arg Leu
225                 230                 235                 240
```

```
AGG CCC GCA GGC CAG GGC CGG GCT TTA AAA ATA GCT GCA GCC TTG GTG      768
Arg Pro Ala Gly Gln Gly Arg Ala Leu Lys Ile Ala Ala Ala Leu Val
                245                 250                 255

GTG GCC TTC TTC GTG CTA TGG TTC CCA TAC AAT CTC ACC TTG TTT CTG      816
Val Ala Phe Phe Val Leu Trp Phe Pro Tyr Asn Leu Thr Leu Phe Leu
            260                 265                 270

CAT ACG CTG TTG GAC CTG CAA GTA TTC GGG AAC TGT GAG GTC AGC CAG      864
His Thr Leu Leu Asp Leu Gln Val Phe Gly Asn Cys Glu Val Ser Gln
                275                 280                 285

CAT CTA GAC TAC GCA CTC CAG GTA ACA GAG AGC ATC GCC TTC CTT CAC      912
His Leu Asp Tyr Ala Leu Gln Val Thr Glu Ser Ile Ala Phe Leu His
            290                 295                 300

TGC TGC TTT TCC CCC ATC CTG TAT GCC TTC TCC AGT CAC CGC TTC CGC      960
Cys Cys Phe Ser Pro Ile Leu Tyr Ala Phe Ser Ser His Arg Phe Arg
305                 310                 315                 320

CAG TAC CTG AAG GCT TTC CTG GCT GCC GTG CTT GGA TGG CAC CTG GCA     1008
Gln Tyr Leu Lys Ala Phe Leu Ala Ala Val Leu Gly Trp His Leu Ala
                325                 330                 335

CCT GGC ACT GCC CAG GCC TCA TTA TCC AGC TGT TCT GAG AGC AGC ATA     1056
Pro Gly Thr Ala Gln Ala Ser Leu Ser Ser Cys Ser Glu Ser Ser Ile
            340                 345                 350

CTT ACT GCC CAA GAG GAA ATG ACT GGC ATG AAT GAC CTT GGA GAG AGG     1104
Leu Thr Ala Gln Glu Glu Met Thr Gly Met Asn Asp Leu Gly Glu Arg
                355                 360                 365

CAG TCT GAG AAC TAC CCT AAC AAG GAG GAT GTG GGG AAT AAA TCA GCC     1152
Gln Ser Glu Asn Tyr Pro Asn Lys Glu Asp Val Gly Asn Lys Ser Ala
            370                 375                 380

TGA                                                                  1155
```

(2) INFORMATION FOR SEQ ID NO:4:

(i) SEQUENCE CHARACTERISTICS:
        (A) LENGTH: 1664 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 193..1326

(xi) SEQUENCE DESCRIPTION: SEQ ID NO:4:

```
CAAAAAATTG GGAAGGGGGG GTTTCGGGAA AAGGGGGGG GGATTTGGGG AAGGGGGGAA       60

AGCAAAGCCG CCAGGGGGTG GGGGAAAGGG GAGCAGGGGA ACCAACAACC AGCATTCGGC      120

AGTTAACCAG TTAAGCCCAG TTTTTTAGCT GGGGGCAGAG ACCAGATCCT GCAAGCATCA      180

GAGCTCGAGG AC ATG CCC ACC GTT GCT TCC CCA CTG CCT CTC ACC ACC         228
              Met Pro Thr Val Ala Ser Pro Leu Pro Leu Thr Thr
                1               5                   10

GTC GGT TCC GAG AAC AGC AGC TCC ATC TAC GAC TAC GAC TAC TTA GAT      276
Val Gly Ser Glu Asn Ser Ser Ser Ile Tyr Asp Tyr Asp Tyr Leu Asp
            15                  20                  25

GAT ATG ACC ATC TTG GTT TGC AGG AAG GAC GAG GTC CTG TCC TTT GGA      324
Asp Met Thr Ile Leu Val Cys Arg Lys Asp Glu Val Leu Ser Phe Gly
        30                  35                  40

AGA GTC TTT CTG CCG GTC GTC TAC AGC CTG ATC TTC GTG CTG GGC TTG      372
Arg Val Phe Leu Pro Val Val Tyr Ser Leu Ile Phe Val Leu Gly Leu
    45                  50                  55                  60

GCT GGA AAC CTC CTC CTC CTG GTG GTG TTG CTC CAC TCT GCA CCT CGA      420
Ala Gly Asn Leu Leu Leu Leu Val Val Leu Leu His Ser Ala Pro Arg
```

```
                          65                    70                     75
AGA CGG ACG ATG GAG CTT TAC CTG CTG AAC CTG GCC GTC TCC AAC CTC           468
Arg Arg Thr Met Glu Leu Tyr Leu Leu Asn Leu Ala Val Ser Asn Leu
                80                  85                  90

TTG TTT GTA GTG ACT ATG CCC TTC TGG GCC ATC TCT GTG GCC TGG CAT           516
Leu Phe Val Val Thr Met Pro Phe Trp Ala Ile Ser Val Ala Trp His
            95                 100                 105

TGG GTT TTT GGT AGT TTC CTG TGC AAG GTG ATA AGC ACT CTC TAC TCT           564
Trp Val Phe Gly Ser Phe Leu Cys Lys Val Ile Ser Thr Leu Tyr Ser
    110                 115                 120

ATT AAC TTT TAC TGT GGT ATC TTC TTC ATC ACC TGC ATG AGC CTG GAC           612
Ile Asn Phe Tyr Cys Gly Ile Phe Phe Ile Thr Cys Met Ser Leu Asp
125                 130                 135                 140

AAA TAC CTG GAG ATT GTC CAC GCT CAG CCT CTC CAC AGA CCG AAG GCC           660
Lys Tyr Leu Glu Ile Val His Ala Gln Pro Leu His Arg Pro Lys Ala
                145                 150                 155

CAG TTC AGG AAC CTG CTT CTC ATT GTC ATG GTG TGG ATC ACA TCC CTG           708
Gln Phe Arg Asn Leu Leu Leu Ile Val Met Val Trp Ile Thr Ser Leu
            160                 165                 170

GCC ATC TCT GTC CCA GAA ATG GTC TTT GTG CAG ATC CAC CAG ACC TTA           756
Ala Ile Ser Val Pro Glu Met Val Phe Val Gln Ile His Gln Thr Leu
        175                 180                 185

GAT GGT GTG TGG CAC TGC TAT GCG GAT TTT GGC GGA CAT GCG ACC ATT           804
Asp Gly Val Trp His Cys Tyr Ala Asp Phe Gly Gly His Ala Thr Ile
    190                 195                 200

TGG AAG CTG TAC CTG CGC TTC CAG CTG AAC CTT CTG GGG TTT CTC CTC           852
Trp Lys Leu Tyr Leu Arg Phe Gln Leu Asn Leu Leu Gly Phe Leu Leu
205                 210                 215                 220

CCA CTC TTG GCC ATG ATC TTC TTT TAC TCC CGC ATC GGT TGC GTT CTG           900
Pro Leu Leu Ala Met Ile Phe Phe Tyr Ser Arg Ile Gly Cys Val Leu
                225                 230                 235

GTC AGG CTG AGG CCG CCA GGC CAG GGC CGG GCT CTG AGG ATG GCC GCG           948
Val Arg Leu Arg Pro Pro Gly Gln Gly Arg Ala Leu Arg Met Ala Ala
            240                 245                 250

GCC CTG GTG ATA GTT TTC TTC ATG CTG TGG TTC CCA TAT TAC CTC ACC           996
Ala Leu Val Ile Val Phe Phe Met Leu Trp Phe Pro Tyr Tyr Leu Thr
        255                 260                 265

TTG TTT CTG CAC TCG TTG CTG GAC CTG CAT GTC TTT GGG AAC TGT GAG          1044
Leu Phe Leu His Ser Leu Leu Asp Leu His Val Phe Gly Asn Cys Glu
    270                 275                 280

ATC AGC CAC CGT CTG GAC TAT ACG TTG CAG GTG ACA GAG AGC CTG GCC          1092
Ile Ser His Arg Leu Asp Tyr Thr Leu Gln Val Thr Glu Ser Leu Ala
285                 290                 295                 300

TTC TCC CAC TGC TGC TTC ACC CCG GTC CTC TAC GCC TTC TGC AGT CAC          1140
Phe Ser His Cys Cys Phe Thr Pro Val Leu Tyr Ala Phe Cys Ser His
                305                 310                 315

CGC TTC CGC CGG TAC CTG AAG GCA TTT CTG TCT GTG ATG TTG AGA TGG          1188
Arg Phe Arg Arg Tyr Leu Lys Ala Phe Leu Ser Val Met Leu Arg Trp
            320                 325                 330

CAC CAG GCA CCT GGC ACC CCT TCC TCT AAC CAT TCT GAG AGC AGC AGG          1236
His Gln Ala Pro Gly Thr Pro Ser Ser Asn His Ser Glu Ser Ser Arg
        335                 340                 345

GTT ACT GCC CAG GAA GAC GTG GTC AGC ATG AAT GAC CTT GGG GAG AGG          1284
Val Thr Ala Gln Glu Asp Val Val Ser Met Asn Asp Leu Gly Glu Arg
    350                 355                 360

CAG TCT GAG GAC TCC CTT AAC AAG GGG GAG ATG GGG AAT ACT              1326
Gln Ser Glu Asp Ser Leu Asn Lys Gly Glu Met Gly Asn Thr
365                 370                 375

TAGGCCCGAG TGATCAGCCA CGGTCTGGGA ACAGCACTGC TCTCTCTGAG GGACAGCGTG         1386
```

```
ACTGTGCTGC TCGCCCCAGT GGTTCCCAAC CACCAGCAGG CCTTACTCAT TACTGTCTCT    1446

TCCTCCTTCT GCTTCCTGGA CCCCATCCTC TCTGCTGAAC CACTTCAGCT CTTCACTGAT    1506

CTCCCTCCAC TTCCACCCCA GCGCTTCTGT GGCTTCCTGG CCCTCAGCAG CCAATGAGGT    1566

CACTCCACTC TTAGCCTTCA GACCTTCAAG GGCCATGTGA TCATTGATGT GACTTTATTT    1626

CCACCGTACT CCCTCCTGGT CTCTGGGTTC AGGGCACA                            1664
```

(2) INFORMATION FOR SEQ ID NO:5:

(i) SEQUENCE CHARACTERISTICS:
        (A) LENGTH: 378 amino acids
        (B) TYPE: amino acid
        (D) TOPOLOGY: linear (ii) MOLECULE TYPE: protein (xi) SEQUENCE DESCRIPTION: SEQ ID NO:5:

```
Met Pro Thr Val Ala Ser Pro Leu Pro Leu Thr Thr Val Gly Ser Glu
 1               5                  10                  15

Asn Ser Ser Ile Tyr Asp Tyr Asp Tyr Leu Asp Asp Met Thr Ile
            20                  25                  30

Leu Val Cys Arg Lys Asp Glu Val Leu Ser Phe Gly Arg Val Phe Leu
            35                  40                  45

Pro Val Val Tyr Ser Leu Ile Phe Val Leu Gly Leu Ala Gly Asn Leu
        50                  55                  60

Leu Leu Leu Val Val Leu Leu His Ser Ala Pro Arg Arg Arg Thr Met
 65                  70                  75                  80

Glu Leu Tyr Leu Leu Asn Leu Ala Val Ser Asn Leu Leu Phe Val Val
                85                  90                  95

Thr Met Pro Phe Trp Ala Ile Ser Val Ala Trp His Trp Val Phe Gly
               100                 105                 110

Ser Phe Leu Cys Lys Val Ile Ser Thr Leu Tyr Ser Ile Asn Phe Tyr
           115                 120                 125

Cys Gly Ile Phe Phe Ile Thr Cys Met Ser Leu Asp Lys Tyr Leu Glu
       130                 135                 140

Ile Val His Ala Gln Pro Leu His Arg Pro Lys Ala Gln Phe Arg Asn
145                 150                 155                 160

Leu Leu Leu Ile Val Met Val Trp Ile Thr Ser Leu Ala Ile Ser Val
               165                 170                 175

Pro Glu Met Val Phe Val Gln Ile His Gln Thr Leu Asp Gly Val Trp
           180                 185                 190

His Cys Tyr Ala Asp Phe Gly Gly His Ala Thr Ile Trp Lys Leu Tyr
       195                 200                 205

Leu Arg Phe Gln Leu Asn Leu Leu Gly Phe Leu Leu Pro Leu Leu Ala
   210                 215                 220

Met Ile Phe Phe Tyr Ser Arg Ile Gly Cys Val Leu Val Arg Leu Arg
225                 230                 235                 240

Pro Pro Gly Gln Gly Arg Ala Leu Arg Met Ala Ala Ala Leu Val Ile
               245                 250                 255

Val Phe Phe Met Leu Trp Phe Pro Tyr Tyr Leu Thr Leu Phe Leu His
           260                 265                 270

Ser Leu Leu Asp Leu His Val Phe Gly Asn Cys Glu Ile Ser His Arg
       275                 280                 285

Leu Asp Tyr Thr Leu Gln Val Thr Glu Ser Leu Ala Phe Ser His Cys
   290                 295                 300
```

```
Cys Phe Thr Pro Val Leu Tyr Ala Phe Cys Ser His Arg Phe Arg Arg
305                 310                 315                 320

Tyr Leu Lys Ala Phe Leu Ser Val Met Leu Arg Trp His Gln Ala Pro
                325                 330                 335

Gly Thr Pro Ser Ser Asn His Ser Glu Ser Ser Arg Val Thr Ala Gln
                340                 345                 350

Glu Asp Val Val Ser Met Asn Asp Leu Gly Glu Arg Gln Ser Glu Asp
                355                 360                 365

Ser Leu Asn Lys Gly Glu Met Gly Asn Thr
        370                 375
```

(2) INFORMATION FOR SEQ ID NO:6:

(i) SEQUENCE CHARACTERISTICS:
        (A) LENGTH: 1137 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1134

(xi) SEQUENCE DESCRIPTION: SEQ ID NO:6:

```
ATG CCC ACC GTT GCT TCC CCA CTG CCT CTC ACC ACC GTC GGT TCC GAG      48
Met Pro Thr Val Ala Ser Pro Leu Pro Leu Thr Thr Val Gly Ser Glu
 1               5                  10                  15

AAC AGC AGC TCC ATC TAC GAC TAC GAC TAC TTA GAT GAT ATG ACC ATC      96
Asn Ser Ser Ser Ile Tyr Asp Tyr Asp Tyr Leu Asp Asp Met Thr Ile
            20                  25                  30

TTG GTT TGC AGG AAG GAC GAG GTC CTG TCC TTT GGA AGA GTC TTT CTG     144
Leu Val Cys Arg Lys Asp Glu Val Leu Ser Phe Gly Arg Val Phe Leu
        35                  40                  45

CCG GTC GTC TAC AGC CTG ATC TTC GTG CTG GGC TTG GCT GGA AAC CTC     192
Pro Val Val Tyr Ser Leu Ile Phe Val Leu Gly Leu Ala Gly Asn Leu
    50                  55                  60

CTC CTC CTG GTG GTG TTG CTC CAC TCT GCA CCT CGA AGA CGG ACG ATG     240
Leu Leu Leu Val Val Leu Leu His Ser Ala Pro Arg Arg Arg Thr Met
65                  70                  75                  80

GAG CTT TAC CTG CTG AAC CTG GCC GTC TCC AAC CTC TTG TTT GTA GTG     288
Glu Leu Tyr Leu Leu Asn Leu Ala Val Ser Asn Leu Leu Phe Val Val
                85                  90                  95

ACT ATG CCC TTC TGG GCC ATC TCT GTG GCC TGG CAT TGG GTT TTT GGT     336
Thr Met Pro Phe Trp Ala Ile Ser Val Ala Trp His Trp Val Phe Gly
            100                 105                 110

AGT TTC CTG TGC AAG GTG ATA AGC ACT CTC TAC TCT ATT AAC TTT TAC     384
Ser Phe Leu Cys Lys Val Ile Ser Thr Leu Tyr Ser Ile Asn Phe Tyr
        115                 120                 125

TGT GGT ATC TTC TTC ATC ACC TGC ATG AGC CTG GAC AAA TAC CTG GAG     432
Cys Gly Ile Phe Phe Ile Thr Cys Met Ser Leu Asp Lys Tyr Leu Glu
    130                 135                 140

ATT GTC CAC GCT CAG CCT CTC CAC AGA CCG AAG GCC CAG TTC AGG AAC     480
Ile Val His Ala Gln Pro Leu His Arg Pro Lys Ala Gln Phe Arg Asn
145                 150                 155                 160

CTG CTT CTC ATT GTC ATG GTG TGG ATC ACA TCC CTG GCC ATC TCT GTC     528
Leu Leu Leu Ile Val Met Val Trp Ile Thr Ser Leu Ala Ile Ser Val
                165                 170                 175

CCA GAA ATG GTC TTT GTG CAG ATC CAC CAG ACC TTA GAT GGT GTG TGG     576
Pro Glu Met Val Phe Val Gln Ile His Gln Thr Leu Asp Gly Val Trp
```

-continued

```
                      180                 185                 190
CAC TGC TAT GCG GAT TTT GGC GGA CAT GCG ACC ATT TGG AAG CTG TAC        624
His Cys Tyr Ala Asp Phe Gly Gly His Ala Thr Ile Trp Lys Leu Tyr
            195                 200                 205

CTG CGC TTC CAG CTG AAC CTT CTG GGG TTT CTC CTC CCA CTC TTG GCC        672
Leu Arg Phe Gln Leu Asn Leu Leu Gly Phe Leu Leu Pro Leu Leu Ala
    210                 215                 220

ATG ATC TTC TTT TAC TCC CGC ATC GGT TGC GTT CTG GTC AGG CTG AGG        720
Met Ile Phe Phe Tyr Ser Arg Ile Gly Cys Val Leu Val Arg Leu Arg
225                 230                 235                 240

CCG CCA GGC CAG GGC CGG GCT CTG AGG ATG GCC GCG GCC CTG GTG ATA        768
Pro Pro Gly Gln Gly Arg Ala Leu Arg Met Ala Ala Ala Leu Val Ile
                245                 250                 255

GTT TTC TTC ATG CTG TGG TTC CCA TAT TAC CTC ACC TTG TTT CTG CAC        816
Val Phe Phe Met Leu Trp Phe Pro Tyr Tyr Leu Thr Leu Phe Leu His
            260                 265                 270

TCG TTG CTG GAC CTG CAT GTC TTT GGG AAC TGT GAG ATC AGC CAC CGT        864
Ser Leu Leu Asp Leu His Val Phe Gly Asn Cys Glu Ile Ser His Arg
        275                 280                 285

CTG GAC TAT ACG TTG CAG GTG ACA GAG AGC CTG GCC TTC TCC CAC TGC        912
Leu Asp Tyr Thr Leu Gln Val Thr Glu Ser Leu Ala Phe Ser His Cys
    290                 295                 300

TGC TTC ACC CCG GTC CTC TAC GCC TTC TGC AGT CAC CGC TTC CGC CGG        960
Cys Phe Thr Pro Val Leu Tyr Ala Phe Cys Ser His Arg Phe Arg Arg
305                 310                 315                 320

TAC CTG AAG GCA TTT CTG TCT GTG ATG TTG AGA TGG CAC CAG GCA CCT       1008
Tyr Leu Lys Ala Phe Leu Ser Val Met Leu Arg Trp His Gln Ala Pro
                325                 330                 335

GGC ACC CCT TCC TCT AAC CAT TCT GAG AGC AGC AGG GTT ACT GCC CAG       1056
Gly Thr Pro Ser Ser Asn His Ser Glu Ser Ser Arg Val Thr Ala Gln
            340                 345                 350

GAA GAC GTG GTC AGC ATG AAT GAC CTT GGG GAG AGG CAG TCT GAG GAC       1104
Glu Asp Val Val Ser Met Asn Asp Leu Gly Glu Arg Gln Ser Glu Asp
        355                 360                 365

TCC CTT AAC AAG GGG GAG ATG GGG AAT ACT TAG                           1137
Ser Leu Asn Lys Gly Glu Met Gly Asn Thr
        370                 375
```

(2) INFORMATION FOR SEQ ID NO:7:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:7:

Asp Xaa Tyr Leu Xaa Ile Val His Ala
1               5

(2) INFORMATION FOR SEQ ID NO:8:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:8:

Arg Xaa Tyr Leu Lys
1               5

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6
        (D) OTHER INFORMATION: /note= "N=I which is Inosine"

(ix) FEATURE:
        (A) NAME/KEY: misc_feature
        (B) LOCATION: 9
        (D) OTHER INFORMATION: /note= "N=A OR G"

(ix) FEATURE:
        (A) NAME/KEY: misc_feature
        (B) LOCATION: 12
        (D) OTHER INFORMATION: /note= "N=G OR C"

(ix) FEATURE:
        (A) NAME/KEY: misc_feature
        (B) LOCATION: 15
        (D) OTHER INFORMATION: /note= "N=G OR C"

(ix) FEATURE:
        (A) NAME/KEY: misc_feature
        (B) LOCATION: 18
        (D) OTHER INFORMATION: /note= "N=I which is Inosine"

(xi) SEQUENCE DESCRIPTION: SEQ ID NO:9:

GGGGCNCANC TNCTNCCNCC                                    20

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6
        (D) OTHER INFORMATION: /note= "N=A or C"

(ix) FEATURE:
        (A) NAME/KEY: misc_feature
        (B) LOCATION: 7
        (D) OTHER INFORMATION: /note= "N=I which is Inosine"

(ix) FEATURE:
        (A) NAME/KEY: misc_feature
        (B) LOCATION: 9
        (D) OTHER INFORMATION: /note= "N=I which is Inosine"

(ix) FEATURE:
        (A) NAME/KEY: misc_feature
        (B) LOCATION: 15
        (D) OTHER INFORMATION: /note= "N=T or C"

(xi) SEQUENCE DESCRIPTION: SEQ ID NO:10:

ACCACNNTNT TTGANTATG                                     19

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 3
        (D) OTHER INFORMATION: /note= "N=T or C"

(ix) FEATURE:
        (A) NAME/KEY: misc_feature
        (B) LOCATION: 6
        (D) OTHER INFORMATION: /note= "N=T or C"

(ix) FEATURE:
        (A) NAME/KEY: misc_feature
        (B) LOCATION: 9
        (D) OTHER INFORMATION: /note= "N=I which is Inosine"

(ix) FEATURE:
        (A) NAME/KEY: misc_feature
        (B) LOCATION: 12
        (D) OTHER INFORMATION: /note= "N=I which is Inosine"

(ix) FEATURE:
        (A) NAME/KEY: misc_feature
        (B) LOCATION: 18
        (D) OTHER INFORMATION: /note= "N=C or G"

(xi) SEQUENCE DESCRIPTION: SEQ ID NO:11:

ATNTANCTNC TNAACCTNGC                                            20

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 3
        (D) OTHER INFORMATION: /note= "N=I which is Inosine"

(ix) FEATURE:
        (A) NAME/KEY: misc_feature
        (B) LOCATION: 6
        (D) OTHER INFORMATION: /note= "N=G or C"

(ix) FEATURE:
        (A) NAME/KEY: misc_feature
        (B) LOCATION: 15
        (D) OTHER INFORMATION: /note= "N=A or G"

(ix) FEATURE:
        (A) NAME/KEY: misc_feature
        (B) LOCATION: 18
        (D) OTHER INFORMATION: /note= "N=A or G"

(xi) SEQUENCE DESCRIPTION: SEQ ID NO:12:

GTNAGNAGGA TGATNAANAA AAT                                       23

(2) INFORMATION FOR SEQ ID NO:13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 4
            (D) OTHER INFORMATION: /note= "N=I which is Inosine"

(ix) FEATURE:
            (A) NAME/KEY: misc_feature
            (B) LOCATION: 7
            (D) OTHER INFORMATION: /note= "N=A or G"

(ix) FEATURE:
            (A) NAME/KEY: misc_feature
            (B) LOCATION: 18
            (D) OTHER INFORMATION: /note= "N=G or T"

(xi) SEQUENCE DESCRIPTION: SEQ ID NO:13:

GACNATNGCC AGGTACCNGT C                                                    21

(2) INFORMATION FOR SEQ ID NO:14:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 3
            (D) OTHER INFORMATION: /note= "N=C or T"

(ix) FEATURE:
            (A) NAME/KEY: misc_feature
            (B) LOCATION: 6
            (D) OTHER INFORMATION: /note= "N=I which is Inosine"

(ix) FEATURE:
            (A) NAME/KEY: misc_feature
            (B) LOCATION: 12
            (D) OTHER INFORMATION: /note= "N=C or T"

(ix) FEATURE:
            (A) NAME/KEY: misc_feature
            (B) LOCATION: 15
            (D) OTHER INFORMATION: /note= "N=C or T"

(ix) FEATURE:
            (A) NAME/KEY: misc_feature
            (B) LOCATION: 18
            (D) OTHER INFORMATION: /note= "N=C or T"

(ix) FEATURE:
            (A) NAME/KEY: misc_feature
            (B) LOCATION: 21
            (D) OTHER INFORMATION: /note= "N=I which is Inosine"

(ix) FEATURE:
            (A) NAME/KEY: misc_feature
            (B) LOCATION: 24
            (D) OTHER INFORMATION: /note= "N=C or T"

(xi) SEQUENCE DESCRIPTION: SEQ ID NO:14:

TGNGGNATCT TNTTNATNAC NTGNATC                                              27

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6
        (D) OTHER INFORMATION: /note= "N=A or G"

(ix) FEATURE:
        (A) NAME/KEY: misc_feature
        (B) LOCATION: 9
        (D) OTHER INFORMATION: /note= "N=C or T"

(ix) FEATURE:
        (A) NAME/KEY: misc_feature
        (B) LOCATION: 12
        (D) OTHER INFORMATION: /note= "N=I which is Inosine"

(ix) FEATURE:
        (A) NAME/KEY: misc_feature
        (B) LOCATION: 15
        (D) OTHER INFORMATION: /note= "N=A or G"

(ix) FEATURE:
        (A) NAME/KEY: misc_feature
        (B) LOCATION: 18
        (D) OTHER INFORMATION: /note= "N=C or T"

(ix) FEATURE:
        (A) NAME/KEY: misc_feature
        (B) LOCATION: 21
        (D) OTHER INFORMATION: /note= "N=I which is Inosine"

(ix) FEATURE:
        (A) NAME/KEY: misc_feature
        (B) LOCATION: 24
        (D) OTHER INFORMATION: /note= "N=C or T"

(xi) SEQUENCE DESCRIPTION: SEQ ID NO:15:

GACAANTANC TNGANATNGT NCANGC                                            26

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 7
        (D) OTHER INFORMATION: /note= "N=Inoside"

(ix) FEATURE:
        (A) NAME/KEY: misc_feature
        (B) LOCATION: 10
        (D) OTHER INFORMATION: /note= "N=I which is Inosine"

(ix) FEATURE:
        (A) NAME/KEY: misc_feature
        (B) LOCATION: 13
        (D) OTHER INFORMATION: /note= "N=I which is Inosine"

(ix) FEATURE:
        (A) NAME/KEY: misc_feature
        (B) LOCATION: 16
        (D) OTHER INFORMATION: /note= "N=A or G"

```
    (ix) FEATURE:
          (A) NAME/KEY: misc_feature
          (B) LOCATION: 19
          (D) OTHER INFORMATION: /note= "N=A or G"

(ix) FEATURE:
          (A) NAME/KEY: misc_feature
          (B) LOCATION: 22
          (D) OTHER INFORMATION: /note= "N=A or G"

(xi) SEQUENCE DESCRIPTION: SEQ ID NO:16:

GTACAGNACN GGNGTNCANC ANTG                                              24

(2) INFORMATION FOR SEQ ID NO:17:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:17:

GTGACAGAGA GCCTGGCCTT C                                                 21

(2) INFORMATION FOR SEQ ID NO:18:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:18:

GGAAGAGACA GTAATGAGTA AGGC                                              24

(2) INFORMATION FOR SEQ ID NO:19:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:19:

CGTTCATGCT CAGCCCTAC                                                    19

(2) INFORMATION FOR SEQ ID NO:20:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:20:

CTGGAGTGCG TAGTCTAGAT GC                                                22

(2) INFORMATION FOR SEQ ID NO:21:

(i) SEQUENCE CHARACTERISTICS:
          (A) LENGTH: 20 base pairs
```

(B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:21:

GCCGCGGCCC CTGGTGATAG                                                    20

(2) INFORMATION FOR SEQ ID NO:22:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:22:

AGCGGTGACT GCAGAAGGCG TAGA                                               24

(2) INFORMATION FOR SEQ ID NO:23:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:23:

CCAGGAAGCA GAAGGAGGAA GAGACAGTAA TGAGTAAGGC                               40

(2) INFORMATION FOR SEQ ID NO:24:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:24:

TGGAGAAGGC ATACAGGATG GGGGAAAAGC AGCAGTGAAA                               40

(2) INFORMATION FOR SEQ ID NO:25:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:25:

TGGTCACTCA GGCTGATTTA TTCCCCACAT CCTTGTT                                  37

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:26:

TGGGCATGTC CTCGAGCTCT                                              20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TGATCCACAC CATGACAATG                                              20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

TGCGCCTGTC CACGTGCACA                                              20

(2) INFORMATION FOR SEQ ID NO:29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

ACAGTCCCAT GGTACAAGTT CAGCA                                        25

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GAACTTGTAC CATGGGACTG T                                            21

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

```
GAACTCGGAT CCCATGTGAA GGTGT                                              25

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

CTTCACATGG GATCCGAGTT C                                                  21

(2) INFORMATION FOR SEQ ID NO:33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

AACCGTAGAT CTGCTGCACA CCAAC                                              25

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

GTGTGCAGCA GATCTACGGT T                                                  21

(2) INFORMATION FOR SEQ ID NO:35:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

TAGACCAAGC TTAGACTGAC ATCCT                                              25

(2) INFORMATION FOR SEQ ID NO:36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

AGTTACACGT CTAGAATGGC T                                                  21

(2) INFORMATION FOR SEQ ID NO:37:
```

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:37:

TAGTCCGAAT TCAAGCAAGA GCACA                                              25

(2) INFORMATION FOR SEQ ID NO:38:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:38:

CTCTTGCTTG AATTCGGACT A                                                  21

(2) INFORMATION FOR SEQ ID NO:39:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:39:

GAGAGAAGCT TGGATCCTCC AACATGGCCG                                         30

(2) INFORMATION FOR SEQ ID NO:40:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:40:

GAAGCTGCTC TGCTCAGAAT CGGCAT                                             26

(2) INFORMATION FOR SEQ ID NO:41:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:41:

ATGCCGATTC TGAGCAGAGC AGCTTC                                             26

(2) INFORMATION FOR SEQ ID NO:42:

(i) SEQUENCE CHARACTERISTICS:
            (A) LENGTH: 24 base pairs
            (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:42:

AGGTTGGAGA TGGCCAGATT CAGC                                              24

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

TGGTTGAGAT CTATCTGCTG AATC                                              24

(2) INFORMATION FOR SEQ ID NO:44:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

CATGAACGAT CGCCAGGTAC CTGTCCAGGC TC                                     32

(2) INFORMATION FOR SEQ ID NO:45:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

GAGCCTCAGG TACCTGGCGA TCGTTCATG                                         29

(2) INFORMATION FOR SEQ ID NO:46:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

GACACAGCCC ATACTATGGT AGC                                               23

(2) INFORMATION FOR SEQ ID NO:47:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

TGGTTGAGAT CTATCTGCTG AATCTGGCCA TCTCCGACCT TC        42

(2) INFORMATION FOR SEQ ID NO:48:

(i) SEQUENCE CHARACTERISTICS:
      (A) LENGTH: 374 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:48:

```
Met Ser Gly Glu Ser Met Asn Phe Ser Asp Val Phe Asp Ser Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45

Val Pro Ile Ala Tyr Ser Leu Ile Cys Val Phe Gly Leu Leu Gly Asn
    50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val
                85                  90                  95

Leu Thr Leu Pro Phe Trp Ala Val Ser His Ala Thr Gly Ala Trp Val
            100                 105                 110

Phe Ser Asn Ala Thr Cys Lys Leu Leu Lys Gly Ile Tyr Ala Ile Asn
        115                 120                 125

Phe Asn Cys Gly Met Leu Leu Leu Thr Cys Ile Ser Met Asp Arg Tyr
    130                 135                 140

Ile Ala Ile Val Gln Ala Thr Lys Ser Phe Arg Leu Arg Ser Arg Thr
145                 150                 155                 160

Leu Pro Arg Ser Lys Ile Ile Cys Leu Val Val Trp Gly Leu Ser Val
                165                 170                 175

Ile Ile Ser Ser Ser Thr Phe Val Phe Asn Gln Lys Tyr Asn Thr Gln
            180                 185                 190

Gly Ser Asp Val Cys Glu Pro Lys Tyr Gln Thr Val Ser Glu Pro Ile
        195                 200                 205

Arg Trp Lys Leu Leu Met Leu Gly Leu Glu Leu Leu Phe Gly Phe Phe
    210                 215                 220

Ile Pro Leu Met Phe Met Ile Phe Cys Tyr Thr Phe Ile Val Lys Thr
225                 230                 235                 240

Leu Val Gln Ala Gln Asn Ser Lys Arg His Lys Ala Ile Arg Val Ile
                245                 250                 255

Ile Ala Val Val Leu Val Phe Leu Ala Cys Gln Ile Pro His Asn Met
            260                 265                 270

Val Leu Leu Val Thr Ala Ala Asn Leu Gly Lys Met Asn Arg Ser Cys
        275                 280                 285

Gln Ser Glu Lys Leu Ile Gly Tyr Thr Lys Thr Val Thr Glu Val Leu
    290                 295                 300

Ala Phe Leu His Cys Cys Leu Asn Pro Val Leu Tyr Ala Phe Ile Gly
305                 310                 315                 320
```

```
Gln Lys Phe Arg Asn Tyr Phe Leu Lys Ile Leu Lys Asp Leu Trp Cys
            325                 330                 335

Val Arg Arg Lys Tyr Lys Ser Ser Gly Phe Ser Cys Ala Gly Arg Tyr
            340                 345                 350

Ser Glu Asn Ile Ser Arg Gln Thr Ser Glu Thr Ala Asp Asn Asp Asn
            355                 360                 365

Ala Ser Ser Phe Thr Met
            370

(2) INFORMATION FOR SEQ ID NO:49:

(i) SEQUENCE CHARACTERISTICS:
        (A) LENGTH: 378 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:49:

Met Asp Leu Gly Lys Pro Met Lys Ser Val Leu Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
            35                  40                  45

Ser Lys Lys Asp Val Arg Asn Phe Lys Ala Trp Phe Leu Pro Ile Met
        50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
            115                 120                 125

Cys Lys Leu Ile Phe Ala Ile Tyr Lys Met Ser Phe Phe Ser Gly Met
            130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ser Ala Ile Leu Ala Thr Val Leu Ser Ile Pro
            180                 185                 190

Glu Leu Leu Tyr Ser Asp Leu Gln Arg Ser Ser Ser Glu Gln Ala Met
            195                 200                 205

Arg Cys Ser Leu Ile Thr Glu His Val Glu Ala Phe Ile Thr Ile Gln
            210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
            260                 265                 270

Ile Val Phe Gln Leu Pro Tyr Asn Gly Val Val Leu Ala Gln Thr Val
            275                 280                 285
```

```
Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Ile Phe Lys Leu Phe Lys Asp Leu Gly Cys Leu Ser Gln Glu Gln Leu
                340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
    370                 375
```

(2) INFORMATION FOR SEQ ID NO:50:

(i) SEQUENCE CHARACTERISTICS:
        (A) LENGTH: 360 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:50:

```
Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
                35                  40                  45

Tyr Ser Leu Val Phe Ile Phe Gly Phe Val Gly Asn Met Leu Val Val
            50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
                100                 105                 110

Cys Lys Leu Phe Thr Gly Leu Tyr His Ile Gly Tyr Phe Gly Gly Ile
            115                 120                 125

Phe Phe Ile Ile Leu Leu Thr Ile Asp Arg Tyr Leu Ala Ile Val His
130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
                180                 185                 190

Tyr Phe Pro Arg Gly Trp Asn Asn Phe His Thr Ile Met Arg Asn Ile
            195                 200                 205

Leu Gly Leu Val Leu Pro Leu Leu Ile Met Val Ile Cys Tyr Ser Gly
            210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
```

```
                     245                 250                 255
Thr Pro Tyr Asn Ile Val Ile Leu Leu Asn Thr Phe Gln Glu Phe Phe
                260                 265                 270

Gly Leu Ser Asn Cys Glu Ser Thr Ser Gln Leu Asp Gln Ala Thr Gln
            275                 280                 285

Val Thr Glu Thr Leu Gly Met Thr His Cys Cys Ile Asn Pro Ile Ile
        290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                325                 330                 335

Arg Glu Thr Val Asp Gly Val Thr Ser Thr Asn Thr Pro Ser Thr Gly
                340                 345                 350

Glu Gln Glu Val Ser Ala Gly Leu
            355                 360

(2) INFORMATION FOR SEQ ID NO:51:

(i) SEQUENCE CHARACTERISTICS:
        (A) LENGTH: 360 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:51:

Met Leu Ser Thr Ser Arg Ser Arg Phe Ile Arg Asn Thr Asn Gly Ser
1               5                   10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
            35                  40                  45

Tyr Ser Leu Val Phe Ile Phe Gly Phe Val Gly Asn Met Leu Val Val
        50                  55                  60

Leu Ile Leu Ile Asn Cys Lys Lys Leu Lys Ser Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Leu Gly Gly Ile
        115                 120                 125

Phe Phe Ile Ile Leu Leu Thr Ile Asp Arg Tyr Leu Ala Ile Val His
        130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Glu Glu Asp Ser Val Tyr Ile Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
        210                 215                 220
```

```
Ile Leu Lys Thr Leu Leu Arg Cys Arg Asn Glu Lys Lys Arg His Arg
225                 230                 235                 240

Ala Val Arg Leu Ile Phe Thr Ile Met Ile Val Tyr Phe Leu Phe Trp
            245                 250                 255

Thr Pro Tyr Asn Ile Val Ile Leu Leu Asn Thr Phe Gln Glu Phe Phe
                260                 265                 270

Gly Leu Ser Asn Cys Glu Ser Thr Arg Gln Leu Asp Gln Ala Thr Gln
            275                 280                 285

Val Thr Glu Thr Leu Gly Met Thr His Cys Cys Ile Asn Pro Ile Ile
290                 295                 300

Tyr Ala Phe Val Gly Glu Lys Phe Arg Arg Tyr Leu Ser Met Phe Phe
305                 310                 315                 320

Arg Lys Tyr Ile Thr Lys Arg Phe Cys Lys Gln Cys Pro Val Phe Tyr
                325                 330                 335

Arg Glu Thr Val Asp Gly Val Thr Ser Thr Asn Thr Pro Ser Thr Ala
                340                 345                 350

Glu Gln Glu Val Ser Ala Gly Leu
            355             360

(2) INFORMATION FOR SEQ ID NO:52:

(i) SEQUENCE CHARACTERISTICS:
        (A) LENGTH: 352 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:52:

Met Asp Tyr Gln Val Ser Ser Pro Ile Tyr Asp Ile Asp Tyr Tyr Thr
1               5                   10                  15

Ser Glu Pro Cys Gln Lys Ile Asn Val Lys Gln Ile Ala Ala Arg Leu
                20                  25                  30

Leu Pro Pro Leu Tyr Ser Leu Val Phe Ile Phe Gly Phe Val Gly Asn
            35                  40                  45

Met Leu Val Ile Leu Ile Leu Ile Asn Cys Lys Arg Leu Lys Ser Met
50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
            115                 120                 125

Ala Ile Val His Ala Val Phe Ala Leu Lys Ala Arg Thr Val Thr Phe
130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
            195                 200                 205
```

```
Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
                260                 265                 270

Asn Arg Leu Asp Gln Ala Met Gln Val Thr Glu Thr Leu Gly Met Thr
                275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
                340                 345                 350
```

(2) INFORMATION FOR SEQ ID NO:53:

(i) SEQUENCE CHARACTERISTICS:
        (A) LENGTH: 355 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:53:

```
Met Glu Thr Pro Asn Thr Thr Glu Asp Tyr Asp Met Ile Thr Glu Phe
1               5                   10                  15

Asp Tyr Gly Asp Ala Thr Pro Cys His Lys Val Asn Glu Arg Ala Ile
                20                  25                  30

Leu Ala Gln Leu Leu Pro Pro Leu Tyr Ser Leu Val Phe Val Ile Gly
            35                  40                  45

Val Val Gly Asn Leu Leu Val Val Leu Val Leu Val Gln Tyr Lys Arg
    50                  55                  60

Leu Lys Asn Met Thr Asn Ile Tyr Leu Leu Asn Leu Ala Ile Ser Asp
65                  70                  75                  80

Leu Leu Phe Leu Phe Thr Leu Pro Phe Leu Ile Tyr Tyr Lys Ser Thr
                85                  90                  95

Asp Asp Trp Ile Phe Gly Asp Ala Met Cys Lys Ile Leu Ser Gly Phe
                100                 105                 110

Tyr Tyr Thr Gly Leu Tyr Ser Glu Ile Phe Phe Ile Ile Leu Leu Thr
            115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Ile Ile Trp Ala Leu
145                 150                 155                 160

Ala Ile Leu Ala Ser Ser Pro Leu Met Tyr Phe Ser Lys Thr Gln Trp
                165                 170                 175

Asn Ile Val Arg His Ser Cys Asn Ile His Phe Pro Tyr Glu Ser Phe
                180                 185                 190

Gln Gln Trp Lys Leu Phe Gln Ala Leu Lys Leu Asn Leu Phe Gly Leu
```

```
                195                 200                      205
Val Leu Pro Leu Leu Val Met Ile Val Cys Tyr Thr Gly Ile Ile Lys
        210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
                245                 250                 255

Leu Thr Glu Leu Ile Ser Val Phe Gln Glu Phe Leu Phe Thr His Leu
                260                 265                 270

Cys Glu Gln Asn Arg Gln Leu Asp Leu Ala Met Glu Val Thr Glu Val
                275                 280                 285

Ile Ala Asn Met His Cys Cys Val Asn Pro Val Ile Tyr Ala Phe Ala
        290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Gly Asp Arg Leu
                325                 330                 335

Glu Arg Val Ser Ser Thr Ser Pro Ser Thr Gly Glu His Glu Leu Ser
                340                 345                 350

Ala Gly Phe
        355

(2) INFORMATION FOR SEQ ID NO:54:

(i) SEQUENCE CHARACTERISTICS:
        (A) LENGTH: 355 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:54:

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
                20                  25                  30

Met Ala Gln Phe Val Pro Pro Leu Tyr Ser Leu Val Phe Thr Val Gly
        35                  40                  45

Leu Leu Gly Asn Val Val Val Met Ile Leu Ile Lys Tyr Arg Arg
50                  55                  60

Leu Arg Ile Met Thr Asn Ile Tyr Leu Leu Asn Leu Ala Ile Ser Asp
65                  70                  75                  80

Leu Leu Phe Leu Val Thr Leu Pro Phe Trp Ile His Tyr Val Arg Gly
                85                  90                  95

His Asn Trp Val Phe Gly His Gly Met Cys Lys Leu Leu Ser Gly Phe
                100                 105                 110

Tyr His Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
        130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175
```

-continued

```
Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Phe Cys Leu
            195                 200                 205

Val Leu Pro Leu Leu Val Met Ala Ile Cys Tyr Thr Gly Ile Ile Lys
            210                 215                 220

Thr Leu Leu Arg Cys Pro Ser Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
                260                 265                 270

Cys Glu Arg Ser Lys His Leu Asp Leu Val Met Leu Val Thr Glu Val
            275                 280                 285

Ile Ala Tyr Ser His Cys Cys Met Asn Pro Val Ile Tyr Ala Phe Val
            290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355
```

(2) INFORMATION FOR SEQ ID NO:55:

(i) SEQUENCE CHARACTERISTICS:
        (A) LENGTH: 360 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:55:

```
Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
                20                  25                  30

Gly Ile Lys Ala Phe Gly Glu Leu Phe Leu Pro Pro Leu Tyr Ser Leu
            35                  40                  45

Val Phe Val Phe Gly Leu Leu Gly Asn Ser Val Val Val Leu Val Leu
    50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
            115                 120                 125

Met Leu Met Ser Ile Asp Arg Tyr Leu Ala Ile Val His Ala Val Phe
        130                 135                 140

Ser Leu Arg Ala Arg Thr Leu Thr Tyr Gly Val Ile Thr Ser Leu Ala
145                 150                 155                 160
```

```
Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
        195                 200                 205

Leu Gly Leu Val Ile Pro Leu Gly Ile Met Leu Phe Cys Tyr Ser Met
    210                 215                 220

Ile Ile Arg Thr Leu Gln His Cys Lys Asn Glu Lys Lys Asn Lys Ala
225                 230                 235                 240

Val Lys Met Ile Phe Ala Val Val Leu Phe Leu Gly Phe Trp Thr
                245                 250                 255

Pro Tyr Asn Ile Val Leu Phe Leu Glu Thr Leu Val Glu Leu Glu Val
                260                 265                 270

Leu Gln Asp Cys Thr Phe Glu Arg Tyr Leu Asp Tyr Ala Ile Gln Ala
            275                 280                 285

Thr Glu Thr Leu Ala Phe Val His Cys Cys Leu Asn Pro Ile Ile Tyr
        290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
                340                 345                 350

Asp His Asp Leu His Asp Ala Leu
            355                 360

(2) INFORMATION FOR SEQ ID NO:56:

(i) SEQUENCE CHARACTERISTICS:
        (A) LENGTH: 355 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:56:

Met Asp Tyr Thr Leu Asp Leu Ser Val Thr Thr Val Thr Asp Tyr Tyr
1               5                   10                  15

Tyr Pro Asp Ile Phe Ser Ser Pro Cys Asp Ala Glu Leu Ile Gln Thr
                20                  25                  30

Asn Gly Lys Leu Leu Leu Ala Val Phe Tyr Cys Leu Leu Phe Val Phe
            35                  40                  45

Ser Leu Leu Gly Asn Ser Leu Val Ile Leu Val Leu Val Val Cys Lys
    50                  55                  60

Lys Leu Arg Ser Ile Thr Asp Val Tyr Leu Leu Asn Leu Ala Leu Ser
65                  70                  75                  80

Asp Leu Leu Phe Val Phe Ser Phe Pro Phe Gln Thr Tyr Tyr Leu Leu
                85                  90                  95

Asp Gln Trp Val Phe Gly Thr Val Met Cys Lys Val Val Ser Gly Phe
            100                 105                 110

Tyr Tyr Ile Gly Phe Tyr Ser Ser Met Phe Phe Ile Thr Leu Met Ser
        115                 120                 125

Val Asp Arg Tyr Leu Ala Val Val His Ala Val Tyr Ala Leu Lys Val
```

-continued

```
        130                 135                 140
Arg Thr Ile Arg Met Gly Thr Thr Leu Cys Leu Ala Val Trp Leu Thr
145                 150                 155                 160

Ala Ile Met Ala Thr Ile Pro Leu Leu Val Phe Tyr Gln Val Ala Ser
                165                 170                 175

Glu Asp Gly Val Leu Gln Cys Tyr Ser Phe Tyr Asn Gln Gln Thr Leu
                180                 185                 190

Lys Trp Lys Ile Phe Thr Asn Phe Lys Met Asn Ile Leu Gly Leu Leu
            195                 200                 205

Ile Pro Phe Thr Ile Phe Met Phe Cys Tyr Ile Lys Ile Leu His Gln
        210                 215                 220

Leu Lys Arg Cys Gln Asn His Asn Lys Thr Lys Ala Ile Arg Leu Val
225                 230                 235                 240

Leu Ile Val Val Ile Ala Ser Leu Leu Phe Trp Val Pro Phe Asn Val
                245                 250                 255

Val Leu Phe Leu Thr Ser Leu His Ser Met His Ile Leu Asp Gly Cys
                260                 265                 270

Ser Ile Ser Gln Gln Leu Thr Tyr Ala Thr His Val Thr Glu Ile Ile
            275                 280                 285

Ser Phe Thr His Cys Cys Val Asn Pro Val Ile Tyr Ala Phe Val Gly
        290                 295                 300

Glu Lys Phe Lys Lys His Leu Ser Glu Ile Phe Gln Lys Ser Cys Ser
305                 310                 315                 320

Gln Ile Phe Asn Tyr Leu Gly Arg Gln Met Pro Arg Glu Ser Cys Glu
                325                 330                 335

Lys Ser Ser Ser Cys Gln Gln His Ser Ser Arg Ser Ser Ser Val Asp
                340                 345                 350

Tyr Ile Leu
        355
```

NUCLEIC ACID MOLECULES OF THE PROTEIN-COUPLED HEPTAHELICAL RECEPTOR SUPERFAMILY AND USES THEREFOR

BACKGROUND OF THE INVENTION

The chemokine family of peptides is defined on the basis of sequence homology and on the presence of variations on a conserved cysteine motif. Schall (1996) *Cytokine* 3:165–183; and Oppenheim et al. (1991) *Annu. Rev. Immunol.* 9:617–648. The family can be subdivided on the basis of this motif into two major subfamilies, in which members of each contain four characteristic cysteine residues. This subdivision therefore defines the CC or β-chemokine family in which the first two cysteines are juxtaposed, and the CXC or α-chemokine family in which there is an intervening amino acid between the first two cysteines. Two other subfamilies have subsequently been described which have variations in the number of amino acids between the first two cysteine residues. Kelner et al. (1994) *Science* 266:1395–1399; Domer et al. (1997) *J. Biol. Chem.* 272:8817–8823; and Bazan et al. (1996) *Nature* 385:640–644.

Chemokines display a range of in vitro and in vivo functions ranging from proinflammatory activities on a range of cell types to proliferative regulatory activities. All of the functions of the chemokine family are believed to be signaled into a responsive cell using members of the G protein-coupled heptahelical receptor family. To date several α-chemokine and β-chemokine receptors have been described. See, for e.g., Neote et al. (1993) *Cell* 72:415–425; Ponath et al. (1996) *J. Exp. Med.* 183:2437–2448; and Power et al. (1995) *J. Biol. Chem.* 270:19495–19500.

SUMMARY OF THE INVENTION

The present invention is based, at least in part, on the discovery of novel molecules of the G protein-coupled heptahelical receptor superfamily, referred to herein as "D6" nucleic acid and protein molecules. Accordingly, in one aspect, this invention provides isolated nucleic acid molecules encoding D6 proteins or biologically active portions thereof, as well as nucleic acid fragments suitable as primers or hybridization probes for the detection of D6-encoding nucleic acids.

In one embodiment, a D6 nucleic acid molecule is at least about 60–65%, more preferably at least about 70–75%, even more preferably at least about 78–80%, 80–85%, and most preferably at least about 90–95% or more homologous to the nucleotide sequence shown in SEQ ID NO:1, SEQ ID NO:3, or a complement thereof. In yet another embodiment, a D6 nucleic acid molecule is at least about 60–65%, more preferably at least about 70–75%, even more preferably at least about 80–85%, and most preferably at least about 88–95% or more homologous to the nucleotide sequence shown in SEQ ID NO:4, SEQ ID NO:6, or a complement thereof. In a preferred embodiment, the isolated nucleic acid molecule has the nucleotide sequence shown SEQ ID NO:1, SEQ ID NO:3, or a complement thereof. In another preferred embodiment, the isolated nucleic acid molecule has the nucleotide sequence shown in SEQ ID NO:4, SEQ ID NO:6, or a complement thereof.

In another preferred embodiment, the isolated nucleic acid molecule comprises nucleotides 1–858 of SEQ ID NO:1 or nucleotides 1–846 of SEQ ID NO:3. In another embodiment, the isolated nucleic acid molecule comprises nucleotides 955–1172 of SEQ ID NO:1 or nucleotides 943–1160 of SEQ ID NO:3. In yet another embodiment, the isolated nucleic acid molecule comprises nucleotides 1–117 or nucleotides 1395–1664 of SEQ ID NO:4.

In another embodiment, a D6 nucleic acid molecule includes a nucleotide sequence encoding a protein having an amino acid sequence sufficiently homologous to the amino acid sequence of SEQ ID NO:2, or SEQ ID NO:5. In another preferred embodiment, a D6 nucleic acid molecule include a nucleotide sequence encoding a protein having an amino acid sequence 65–70%, preferably at least about, 71–75%, 75–80%, more preferably at least about 85–90%, and most preferably at least about 95% or more homologous to the amino acid sequence of SEQ ID NO:2. In another embodiment, a D6 nucleic acid molecule include a nucleotide sequence encoding a protein having an amino acid sequence 65–70%, preferably at least about, 71–75%, 75–80%, more preferably at least about 85–90%, and most preferably at least about 90–95% or more homologous to the amino acid sequence of SEQ ID NO:5. In yet another embodiment, the nucleic acid molecule encodes the amino acid sequence of human or murine D6.

In another embodiment, an isolated nucleic acid molecule of the present invention encodes a protein, preferably a D6 protein, which includes at least two, three, preferably four conserved cysteine residues, and is membrane bound. In another embodiment, an isolated nucleic acid molecule of the present invention encodes a protein, preferably a D6 protein, which includes at least one G-protein docking motif, at least two conserved cysteine-residues, and is membrane bound. In a further embodiment, an isolated nucleic acid molecule of the present invention encodes a protein, preferably a D6 protein, which has seven transmembrane domains. In yet another embodiment, a D6 nucleic acid molecule encodes a D6 protein and is a naturally occurring nucleotide sequence.

Another embodiment of the invention features nucleic acid molecules, preferably D6 nucleic acid molecules, which specifically detect D6 nucleic acid molecules relative to nucleic acid molecules encoding non-D6 proteins. For example, in one embodiment, such a nucleic acid molecule hybridizes under stringent conditions to a nucleic acid molecule comprising the nucleotides 1–858, 1–69, 955–969, or 955–1172 of the nucleotide sequence shown in SEQ ID NO:1, or to nucleotides 1–846, 1–57, 943–957 or 943–1160 of nucleotide sequence shown in SEQ ID NO:3. In another embodiment, the nucleic acid molecule is at least 215 nucleotides in length and hybridizes under stringent conditions to a nucleic acid molecule comprising the nucleotide sequence shown in SEQ ID NO:1, or SEQ ID NO:3, respectively, or a complement thereof. In yet another embodiment, a D6 nucleic acid molecule hybridizes under stringent conditions to a nucleic acid molecule comprising the nucleotides 1–117 of the nucleotide sequence shown in SEQ ID NO:4, or to nucleotides 1395–1664 of nucleotide sequence shown in SEQ ID NO:4. In a further embodiment, the nucleic acid molecule is at least 117 nucleotides in length and hybridizes under stringent conditions to a nucleic acid molecule comprising the nucleotide sequence shown in SEQ ID NO:4 or SEQ ID NO:6, respectively, or a complement thereof.

Another embodiment of the invention provides an isolated nucleic acid molecule which is antisense to the coding strand of a D6 nucleic acid molecule.

Another aspect of the invention provides a vector comprising a D6 nucleic acid molecule. In certain embodiments, the vector is a recombinant expression vector. In another embodiment, the invention provides a host cell containing a vector of the invention. The invention also provides a method for producing a protein, preferably a D6 protein, by culturing in a suitable medium, a host cell of the invention containing a recombinant expression vector such that a D6 protein is produced.

Another aspect of this invention features isolated or recombinant D6 proteins and polypeptides. In one embodiment, an isolated protein, preferably a D6 protein, has at least two, three, preferably four conserved cysteine residues, and is membrane bound. In another embodiment, an isolated protein, preferably a D6 protein, has at least one G-protein docking motif, at least two conserved cysteine-residues, and is membrane bound. In a further embodiment, an isolated protein, preferably a D6 protein, includes seven transmembrane domains. In yet another embodiment, an isolated protein, preferably a D6 protein, has an amino acid sequence sufficiently homologous to the amino acid sequence of SEQ ID NO:2, or SEQ ID NO:5. In a preferred embodiment, a protein, preferably a D6 protein, has an amino acid sequence at least about 65–70%, preferably at least about 71–75%, 75–80%, even more preferably at least about 85–90%, and most preferably at least about 95% or more homologous to the amino acid sequence of SEQ ID NO:2. In another preferred embodiment, a protein, preferably a D6 protein, has an amino acid sequence at least about 65–70%, preferably at least about 75–80%, even more preferably at least about 85–90%, and most preferably at least about 90–95% or more homologous to the amino acid sequence of SEQ ID NO:5. In another embodiment, a protein, preferably a D6 protein, has the amino acid sequence of SEQ ID NO:2, or SEQ ID NO:5.

In another embodiment, the invention features fragments of the proteins having the amino acid sequence of SEQ ID NO:2 or SEQ ID NO:5, wherein the fragment comprises at least 15 contiguous amino acids of the amino acid sequence of SEQ ID NO:2 or SEQ ID NO:5.

Another embodiment of the invention features an isolated protein, preferably a D6 protein, which is encoded by a nucleic acid molecule having a nucleotide sequence at least about 80% homologous to a nucleotide sequence of SEQ ID NO:1, SEQ ID NO:3, or a complement thereof. Another embodiment of the invention features an isolated protein, preferably a D6 protein, which is encoded by a nucleic acid molecule having a nucleotide sequence at least about 90% homologous to a nucleotide sequence of SEQ ID NO:4, SEQ ID NO:6, or a complement thereof. This invention further features an isolated protein, preferably a D6 protein, which is encoded by a nucleic acid molecule having a nucleotide sequence which hybridizes under stringent hybridization conditions to a nucleic acid molecule comprising the nucleotide sequence of SEQ ID NO:1, or SEQ ID NO:3, or a complement thereof. In another embodiment, an isolated protein, preferably a D6 protein, is encoded by a nucleic acid molecule having a nucleotide sequence which hybridizes under stringent hybridization conditions to a nucleic acid molecule comprising the nucleotide sequence of SEQ ID NO:4, or SEQ ID NO:6, or a complement thereof.

The proteins of the present invention, preferably D6 proteins, or biologically active portions thereof, can be operatively linked to a non-D6 polypeptide to form fusion proteins. The invention further features antibodies that specifically bind proteins, preferably D6 proteins, such as monoclonal or polyclonal antibodies. In addition, the D6 proteins or biologically active portions thereof can be incorporated into pharmaceutical compositions, which optionally include pharmaceutically acceptable carriers.

In another aspect, the present invention provides a method for detecting D6 expression in a biological sample by contacting the biological sample with an agent capable of detecting a D6 nucleic acid molecule, protein or polypeptide such that the presence of a D6 nucleic acid molecule, protein or polypeptide is detected in the biological sample.

In another aspect, the present invention provides a method for detecting the presence of D6 activity in a biological sample by contacting the biological sample with an agent capable of detecting an indicator of D6 activity such that the presence of D6 activity is detected in the biological sample.

In another aspect, the invention provides a method for modulating D6 activity comprising contacting the cell with an agent that modulates D6 activity such that D6 activity in the cell is modulated. In one embodiment, the agent inhibits D6 activity. In another embodiment, the agent stimulates D6 activity. In one embodiment, the agent is an antibody that specifically binds to a D6 protein. In another embodiment, the agent modulates expression of D6 by modulating transcription of a D6 gene or translation of a D6 mRNA. In yet another embodiment, the agent is a nucleic acid molecule having a nucleotide sequence that is antisense to the coding strand of a D6 mRNA or a D6 gene.

In one embodiment, the methods of the present invention are used to treat a subject having a disorder characterized by aberrant D6 protein or nucleic acid expression or activity by administering an agent which is a D6 modulator to the subject. Another embodiment of the invention features a method of treating a subject having a disorder characterized by aberrant chemokine expression or activity by administering an agent which is a D6 modulator to the subject. In one embodiment, the D6 modulator is a D6 protein. In another embodiment, the D6 modulator is a D6 nucleic acid molecule. In yet another embodiment, the D6 modulator is a peptide, peptidomimetic, or other small molecule. In a preferred embodiment, the disorder characterized by aberrant D6 protein or nucleic acid expression or aberrant chemokine expression is an inflammatory or proliferative disorder.

The present invention also provides a diagnostic assay for identifying the presence or absence of a genetic alteration characterized by at least one of (i) aberrant modification or mutation of a gene encoding a D6 protein; (ii) misregulation of said gene; and (iii) aberrant post-translational modification of a D6 protein, wherein a wild-type form of said gene encodes an protein with a D6 activity.

In another aspect the invention provides a method for identifying a compound that binds to or modulates the activity of a D6 protein, by providing an indicator composition comprising a D6 protein having D6 activity, contacting the indicator composition with a test compound, and determining the effect of the test compound on D6 activity in the indicator composition to identify a compound that modulates the activity of a D6 protein.

Other features and advantages of the invention will be apparent from the following detailed description and claims.

BRIEF DESCRIPTION OF THE DRAWINGS

FIG. 1 depicts the cDNA sequence and predicted amino acid sequence of human D6. The nucleotide sequence corresponds to nucleic acids 1 to 1181 of SEQ ID NO:1. The amino acid sequence corresponds to amino acids 1 to 384 of SEQ ID NO:2.

FIG. 2 depicts the CDNA sequence and predicted amino acid sequence of murine D6. The nucleotide sequence corresponds to nucleic acids 1 to 1664 of SEQ ID NO:4. The amino acid sequence corresponds to amino acids 1 to 378 of SEQ ID NO:5.

FIG. 3 depicts an alignment of the amino acid sequences of murine D6 (Accession Number Y12879), human D6 (Accession Number Y12815), human CCR6 (Accession Number P51684) (SEQ ID NO:48), human CCR7 (Accession Number L08176) (SEQ ID NO:49), human CCR2a (Accession Number U95626) (SEQ ID NO:50), human CCR2b (Accession Number AF013958) (SEQ ID NO:51), human CCR 5 (Accession Number V89797) (SEQ ID NO:52), human CCR 1 (Accession Number AF017282) (SEQ ID NO:53), human CCR3 (Accession Number AF026535) (SEQ ID NO:54), human CCR4 (Accession Number X85740) (SEQ ID NO:55) and human CCR8 (Accession Number U45983) (SEQ ID NO:56). The seven transmembrane domains are indicated by number I-VII. In addition, the conserved cysteine residues (C) and one of the G protein docking site (bold, italisized and underlined) are highlighted.

DETAILED DESCRIPTION OF THE INVENTION

The present invention is based on the discovery of novel molecules, referred to herein as human D6 and murine D6 protein and nucleic acid molecules, which comprise a D6 family of molecules having certain conserved structural and functional features. The term "family" when referring to the protein and nucleic acid molecules of the invention is intended to mean two or more proteins or nucleic acid molecules having a common structural domain and having sufficient amino acid or nucleotide sequence homology as defined herein. Such family members can be naturally occurring and can be from either the same or different species. For example, a family can contain a first protein of human origin, as well as other, distinct proteins of human origin or alternatively, can contain homologues of non-human origin. Members of a family may also have common functional characteristics.

In one embodiment, the isolated proteins of the present invention, preferably D6 proteins, are identified based on the presence of at least two, three or four cysteine residues in the protein or corresponding nucleic acid molecule. Preferably, the D6 family member has cysteine residues which are located in the same or similar positions as cysteine residues in a D6 protein family member (and other members of the G-protein coupled heptahelical receptor family). For example, when a human D6 protein of the invention is aligned with the murine D6 family member or a G-protein coupled heptahelical receptor family member for purposes of comparison (see e.g., FIG. 3) preferred cysteine residues of the invention are those in which cysteine residues in the amino acid sequence of D6 are located in the same or similar position as the cysteine residues in other D6 family or G-protein coupled heptahelical receptor family members. As an illustrative embodiment, FIG. 3 shows cysteine residues located in the same or similar positions of the human D6 protein (corresponding to SEQ ID NO:2) and murine D6 protein (corresponding to SEQ ID NO:5) in the following locations: amino acid number 36 of human D6 and amino acid number 35 of the murine D6; amino acid number 117 of human D6 and amino acid number 116 of murine D6; amino acid number 195 of human D6 and amino acid number 194 of murine D6; and amino acid number 284 of human D6 and amino acid number 283 of murine D6.

In another embodiment of the invention, a D6 protein is identified based on the presence of at least one "G protein docking motif" in the protein or corresponding nucleic acid molecule. The term "G protein docking motif", as used herein, refers to a conserved motif of a D6 family member (or a G protein coupled heptahelical receptor family member) and is at least about 4–15 amino acid residues, preferably about 5–12 amino acid residues, and more preferably about 5–9 amino acid residues in length. A G protein docking motif preferably includes the following amino acid sequence motif: D-X-Y-L-X-I-V-H-A (SEQ ID NO:7) wherein X is any amino acid residue. In a preferred embodiment, the G protein docking motif includes the following amino acid sequence: D-$Xaa_1$-Y-L-$Xaa_2$-I-V-H-A, wherein $Xaa_1$ is lysine (K); and $Xaa_2$ is glutamic acid (E). In one embodiment, a D6 protein includes a G protein docking motif having at least about 65%, preferably at least 70 to about 75%, and more preferably about 80% amino acid sequence homology to a G protein docking motif amino acid sequence amino acid residues 141–149 of SEQ ID NO:2 or amino acid residues 140–148 of SEQ OD NO:5. In a preferred embodiment, a D6 protein has the G protein docking motif of amino acid residues 141–149 of SEQ ID NO:2 or amino acid residues 140–148 of SEQ ID NO:5.

In another embodiment of the invention, a D6 protein is identified based on the presence of a second G protein docking motif. The second G protein docking motif preferably includes the following amino acid sequence motif: R-X-Y-L-K (SEQ ID NO:8) wherein X is any amino acid residue. In a preferred embodiment, the second G protein docking motif includes the the following amino acid sequence: R-$Xaa_1$-Y-L-K, wherein $Xaa_1$ is arginine (R) or glutamine (Q). In one embodiment, a D6 protein includes a second G protein docking motif having at least about 65%, preferably at least 70 to about 75%, and more preferably about 80% amino acid sequence homology to a G protein docking motif amino acid sequence amino acid residues 320–324 of SEQ ID NO:2 or amino acid residues 319–323 of SEQ ID NO:5. In a preferred embodiment, a D6 protein has the G protein docking motif of amino acid residues 320–324 of SEQ ID NO:2 or amino acid residues 319–323 of SEQ ID NO:5.

In yet another embodiment of the invention, a D6 protein has at least four, five, six or seven transmembrane domains. As used herein, the term "transmembrane domain" refers to a structural amino acid motif which includes a hydrophobic helix that spans the plasma membrane. A transmembrane domain preferably includes a series of hydrophobic residues, such as leucine, valine, and tyrosine residues. For example, a D6 protein contains transmembrane domains containing amino acid residues 67–92, amino acid residues 103–124, amino acid residues 139–159, amino acid residues 178–203, amino acid residues 228–249, amino acid residues 269–292, and/or amino acid residues 309–331 of SEQ ID NO:2. In another embodiment, a D6 protein contains transmembrane domains containing amino acid residues 66–91, amino acid residues 102–123, amino acid residues 138–158, amino acid residues 177–202, amino acid residues 227–248, amino acid residues 268–291, and/or amino acid residues 308–330 of SEQ ID NO:5.

Isolated proteins of the present invention, preferably D6 proteins, have an amino acid sequence sufficiently homologous to the amino acid sequence of SEQ ID NO:2, or SEQ ID NO:5. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains and/or a common functional activity. For example, amino acid or nucleotide sequences which share common structural domains have at least about 40% homology, preferably 50% homology, more preferably 60%–70% homology across the amino acid sequences of the domains and contain at least one, preferably two, more preferably three, and even more preferably four, five or six structural domains, are defined herein as sufficiently homologous. Furthermore, amino acid or nucleotide sequences which share at least 40%, preferably 50%, more preferably 60, 70, or 80% homology and share a common functional activity are defined herein as sufficiently homologous.

As used interchangeably herein, a "D6 activity", "biological activity of D6" or "functional activity of D6", refers to an activity exerted by a D6 protein, polypeptide or nucleic acid molecule on a D6 responsive cell as determined in vivo, or in vitro, according to standard techniques. In one embodiment, a D6 activity is a direct activity, such as an association with a D6-target molecule. As used herein, a "target molecule" is a molecule with which a D6 protein binds or interacts in nature, such that D6-mediated function is achieved. A D6 target molecule can be a non-D6 molecule or a D6 protein or polypeptide of the present invention. In an exemplary embodiment, a D6 target molecule is a soluble protein molecule (e.g., a "D6 binding partner" or a "D6 substrate"). In such an exemplary embodiment, a D6 binding partner can be a soluble. non-D6 protein or a second D protein molecule of the present invention. Alternatively, a D6 activity is an indirect activity, such as a cellular signaling activity mediated by interaction of the D6 protein with a second protein (e.g., a D6 ligand).

In a preferred embodiment, a D6 activity is at least one or more of the following activities: (i) interaction of a D6 protein on the cell surface with a second non-D6 protein molecule on the surface of the same cell; (ii) interaction of a D6 protein on the cell surface with a second non-D6 protein molecule on the surface of a different cell; (iii) complex formation between a membrane-bound D6 protein and a chemokine e.g., MIP-1α or JE; (iv) interaction of a D6 protein with an intracellular protein including protein kinases or cytoskeletal proteins; and (v) stimulation of cell migration. In another preferred embodiment, a D6 activity is at least one or more of the following activities: (i) modulation of cellular signal transduction, either in vitro or in vivo; (ii) modulation of pro-inflammatory function of chemokines; (iii) modulation of cellular signal transduction; (iv) regulation of cellular proliferation; (v) regulation of cellular migration; and (vi) modulation of chemokine-stimulated chemotaxis.

Accordingly, another embodiment of the invention features isolated D6 proteins and polypeptides having a D6 activity. Preferred D6 proteins have at least two, three, four conserved cysteine-rich residues and a D6 activity. In another preferred embodiment, the D6 protein has at least two conserved cysteine residues, at least one G protein docking motif, and a D6 activity. In another preferred embodiment, the D6 protein has at least two conserved cysteine residues, at least one G protein docking motif, is membrane bound and has a D6 activity. In still another preferred embodiment, a D6 protein has at least two conserved cysteine residues, at least one G protein docking motif, a D6 activity, and an amino acid sequence sufficiently homologous to an amino acid sequence of SEQ ID NO:2, or SEQ ID NO:5.

In a particularly preferred embodiment, the D6 protein and nucleic acid molecules of the present invention are human or murine D6 molecules. A murine D6 cDNA molecule was obtained from murine homogenized spleen as described in Example 1 and was used to isolate human D6 cDNA molecules (also described in Example 1). The nucleotide sequences of the isolated human D6 cDNA and the predicted amino acid sequence of the human D6 protein are shown in FIG. 1 and in SEQ ID NOs:1 and 2, respectively. In addition, the nucleotide sequence corresponding to the coding region of the human D6 cDNA is represented as SEQ ID NO:3. The nucleotide sequences of the isolated murine D6 cDNA and the predicted amino acid sequence of the murine D6 protein are shown in FIG. 2 and in SEQ ID NOs:4 and 5, respectively. In addition, the nucleotide sequence corresponding to the coding region of the murine D6 cDNA is represented as SEQ ID NO:6.

The human D6 cDNA, which is approximately 1181 nucleotides in length, encodes a protein which is approximately 384 amino acid residues in length. The human D6 protein contains four conserved cysteine residues and two G protein docking motifs. A conserved cysteine residue can be found at least, for example, at about amino acids 36, 117, 195 and 284 of SEQ ID NO:2. Moreover, a G protein docking motif can be found, for example, from about amino acids 141–149 of SEQ ID NO:2 (shown separately as SEQ ID NO:7) and a second G protein docking motif can be found, for example, from about amino acids 320–324 of SEQ ID NO:2 (shown separately as SEQ ID NO:8). The human D6 protein is a membrane bound protein which contains seven transmembrane domains at about amino acids 67–92, 103–124, 139–159, 178–203, 228–249, 269–292 and 309–331 of SEQ ID NO:2.

The murine D6 cDNA, which is approximately 1664 nucleotides in length, encodes a protein which is approximately 378 amino acid residues in length. The murine D6 protein contains four conserved cysteine residues and two G protein docking motifs. A conserved cysteine residue of murine D6 can be found at least, for example, at amino acid 35, 116, 194 and 283 of SEQ ID NO:5. Moreover, a G protein docking motif can be found, for example, from about amino acids 140–148 of SEQ ID NO:5 (shown separately as SEQ ID NO:7) and a second G protein docking motif can be found, for example, from about amino acids 319–323 of SEQ ID NO:5 (shown separately as SEQ ID NO:8). The murine D6 protein is a membrane bound protein which contains seven transmembrane domains at about amino acids 66–91, 102–123, 138–158, 177–202, 227–248, 268–291 and 308–330 of SEQ ID NO:5.

An alignment of the amino acid sequences of human D6 (Genbank™ Accession No. Y12815) and murine D6 (Genbank™ Accession Number Y12879) with human CCR6 (Accession Number P51684) (SEQ ID NO:48), human CCR7 (Accession Number L08176) (SEQ ID NO:49), human CCR2a (Accession Number U95626) (SEQ ID NO:50), human CCR2b (Accession Number AF013958) (SEQ ID NO:51), human CCR 5 (Accession Number V89797) (SEQ ID NO:52), human CCR 1 (Accession Number AF017282) (SEQ ID NO:53), human CCR3 (Accession Number AF026535) (SEQ ID NO:54), human CCR4 (Accession Number X85740) (SEQ ID NO:55) and human CCR8 (Accession Number U45983) (SEQ ID NO:56) is shown in FIG. 3. The alignment was generated using MegAlign™ sequence alignment software. The initial pairwise alignment step was performed using a Wilbur-Lipmann algorithm with a K-tuple of 1, a GAP penalty of 3, a window of 5, and diagonals saved set to=4. The multiple alignment step was performed using the Clustal algorithm with a PAM 250 residue weight Table, a GAP penalty of 10, and a GAP length penalty of 10.)

Various aspects of the invention are described in further detail in the following subsections:

I. Isolated Nucleic Acid Molecules

One aspect of the invention pertains to isolated nucleic acid molecules which encode D6 proteins or biologically active portions thereof, as well as nucleic acid fragments sufficient for use as hybridization probes to identify D6 encoding nucleic acids (e.g., D6 mRNA) and fragments for use as PCR primers for the amplification or mutation of D6 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated D6 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:4, or SEQ ID NO:6 or a portion thereof, can be isolated using standard molecular biology techniques and the sequence information provided herein. Using all or a portion of the nucleic acid sequence of SEQ ID NO:1, SEQ ID NO:3, SEQ ID NO:4, or SEQ ID NO:6 as a hybridization probe, D6 nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, SEQ ID NO:3, SEQ ID NO:4, or SEQ ID NO:6 can be isolated by the polymerase chain reaction (PCR) using synthetic oligonucleotide primers designed based upon the sequence of SEQ ID NO:1, SEQ ID NO:3, SEQ ID NO:4, or SEQ ID NO:6.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to D6 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human D6 cDNA. This cDNA comprises sequences encoding the human D6 protein (i.e., "the coding region", from nucleotides 12–1167), as well as 5' untranslated sequences (nucleotides 1 to 11) and 3' untranslated sequences (nucleotides1168–1181). Alternatively, the nucleic acid molecule can comprise only the coding region of SEQ ID NO:1 (e.g., nucleotides 12–1167, corresponding to SEQ ID NO:3).

In another preferred embodiment, an isolated nucleic acid molecule of the invention comprises the nucleotide sequence shown in SEQ ID NO:4. The sequence of SEQ ID NO:4 corresponds to the murine D6 cDNA. This cDNA comprises sequences encoding the murine D6 protein (i.e., "the coding region", from nucleotides 192–1326), as well as 5' untranslated sequences (nucleotides 1–191) and 3' untranslated sequences (nucleotides 1327–1664). Alternatively, the nucleic acid molecule can comprise only the coding region of SEQ ID NO:4 (e.g., nucleotides 192–1326, corresponding to SEQ ID NO:6).

In another preferred embodiment, an isolated nucleic acid molecule of the invention comprises a nucleic acid molecule which is a complement of the nucleotide sequence shown in SEQ ID NO:1, SEQ ID NO:3, SEQ ID NO:4, or SEQ ID 6, or a portion of any of these nucleotide sequences. A nucleic acid molecule which is complementary to the nucleotide sequence shown in SEQ ID NO:1, SEQ ID NO:3, SEQ ID NO:4, or SEQ ID NO:6 is one which is sufficiently complementary to the nucleotide sequence shown in SEQ ID NO:1, SEQ ID NO:3, SEQ ID NO:4, or SEQ ID NO:6 such that it can hybridize to the nucleotide sequence shown in SEQ ID NO:1, SEQ ID NO:3, SEQ ID NO:4, or SEQ ID NO:6, thereby forming a stable duplex.

In still another preferred embodiment, an isolated nucleic acid molecule of the present invention comprises a nucleotide sequence which is at least about 60–65%, more preferably at least about 70–75%, even more preferably at least about, 78–85%, and most preferably at least about 90–95% or more homologous to the nucleotide sequences show in SEQ ID NO:1, SEQ ID NO:3, or a portion of either of these nucleotide sequences larger than 215 bp. In yet another embodiment, an isolated nucleic acid molecule of the present invention comprises a nucleotide sequence which is at least about 60–65%, more preferably at least about 70–75%, even more preferably at least about, 80–85%, and most preferably at least about 90–95% or more homologous to the nucleotide sequences show in SEQ ID NO:4, SEQ ID NO:6, or a portion of either of these nucleotide sequences larger than 117 bp.

Moreover, the nucleic acid molecule of the invention can comprise only a portion of the nucleic acid sequence of SEQ ID NO:1, or SEQ ID NO:4, for example a fragment which can be used as a probe or primer or a fragment encoding a biologically active portion of a D6 protein. The nucleotide sequence determined from the cloning of the murine and human D6 genes allows for the generation of probes and primers designed for use in identifying and/or cloning D6 homologues in other cell types, e.g., from other tissues, as well as D6 homologues from other mammals. The probe/primer typically comprises a substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense sequence of SEQ ID NO:1, SEQ ID NO:3, SEQ ID NO:4, or SEQ ID NO:6, of an antisense sequence of SEQ ID NO:1, SEQ ID NO:3, SEQ ID NO:4, or SEQ ID NO:6, or of a naturally occurring mutant of SEQ ID NO:1, SEQ ID NO:3, SEQ ID NO:4, or SEQ ID NO:6. In an exemplary embodiment, a nucleic acid molecule of the present invention comprises a nucleotide sequence which hybridizes under stringent hybridization conditions to a nucleic acid molecule comprising nucleotides 1–69, 70–858, or 1173–1181 of SEQ ID NO:1 or to a nucleic acid molecule comprising nucleotides 1–117 or 1395–1664 of SEQ ID NO:4.

Probes based on the huamn and murine D6 nucleotide sequence can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a D6 protein, such as by measuring a level of a D6encoding nucleic acid in a sample of cells from a subject e.g., detecting D6 MRNA levels or determining whether a genomic D6 gene has been mutated or deleted.

A nucleic acid fragment encoding a "biologically active portion of a D6 protein" can be prepared by isolating a portion of SEQ ID NO:1, SEQ ID NO:3, SEQ ID NO:4, or SEQ ID NO:6 which encodes a polypeptide having a D6 biological activity (the biological activities of the D6 protein includes biological activities attributed to the G protein coupled heptahelical receptor family of proteins), expressing the encoded portion of the D6 protein (e.g., by recombinant expression in vitro) and assessing the activity of the encoded portion of the D6 protein.

The invention fuirther encompasses nucleic acid molecules that differ from the nucleotide sequence shown in SEQ ID NO:1, SEQ ID NO:3, SEQ ID NO:4, or SEQ ID NO:6 due to degeneracy of the genetic code and thus encode the same D6 proteins as those encoded by the nucleotide sequence shown in SEQ ID NO:1, SEQ ID NO:3, SEQ ID NO:4, or SEQ ID NO:6. In another embodiment, an isolated nucleic acid molecule of the invention has a nucleotide sequence encoding a protein having an amino acid sequence shown in SEQ ID NO:2 or SEQ ID NO:5.

In addition to the human D6 nucleotide sequences shown in SEQ ID NO:1 and the murine D6 nucleotide sequence shown in SEQ ID NO:4, respectively, it will be appreciated by those skilled in the art that DNA sequence polymorphisms that lead to changes in the amino acid sequences of the D6 proteins may exist within a population (e.g., other mammalian populations). Such genetic polymorphism in the D6 genes may exist among individuals within a population due to natural allelic variation. As used herein, the terms "gene" and "recombinant gene" refer to nucleic acid molecules comprising an open reading frame encoding a D6 protein, preferably a mammalian D6 protein. Such natural allelic variations can typically result in 1–5% variance in the nucleotide sequence of a D6 gene. Any and all such nucleotide variations and resulting amino acid polymorphisms in D6 genes that are the result of natural allelic variation and that do not alter the functional activity of a D6 protein are intended to be within the scope of the invention.

Moreover, nucleic acid molecules encoding D6 proteins from other species, and thus which have a nucleotide sequence which differs from the human sequence of SEQ ID NO:1 and the murine sequence of SEQ ID NO:4 are intended to be within the scope of the invention.

Nucleic acid molecules corresponding to natural allelic variants and homologues of the human or murine D6 cDNA of the invention can be isolated based on their homology to the human D6 or murine D6 nucleic acids disclosed herein using the human or murine cDNA, or a portion thereof, as a hybridization probe according to standard hybridization techniques under stringent hybridization conditions.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1, SEQ ID NO:3, SEQ ID NO:4, or SEQ ID NO:6. In another embodiment, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1 or SEQ ID NO:4 corresponds to a naturally-occurring nucleic acid molecule. As used herein, a "naturally-occurring" nucleic acid molecule refers to an RNA or DNA molecule having a nucleotide sequence that occurs in nature (eg., encodes a natural protein).

In addition to naturally-occurring allelic variants of the D6 sequences that may exist in the population, the skilled artisan will further appreciate that changes can be introduced by mutation into the nucleotide sequences of SEQ ID NO:1, or SEQ ID NO:4, thereby leading to changes in the amino acid sequence of the encoded D6 proteins, without altering the functional ability of the D6 proteins. For example, nucleotide substitutions leading to amino acid substitutions at "non-essential" amino acid residues can be made in the sequence of SEQ ID NO:1, or SEQ ID NO:4. A "non-essential" amino acid residue is a residue that can be altered from the wild-type sequence of D6 (e.g., the sequence of SEQ ID NO:2 or SEQ ID NO:5) without altering the biological activity, whereas an "essential" amino acid residue is required for biological activity. For example, amino acid residues that are conserved among the D6 proteins of the present invention, are predicted to be particularly unamenable to alteration. Furthermore, amino acid residues that are conserved between D6 protein and other proteins having the conserved cysteine residues are not likely to be amenable to alteration.

Accordingly, another aspect of the invention pertains to nucleic acid molecules encoding D6 proteins that contain changes in amino acid residues that are not essential for activity. Such D6 proteins differ in amino acid sequence from SEQ ID NO:2 or SEQ ID NO:5 yet retain biological activity. In one embodiment, the isolated nucleic acid molecule comprises a nucleotide sequence encoding a protein, wherein the protein comprises an amino acid sequence at least about 60% homologous to the amino acid sequence of SEQ ID NO:2, or SEQ ID NO:5. Preferably, the protein encoded by the nucleic acid molecule is at least about 65–70%, more preferably at least about 75–80%, even more preferably at least about 80–90%, and most preferably at least about 90–95% homologous to SEQ ID NO:2, or SEQ ID NO:5.

An isolated nucleic acid molecule encoding a D6 protein homologous to the protein of SEQ ID NO:2 or SEQ ID NO:5, respectively, can be created by introducing one or more nucleotide substitutions, additions or deletions into the nucleotide sequence of SEQ ID NO:1, SEQ ID NO:3, SEQ ID NO:4, or SEQ ID NO:6, such that one or more amino acid substitutions, additions or deletions are introduced into the encoded protein. Mutations can be introduced into SEQ ID NO:1, SEQ ID NO:3, SEQ ID NO:4, or SEQ ID NO:6 by standard techniques, such as site-directed mutagenesis and PCR-mediated mutagenesis. Preferably, conservative amino acid substitutions are made at one or more predicted nonessential amino acid residues. A "iconservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a D6 protein is preferably replaced with another amino acid residue from the same side chain family. Alternatively, in another embodiment, mutations can be introduced randomly along all or part of a D6 coding sequence, such as by saturation mutagenesis, and the resultant mutants can be screened for D6 biological activity to identify mutants that retain activity. Following mutagenesis of SEQ ID NO:1, SEQ ID NO:3, SEQ ID NO:4, or SEQ ID NO:6, the encoded protein can be expressed recombinantly and the activity of the protein can be determined.

In a preferred embodiment, a mutant D6 protein can be assayed for the ability to: (i) modulation of cellular signal transduction, either in vitro or in vivo; (ii) modulation of pro-inflammatory function of chemokines; (iii) modulation of cellular signal transduction; (iv) regulation of cellular proliferation; (v) regulation of cellular migration; and (vi) modulation of chemokine-stimulated chemotaxis.

In addition to the nucleic acid molecules encoding D6 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire D6 coding strand, or to only a portion thereof. In one embodiment, an antisense nucleic acid molecule is antisense to a "coding region" of the coding strand of a nucleotide sequence encoding D6. The term "coding region" refers to the region of the nucleotide sequence comprising codons which are translated into amino acid residues (e.g., the coding region of human D6 corresponds to SEQ ID NO:3 and the coding region of murine D6 corresponds to SEQ ID NO:6). In another embodiment, the antisense nucleic acid molecule is antisense to a "noncoding region" of the coding strand of a nucleotide sequence encoding D6. The term "noncoding region" refers to 5' and 3' sequences which flank the coding region that are not translated into amino acids (i.e., also referred to as 5' and 3' untranslated regions).

Given the coding strand sequences encoding D6 disclosed herein (e.g., SEQ ID NO:3 or SEQ ID NO:6), antisense nucleic acids of the invention can be designed according to the rules of Watson and Crick base pairing. The antisense nucleic acid molecule can be complementary to the entire coding region of D6 mRNA, but more preferably is an oligonucleotide which is antisense to only a portion of the coding or noncoding region of D6 mRNA. For example, the antisense oligonucleotide can be complementary to the region surrounding the translation start site of D6 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a D6 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave D6 MRNA transcripts to thereby inhibit translation of D6 MRNA. A ribozyme having specificity for a D6-encoding nucleic acid can be designed based upon the nucleotide sequence of a D6 cDNA disclosed herein (i.e., SEQ ID NO:1, SEQ ID NO:3, SEQ ID NO:4, or SEQ ID NO:6). For example, a derivative of a Tetrahymena L-19 IVS RNA can be constructed in which the nucleotide sequence of the active site is complementary to the nucleotide sequence to be cleaved in a D6-encoding mRNA. See, e.g., Cech et al. U.S. Pat. No. 4,987,071; and Cech et al. U.S. Pat. No. 5,116,742. Alternatively, D6 mRNA can be used to select a catalytic RNA having a specific ribonuclease activity from a pool of RNA molecules. See, e.g., Bartel, D. and Szostak, J. W. (1993) *Science* 261:1411–1418.

Alternatively, D6 gene expression can be inhibited by targeting nucleotide sequences complementary to the regulatory region of the D6 (e.g., the D6 promoter and/or enhancer) to form triple helical structures that prevent tanscription of the D6 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the D6 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al PNAS 93: 14670–675.

PNAs of D6 nucleic acid molecules can be used for therapeutic and diagnostic applications. For example, PNAs can be used as antisense or antigene agents for sequence-specific modulation of gene expression by, for example, inducing transcription or translation arrest or inhibiting replication. PNAs of D6 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of D6 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of D6 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric moleclues can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci.* US. 86:6553–6556; Lemaitre et al. (1987) *Proc. Natl. Acad. Sci.* USA 84:648–652; PCT Publication No. WO88/09810, published Dec. 15, 1988) or the blood-brain barrier (see, e.g., PCT Publication No. WO89/10134, published Apr. 25, 1988). In addition, oligonucleotides can be modified with hybridization-triggered cleavage agents (See, e.g., Krol et al. (1988) *BioTechniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated D6 Proteins and Anti-D6 Antibodies

One aspect of the invention pertains to isolated D6 proteins, and biologically active portions thereof, as well as polypeptide fragments suitable for use as immunogens to raise anti-D6 antibodies. In one embodiment, native D6 proteins can be isolated from cells or tissue sources by an appropriate purification scheme using standard protein purification techniques. In another embodiment, D6 proteins are produced by recombinant DNA techniques. Alternative to recombinant expression, a D6 protein or polypeptide can be synthesized chemically using standard peptide synthesis techniques.

An "isolated" or "purified" protein or biologically active portion thereof is substantially free of cellular material or other contaminating proteins from the cell or tissue source from which the D6 protein is derived, or substantially free from chemical precursors or other chemicals when chemically synthesized. The language "substantially free of cellular material" includes preparations of D6 protein in which the protein is separated from cellular components of the cells from which it is isolated or recombinantly produced. In one embodiment, the language "substantially free of cellular material" includes preparations of D6 protein having less than about 30% (by dry weight) of non-D6 protein (also referred to herein as a "contaminating protein"), more preferably less than about 20% of non-D6 protein, still more preferably less than about 10% of non-D6 protein, and most preferably less than about 5% non-D6 protein. When the D6 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of D6 protein in which the protein is separated from chemical precursors or other chemicals which are involved in the synthesis of the protein. In one embodiment, the language "substantially free of chemical precursors or other chemicals" includes preparations of D6 protein having less than about 30% (by dry weight) of chemical precursors or non-D6 chemicals, more preferably less than about 20% chemical precursors or non-D6 chemicals, still more preferably less than about 10% chemical precursors or non-D6 chemicals, and most preferably less than about 5% chemical precursors or non-D6 chemicals.

Biologically active portions of a D6 protein include peptides comprising amino acid sequences sufficiently homologous to or derived from the amino acid sequence of the D6 protein, e.g., the amino acid sequence shown in SEQ ID NO:2 or SEQ ID NO:5, which include less amino acids than the fill length D6 proteins, and exhibit at least one activity of a D6 protein. Typically, biologically active portions comprise a domain or motif with at least one activity of the D6 protein. A biologically active portion of a D6 protein can be a polypeptide which is, for example, 10, 25, 50, 100 or more amino acids in length.

In one embodiment, a biologically active portion of a D6 protein comprises at least one, two, three or four conserved cysteine residues. In another embodiment, a biologically active portion of a D6 protein comprises at least one conserved cysteine residue and at least one G protein docking motif.

It is to be understood that a preferred biologically active portion of a D6 protein of the present invention may contain at least one of the above-identified structural domains. Another preferred biologically active portion of a D6 protein may contain at least two of the above-identified structural domains. Another more preferred biologically active portion of a D6 protein may contain at least three or more of the above-identified structural domains.

Moreover, other biologically active portions, in which other regions of the protein are deleted, can be prepared by recombinant techniques and evaluated for one or more of the functional activities of a native D6 protein.

In a preferred embodiment, the D6 protein has an amino acid sequence shown in SEQ ID NO:2 or SEQ ID NO:5. In other embodiments, the D6 protein is substantially homologous to SEQ ID NO:2 or SEQ ID NO:5, and retains the functional activity of the protein of SEQ ID NO:2 or SEQ ID NO:5, yet differs in amino acid sequence due to natural allelic variation or mutagenesis, as described in detail in subsection I above. Accordingly, in another embodiment, the D6 protein is a protein which comprises an amino acid sequence at least about 60% homologous to the amino acid sequence of SEQ ID NO:2 or SEQ ID NO:5 and preferably retains a functional activity of the D6 protein of SEQ ID NO:2 or SEQ ID NO:5. Preferably, the protein is at least about 70% homologous to SEQ ID NO:2 or SEQ ID NO:5, more preferably at least about 75–80% homologous to SEQ ID NO:2 or SEQ ID NO:5, even more preferably at least about 85% homologous to SEQ ID NO:2 or SEQ ID NO:5, and most preferably at least about 90–95% or more homologous to SEQ ID NO:2 or SEQ ID NO:5.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100). The determination of percent homology between two sequences can be accomplished using a mathematical algorithim. A preferred, non-limiting example of a mathematical algorithim utilized for the comparison of two sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs of Altschul, et al. (1990) J. Mol. Biol. 215:403–10. BLAST nucleotide searches can be performed with the NBLAST program, score=100, wordlength=12 to obtain nucleotide sequences homologous to D6 nucleic acid molecules of the invention. BLAST protein searches can be performed with the XBLAST program, score=50, wordlength=3 to obtain amino acid sequences homologous to D6 protein molecules of the invention. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The invention also provides D6 chimeric or fusion proteins. As used herein, a D6 "chimeric protein" or "fusion protein" comprises a D6 polypeptide operatively linked to a non-D6 polypeptide. A "D6 polypeptide" refers to a polypeptide having an amino acid sequence corresponding to D6, whereas a "non-D6 polypeptide" refers to a polypeptide having an amino acid sequence corresponding to a protein which is not substantially homologous to the D6 protein, e.g., a protein which is different from the D6 protein and which is derived from the same or a different organism. Within a D6 fusion protein the D6 polypeptide can correspond to all or a portion of a D6 protein. In a preferred embodiment, a D6 fusion protein comprises at least one biologically active portion of a D6 protein In another preferred embodiment, a D6 fusion protein comprises at least two biologically active portions of a D6 protein. In another preferred embodiment, a D6 fusion protein comprises at least three biologically active portions of a D6 protein. Within the fusion protein, the term "operatively linked" is intended to indicate that the D6 polypeptide and the non-D6 polypeptide are fused in-frame to each other. The non-D6 polypeptide can be fused to the N-terminus or C-terminus of the D6 polypeptide.

For example, in one embodiment, the fusion protein is a GST-D6 fusion protein in which the D6 sequences are fused to the C-terminus of the GST sequences. Such fusion proteins can facilitate the purification of recombinant D6. In another embodiment, the fusion protein is a D6 protein containing a heterologous signal sequence at its N-terminus. In certain host cells (e.g., mammalian host cells), expression and/or secretion of D6 can be increased through use of a heterologous signal sequence.

In yet another embodiment, the fusion protein is a D6-immunoglobulin fusion protein in which the D6 sequences comprising primarily the D6 cysteine-rich domains are fused to sequences derived from a member of the immunoglobulin protein family. Soluble derivatives have also been made of cell surface glycoproteins in the immunoglobulin gene superfamily consisting of an extracellular domain of the cell surface glycoprotein fused to an immunoglobulin constant (Fc) region (see e.g., Capon, D. J. et al. (1989) *Nature* 337:525–531 and Capon U.S. Pat. Nos. 5,116,964 and 5,428,130 [CD4-IgG1 constructs]; Linsley, P. S. et al. (1991) *J. Exp. Med.* 173:721–730 [a CD28-IgG1 construct and a B7-1-IgG1 construct]; and Linsley, P. S. et al. (1991) *J. Exp. Med.* 174:561–569 and U.S. Pat. No. 5,434,131 [a CTLA4-IgG1]). Such fusion proteins have proven useful for modulating receptor-ligand interactions. Soluble derivatives of cell surface proteins of the tumor necrosis factor receptor (TNFR) superfamily proteins have been made consisting of an extracellular domain of the cell surface receptor fused to an imnmunoglobulin constant (Fc) region (see for example Moreland et al. (1997) N. Engl. J. Med. 337(3):141–147; van der Poll et al. (1997) Blood 89(10):3727–3734; and Ammann et al. (1997) J. Clin. Invest. 99(7):1699–1703).

The D6-immunoglobulin fusion proteins of the invention can be incorporated into pharmaceutical compositions and administered to a subject to inhibit an interaction between a D6 ligand and a D6 receptor on the surface of a cell, to thereby suppress D6-mediated signal transduction in vivo. The D6-immunoglobulin fusion proteins can be used to affect the bioavailability of a D6 cognate receptor. Inhibition of the D6 ligand/D6 interaction may be useful therapeutically for both the treatment of inflammatory or proliferative disorders, as well as modulating (e.g., promoting or inhibiting) developmental responses, cell adhesion, and/or cell fate. Moreover, the D6-immunoglobulin fusion proteins of the invention can be used as immunogens to produce anti-D6 antibodies in a subject, to purify D6 ligands and in screening assays to identify molecules which inhibit the interaction of D6 with a D6 ligand.

Preferably, a D6 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A D6-encoding nucleic acid can be cloned into such an expression vector such that the fusion moiety is linked in-frame to the D6 protein.

The present invention also pertains to variants of the D6 proteins which function as either D6 agonists (mimetics) or as D6 antagonists. Variants of the D6 proteins can be generated by mutagenesis, e.g., discrete point mutation or truncation of a D6 protein. An agonist of the D6 proteins can retain substantially the same, or a subset, of the biological activities of the naturally occurring form of a D6 protein. An antagonist of a D6 protein can inhibit one or more of the activities of the naturally occurring form of the D6 protein by, for example, competitively binding to a downstream or upstream member of a cellular signaling cascade which includes the D6 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the D6 protein.

In one embodiment, variants of a D6 protein which function as either D6 agonists (mimetics) or as D6 antagonists can be identified by screening combinatorial libraries of mutants, e.g., truncation mutants, of a D6 protein for D6 protein agonist or antagonist activity. In one embodiment, a variegated library of D6 variants is generated by combinatorial mutagenesis at the nucleic acid level and is encoded by a variegated gene library. A variegated library of D6 variants can be produced by, for example, enzymatically ligating a mixture of synthetic oligonucleotides into gene sequences such that a degenerate set of potential D6 sequences is expressible as individual polypeptides, or alternatively, as a set of larger fusion proteins (e.g., for phage display) containing the set of D6 sequences therein. There are a variety of methods which can be used to produce libraries of potential D6 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential D6 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a D6 protein coding sequence can be used to generate a variegated population of D6 fragments for screening and subsequent selection of variants of a D6 protein. In one embodiment, a library of coding sequence fragments can be generated by treating a double stranded PCR fragment of a D6 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the D6 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of D6 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify D6 variants (Arkin and Yourvan (1992) *PNAS* 89:7811–7815; Delgrave et al. (1993) *Protein Engineering* 6(3):327–331).

In one embodiment, cell based assays can be exploited to analyze a variegated D6 library. For example, a library of expression vectors can be transfected into a cell line which ordinarily responds to a particular ligand, e.g., a cytokine, in a D6-dependent manner. The transfected cells are then contacted with the ligand and the effect of expression of the mutant on signaling by the ligand can be detected, e.g., by measuring NF-κB activity or cell survival. Plasmid DNA can then be recovered from the cells which score for inhibition, or alternatively, potentiation of cytokine induction, and the individual clones further characterized.

An isolated D6 protein, or a portion or fragment thereof, can be used as an immunogen to generate antibodies that bind D6 using standard techniques for polyclonal and monoclonal antibody preparation. A fill-length D6 protein can be used or, alternatively, the invention provides antigenic peptide fragments of D6 for use as immunogens. The antigenic peptide of D6 comprises at least 8 amino acid residues of the amino acid sequence shown in SEQ ID NO:2 or SEQ ID NO:5 and encompasses an epitope of D6 such that an antibody raised against the peptide forms a specific immune complex with D6. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of D6 that are located on the surface of the protein, e.g., hydrophilic regions.

A D6 immunogen typically is used to prepare antibodies by immunizing a suitable subject, (e.g., rabbit, goat, mouse or other mammal) with the immunogen. An appropriate immunogenic preparation can contain, for example, recombinantly expressed D6 protein or a chemically synthesized D6 polypeptide. The preparation can further include an adjuvant, such as Freund's complete or incomplete adjuvant, or similar immunostimulatory agent. Immunization of a suitable subject with an immunogenic D6 preparation induces a polyclonal anti-D6 antibody response.

Accordingly, another aspect of the invention pertains to anti-D6 antibodies. The term "antibody" as used herein refers to immunoglobulin molecules and immunologically active portions of immunoglobulin molecules, i.e., molecules that contain an antigen binding site which specifically binds (immunoreacts with) an antigen, such as D6. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind D6. The term "monoclonal antibody" or "monoclonal antibody composition", as used herein, refers to a population of antibody molecules that contain only one species of an antigen binding site capable of immunoreacting with a particular epitope of D6. A monoclonal antibody composition thus typically displays a single binding affinity for a particular D6 protein with which it immunoreacts.

Polyclonal anti-D6 antibodies can be prepared as described above by immunizing a suitable subject with a D6 immunogen. The anti-D6 antibody titer in the immunized subject can be monitored over time by standard techniques, such as with an enzyme linked immunosorbent assay (ELISA) using immobilized D6. If desired, the antibody molecules directed against D6 can be isolated from the mammal (e.g., from the blood) and further purified by well known techniques, such as protein A chromatography to obtain the IgG fraction. At an appropriate tirne after immunization, e.g., when the anti-D6 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) PNAS 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a D6 imnmunogen as described above, and the culture supernatants of the resulting hybridoma cells are screened to identify a hybridoma producing a monoclonal antibody that binds D6.

Any of the many well known protocols used for fusing lymphocytes and immortalized cell lines can be applied for the purpose of generating an anti-D6 monoclonal antibody (see, e.g., G. Galfre et al. (1977) *Nature* 266:55052; Gefter et al. *Somatic Cell Genet.*, cited supra; Lerner, *Yale J Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind D6, e.g., using a standard ELISA assay.

Alternative to preparing monoclonal antibody-secreting hybridomas, a monoclonal anti-D6 antibody can be identified and isolated by screening a recombinant combinatorial immunoglobulin library (e.g., an antibody phage display library) with D6 to thereby isolate imunoglobulin library members that bind D6. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al.

U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

Additionally, recombinant anti-D6 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,021; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1 988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-D6 antibody (e.g., monoclonal antibody) can be used to isolate D6 by standard techniques, such as affinity chromatography or immunoprecipitation. An anti-D6 antibody can facilitate the purification of natural D6 from cells and of recombinantly produced D6 expressed in host cells. Moreover, an anti-D6 antibody can be used to detect D6 protein (e.g., in a cellular lysate or cell supernatant) in order to evaluate the abundance and pattern of expression of the D45 protein. Anti-D6 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding D6 (or a portion thereof). As used herein, the term "vector" refers to a nucleic acid molecule capable of transporting another nucleic acid to which it has been linked. One type of vector is a "plasmid", which refers to a circular double stranded DNA, loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., D6 proteins, mutant forms of D6, fusion proteins, etc.).

The recombinant expression vectors of the invention can be designed for expression of D6 in prokaryotic or eukaryotic cells. For example, D6 can be expressed in bacterial cells such as *E coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Purified fusion proteins can be utilized in D6 activity assays, in D6 ligand binding (e.g., direct assays or competitive assays described in detail below), to generate antibodies specific for D6 proteins, as examples. In a preferred embodiment, a D6 fusion expressed in a retroviral expression vector of the present invention can be utilized to infect bone marrow cells which are subsequently transplanted into irradiated recipients. The pathology of the subject recipient is then examined after sufficient time has passed (e.g six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET11d vector relies on transcription from a T7 gn10-lac fusion promoter mediated by a coexpressed viral RNA polymerase (T7 gnl). This viral polymerase is supplied by host strains BL21(DE3) or HMS174 (DE3) from a resident λ prophage harboring a T7 gnl gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the D6 expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, D6 can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufinan et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboralory Manual. 2nd, ed, Cold Spring Harbor Laboratozy,* Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoidspecific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to D6 MRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, D6 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (eg., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding D6 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) D6 protein. Accordingly, the invention further provides methods for producing D6 protein using the host cells of the invention. In one embodiment, the method comprises culturing the host cell of invention (into which a recombinant expression vector encoding D6 has been introduced) in a suitable medium such that D6 protein is produced. In another embodiment, the method further comprises isolating D6 from the medium or the host cell.

The host cells of the invention can also be used to produce nonhuman transgenic animals. For example, in one embodiment, a host cell of the invention is a fertilized oocyte or an embryonic stem cell into which D6-coding sequences have been introduced. Such host cells can then be used to create non-human transgenic animals in which exogenous D6 sequences have been introduced into their genome or homologous recombination animals in which endogenous D6 sequences have been altered. Such animals are useful for studying the function and/or activity of D6 and for identifying and/or evaluating modulators of D6 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous D6 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing D6-encoding nucleic acid into the male pronuclei of a fertilized oocyte, e.g., by microinjection, retroviral infection, and allowing the oocyte to develop in a pseudopregnant female foster animal. The murine D6 cDNA sequence of SEQ ID NO:4 can be introduced as a transgene into the genome of a non-human animal. Alternatively, the human D6 cDNA sequence of SEQ ID NO:1 can be used as a transgene. Intronic sequences and polyadenylation signals can also be included in the transgene to increase the efficiency of expression of the transgene. A tissue-specific regulatory sequence(s) can be operably linked to the D6 trnsgene to direct expression of D6 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the D6 transgene in its genome and/or expression of D6 mRNA in tissues or cells of the animals. A transgenic founder animal can then be used to breed additional animals carrying the transgene. Moreover, transgenic animals carrying a transgene encoding D6 can further be bred to other transgenic animals carrying other transgenes.

To create a homologous recombinant animal, a vector is prepared which contains at least a portion of a D6 gene into which a deletion, addition or substitution has been introduced to thereby alter, e.g., functionally disrupt, the D6 gene. The D6 gene can be a murine gene (e.g., the cDNA of SEQ ID NO:4 or SEQ ID NO:6), but can also be a non-murine homologue of a murine D6 gene. For example, the human D6 gene (e.g., the cDNA of SEQ ID NO:1or SEQ ID NO:3) can be used to construct a homologous recombination vector suitable for altering an endogenous D6 gene in the mouse genome. In a preferred embodiment, the vector is designed such that, upon homologous recombination, the endogenous D6 gene is functionally disrupted (i.e., no longer encodes a functional protein; also referred to as a "knock out" vector). Alternatively, the vector can be designed such that, upon homologous recombination, the endogenous D6 gene is mutated or otherwise altered but still encodes functional protein (e.g., the upstream regulatory region can be altered to thereby alter the expression of the endogenous D6 protein). In the homologous recombination vector, the altered portion of the D6 gene is flanked at its 5' and 3' ends by additional nucleic acid of the D6 gene to allow for homologous recombination to occur between the exogenous D6 gene carried by the vector and an endogenous D6 gene in an embryonic stem cell. The additional flanking D6 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced D6 gene has homologously recombined with the endogenous D6 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The D6 nucleic acid molecules, D6 proteins, and anti-D6 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a D6 protein or anti-D6 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detecting assays (e.g., chromosome mapping, tissue typing, and forensic biology); c) predictive medicine (e.g., diagnostic assays, prognostic assays, monitoring clinical trials, and pharmacogenetics); and d) methods of treatment (e.g., therapeutic and prophylactic methods as well as such methods in the context of pharmacogenomics). As described herein, a D6 protein of the invention has one or more of the following activities: (i) interaction of a D6 protein on the cell surface with a second non-D6 protein molecule on the surface of the same cell; (ii) interaction of a D6 protein on the cell surface with a second non-D6 protein molecule on the surface of a different cell; (iii) complex formation between a membrane-bound D6 protein and a chemokine e.g., MIP-1α or JE; (iv) interaction of a D6 protein with an intracellular protein including protein kinase or cytoskeletal proteins; and (v) stimulation of cell migration. The D6 proteins of the invention can can thus be used in, for example, (1) modulation of cellular signal transduction, either in vitro or in vivo; (2) modulation of proinflammatory function of chemokines; (3) modulation of cellular signal transduction; (4) regulation of cellular proliferation; (5) regulation of cellular migration; and (6) modulation of chemokine-stimulated chemotaxis. The isolated nucleic acid molecules of the invention can be used, for example, to express D6 protein (e.g., via a recombinant expression vector in a host cell in gene therapy applications), to detect D6 mRNA (e.g., in a biological sample) or a genetic alteration in a D6 gene, and to modulate D6 activity, as described further below. In addition, the D6 proteins can be used to screen drugs or compounds which modulate the D6 activity as well as to treat disorders characterized by insufficient or excessive production of D6 protein or production of D6 protein forms which have decreased or aberrant activity compared to D6 wild type protein (e.g., allergic responses such as asthma or inflammatory diseases such as rheumatoid arthritis and chronic lung inflammation). Moreover, the anti-D6 antibodies of the invention can be used to detect and isolate D6 proteins, regulate the bioavailability of D6 proteins, and modulate D6 activity.

A. Screening Assays:

The invention provides a method (also referred to herein as a "screening assay") for identifing modulators, i.e., candidate or test compounds or agents (e.g., peptides, peptidomimetics, small molecules or other drugs) which bind to D6 proteins or have a stimulatory or inhibitory effect on, for example, D6 expression or D6 activity.

In one embodiment, the invention provides assays for screening candidate or test compounds which bind to or modulate the activity of a D6 protein or polypeptide or biologically active portion thereof. In another embodiment, the invention provides assays for screening candidate or test compounds which bind to or modulate the activity of a D6 receptor. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a D6 receptor on the cell surface is contacted with a test compound and the ability of the test compound to bind to a D6 receptor is determined. The cell, for example, can be of mammalian origin or a yeast cell. Determining the ability of the test compound to bind to a D6 receptor can be accomplished, for example, by coupling the test compound with a radioisotope or enzymatic label such that binding of the test compound to the D6 receptor can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a test compound to interact with a D6 receptor without the labeling of any of the interactants. For example, a microphysiometer can be used to detect the interaction of a test compound with a D6 receptor without the labeling of either the test compound or the receptor. McConnell, H. M. et al. (1992) *Science* 257:1906–1912. As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand and receptor.

In a preferred embodiment, the assay comprises contacting a cell which expresses D6 on the cell surface with a D6 ligand (e.g., a chemokine) or biologically-active portion thereof, to form an assay mixture, contacting the assay mixture with a test compound, and determining the ability of the test compound to interact with D6, wherein determining the ability of the test compound to interact with D6 comprises determining the ability of the test compound to preferentially bind to the D6 as compared to the ability of a D6 ligand (e.g., a chemokine), or a biologically active portion thereof, to bind to the receptor.

Determining the ability of the D6 ligand to bind to or interact with D6 can be accomplished by one of the methods described above for determining direct binding. In a preferred embodiment, determining the ability of the D6 ligand to bind to or interact with D6 can be accomplished by determining the activity of D6. For example, the activity of D6 can be determined by detecting induction of a cellular second messenger of the target (e.g., intracellular $Ca^{2+}$, diacylglycerol, $IP_3$, etc.), detecting catalytic/enzymatic activity of the target an appropriate substrate, detecting the induction of a reporter gene (comprising a D6-responsive regulatory element operatively linked to a nucleic acid encoding a detectable marker, e.g., luciferase), or detecting a cellular response, for example, development, differentiation or rate of proliferation.

In yet another embodiment, an assay of the present invention is a cell-free assay in which a D6 protein or biologically active portion thereof is contacted with a test compound and the ability of the test compound to bind to the D6 protein or biologically active portion thereof is determined. Binding of the test compound to the D6 protein can be determined either directly or indirectly as described above. In a preferred embodiment, the assay includes contacting the D6 protein or biologically active portion thereof with a known compound which binds D6 to form an assay mixture, contacting the assay mixture with a test compound, and determining the ability of the test compound to interact with a D6 protein, wherein determining the ability of the test compound to interact with a D6 protein comprises determining the ability of the test compound to preferentially bind to D6 or biologically active portion thereof as compared to the known compound.

In another embodiment, the assay is a cell-free assay in which a D6 protein or biologically active portion thereof is contacted with a test compound and the ability of the test compound to modulate (e.g., stimulate or inhibit) the activity of the D6 protein or biologically active portion thereof is determined. Determining the ability of the test compound to modulate the activity of a D6 protein can be accomplished, for example, by determining the ability of the D6 protein to bind to a D6 target molecule by one of the methods described above for determining direct binding. Determining the ability of the D6 protein to bind to a D6 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

In an alternative embodiment, determining the ability of the test compound to modulate the activity of a D6 protein can be accomplished by determining the ability of the D6 protein to further modulate the activity of a D6 target molecule. For example, the catalytic/enzymatic activity of the target molecule on an appropriate substrate can be determined as previously described.

In yet another embodiment, the cell-free assay involves contacting a D6 protein or biologically active portion thereof with a known compound which binds the D6 protein to form an assay mixture, contacting the assay mixture with a test compound, and determining the ability of the test compound to interact with the D6 protein, wherein determining the ability of the test compound to interact with the D6 protein comprises determining the ability of the D6 protein to preferentially bind to or modulate the activity of a D6 target molecule.

The cell-free assays of the present invention are amenable to use of both soluble and/or membrane-bound forms of isolated proteins (e.g., D6 proteins or biologically active portions thereof or D6 target molecules). In the case of cell-free assays in which a membrane-bound form an isolated protein is used (e.g., a D6 target molecule or receptor) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either D6 or its target molecule to facilitate separation of complexed from uncomplexed forms of one or both of the proteins, as well as to accommodate automation of the assay. Binding of a test compound to a D6 protein, or interaction of a D6 protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/ D6 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or D6 protein, and the mixture incubated under conditions conducive to complex formation (e.g., at physiological conditions for salt and pH). Following incubation, the beads or microtitre plate wells are washed to remove any unbound components, the matrix inmnobilized in the case of beads, complex determined either directly or indirectly, for example, as described above. Alternatively, the complexes can be dissociated from the matrix, and the level of D6 binding or activity determined using standard techniques.

Other techniques for immobilizing proteins on matrices can also be used in the screening assays of the invention. For example, either a D6 protein or a D6 target molecule can be immobilized utilizing conjugation of biotin and streptavidin.

Biotinylated D6 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with D6 protein or target molecules but which do not interfere with binding of the D6 protein to its target molecule can be derivatized to the wells of the plate, and unbound target or D6 protein trapped in the wells by antibody conjugation. Methods for detecting such complexes, in addition to those described above for the GST-immobilized complexes, include immunodetection of complexes using antibodies reactive with the D6 protein or target molecule, as well as enzyme-linked assays which rely on detecting an enzymatic activity associated with the D6 protein or target molecule.

In another embodiment, modulators of D6 expression are identified in a method wherein a cell is contacted with a candidate compound and the expression of D6 mRNA or protein in the cell is determined. The level of expression of D6 mRNA or protein in the presence of the candidate compound is compared to the level of expression of D6 mRNA or protein in the absence of the candidate compound. The candidate compound can then be identified as a modulator of D6 expression based on this comparison. For example, when expression of D6 mRNA or protein is greater (statistically significantly greater) in the presence of the candidate compound than in its absence, the candidate compound is identified as a stimulator of D6 mRNA or protein expression. Alternatively, when expression of D6 mRNA or protein is less (statistically significantly less) in the presence of the candidate compound than in its absence, the candidate compound is identified as an inhibitor of D6 mRNA or protein expression. The level of D6 mRNA or protein expression in the cells can be determined by methods described herein for detecting D6 mRNA or protein.

In yet another aspect of the invention, the D6 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO094/10300), to identify other proteins, which bind to or interact with D6 ("D6-binding proteins" or "D6-bp") and modulate D6 activity. Such D6-binding proteins are also likely to be involved in the propagation of signals by the D6 proteins as, for example, downstream elements of a D6-mediated signaling pathway.

The two-hybrid system is based on the modular nature of most transcription factors, which consist of separable DNA-binding and activation domains. Briefly, the assay utilizes two different DNA constructs. In one construct, the gene that codes for a D6 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an D6-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the D6 protein.

This invention further pertains to novel agents identified by the above-described screening assays. Accordingly, it is within the scope of this invention to further use an agent identified as described herein in an appropriate animal model. For example, an agent identified as described herein (e.g., a D6 modulating agent, an antisense D6 nucleic acid molecule, a D6-specific antibody, or a D6-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the D6 nucleotide sequences, described herein, can be used to map the location of the D6 genes on a chromosome. The mapping of the D6 sequences to chromosomes is an important first step in correlating these sequences with genes associated with disease.

Briefly, D6 genes can be mapped to chromosomes by preparing PCR primers (preferably 15–25 bp in length) from the D6 nucleotide sequences. Computer analysis of the D6 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the D6 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the D6 nucleotide sequences to design oligonucleotide primers, sublocalization can be achieved with panels of fragments from specific chromosomes. Other mapping strategies which can similarly be used to map a D6 sequence to its chromosome include in situ hybridization (described in Fan, Y. et al. (1990) PNAS, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783–787.

Moreover, differences in the DNA sequences between individuals affected and unaffected with a disease associated with the D6 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The D6 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the D6 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The D6 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from D6 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial D6 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the D6 nucleotide sequences or portions thereof, e.g., fragments derived from the noncoding regions of SEQ ID NO:1, having a length of at least 10 bases, preferably at least 20–30 bases.

The D6 nucleotide sequences described herein can further be used to provide polynucleotide reagents, e.g., labeled or labelable probes which can be used in, for example, an in situ hybridization technique, to identify a specific tissue, e.g., brain or lung tissue. This can be very useful in cases where a forensic pathologist is presented with a tissue of unknown origin. Panels of such D6 probes can be used to identify tissue by species and/or by organ type.

In a similar fashion, these reagents, e.g., D6 primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining D6 protein and/or nucleic acid expression as well as D6 activity, in the context of a biological sample (e.g., blood, serum, cells, tissue) to thereby determine whether an individual is afflicted with a disease or disorder, or is at risk of developing a disorder, associated with aberrant D6 expression or activity. The invention also provides for prognostic (or predictive) assays for determining whether an individual is at risk of developing a disorder associated with D6 protein, nucleic acid expression or activity. For example, mutations in a D6 gene can be assayed in a biological sample. Such assays can be used for prognostic or predictive purpose to thereby phophylactically treat an individual prior to the onset of a disorder characterized by or associated with D6 protein, nucleic acid expression or activity such as asthma.

Another aspect of the invention pertains to monitoring the influence of agents (e.g., drugs, compounds) on the expression or activity of D6 in clinical trials.

These and other agents are described in further detail in the following sections.

1. Diagnostic Assays

An exemplary method for detecting the presence or absence of D6 protein or nucleic acid in a biological sample involves obtaining a biological sample from a test subject and contacting the biological sample with a compound or an agent capable of detecting D6 protein or nucleic acid (e.g., mRNA, genomic DNA) that encodes D6 protein such that the presence of D6 protein or nucleic acid is detected in the biological sample. A preferred agent for detecting D6 mRNA or genomic DNA is a labeled nucleic acid probe capable of hybridizing to D6 mRNA or genomic DNA. The nucleic acid probe can be, for example, a full-length D6 nucleic acid, such as the nucleic acid of SE ID NO:1, or a portion thereof, such as an oligonucleotide of at least 15, 30, 50, 100, 250 or 500 nucleotides in length and sufficient to specifically hybridize under stringent conditions to D6 mRNA or genomic DNA. Other suitable probes for use in the diagnostic assays of the invention are described herein.

A preferred agent for detecting D6 protein is an antibody capable of binding to D6 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect D6 mRNA, protein, or genomic DNA in a biological sample in vitro as well as in vivo. For example, in vitro techniques for detection of D6 MnRNA include Northern hybridizations and in situ hybridizations. In vitro techniques for detection of D6 protein include enzyme linked immunosorbent assays (ELISAs), Western blots, immunoprecipitations and immunofluorescence. In vitro techniques for detection of D6 genomic DNA include Southern hybridizations. Furthermore, in vivo techniques for detection of D6 protein include introducing into a subject a labeled anti-D6 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting D6 protein, mRNA, or genomic DNA, such that the presence of D6 protein, mRNA or genomic DNA is detected in the biological sample, and comparing the presence of D6 protein, mRNA or genomic DNA in the control sample with the presence of D6 protein, mRNA or genomic DNA in the test sample.

The invention also encompasses kits for detecting the presence of D6 in a biological sample. For example, the kit can comprise a labeled compound or agent capable of detecting D6 protein or mRNA in a biological sample; means for determining the amount of D6 in the sample; and means for comparing the amount of D6 in the sample with a standard. The compound or agent can be packaged in a suitable container. The kit can further comprise instructions for using the kit to detect D6 protein or nucleic acid.

2. Prognostic Assays

The diagnostic methods described herein can furthermore be utilized to identify subjects having or at risk of developing a disease or disorder associated with aberrant D6 expression or activity. For example, the assays described herein, such as the preceding diagnostic assays or the following assays, can be utilized to identify a subject having or at risk of developing a disorder associated with D6 protein, nucleic acid expression or activity such as a proliferative disorder, a differentiative or developmental disorder, or a hematopoietic disorder. Alternatively, the prognostic assays can be utilized to identify a subject having or at risk for developing a differentiative or proliferative disease (e.g., rheumatoid arthritis or chronic lung inflammation). Thus, the present invention provides a method for identifying a disease or disorder associated with aberrant D6 expression or activity in which a test sample is obtained from a subject and D6 protein or nucleic acid (e.g, mRNA, genomic DNA) is detected, wherein the presence of D6 protein or nucleic acid is diagnostic for a subject having or at risk of developing a disease or disorder associated with aberrant D6 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant D6 expression or activity. For example, such methods can be used to determine whether a subject can be effectively treated with an agent for a disorder, such as a proliferative disorder, a differentiative or developmental disorder, or a hematopoietic disorder. Alternatively, such methods can be used to determine whether a subject can be effectively treated with an agent for a differentiative or proliferative disease (e.g., rheumatoid arthris). In a preferred embodiment, such methods can be used to determine whether a subject can be effectively treated with an agent for an allergic response such as asthma. Thus, the present invention provides methods for determining whether a subject can be effectively treated with an agent for a disorder associated with aberrant D6 expression or activity in which a test sample is obtained and D6 protein or nucleic acid expression or activity is detected (e.g., wherein the abundance of D6 protein or nucleic acid expression or activity is diagnostic for a subject that can be administered the agent to treat a disorder associated with aberrant D6 expression or activity.)

The methods of the invention can also be used to detect genetic alterations in a D6 gene, thereby determining if a subject with the altered gene is at risk for a disorder characterized by aberrant development, aberrant cellular differentiation, aberrant cellular proliferation or an aberrant hematopoietic response. For example, alterations detected in a D6 gene can be used to determine if a subject is at risk for asthma, lung allergic inflammation, airway hyperreactivity or HIV. In preferred embodiments, the methods include detecting, in a sample of cells from the subject, the presence or absence of a genetic alteration characterized by at least one of an alteration affecting the integrity of a gene encoding a D6-protein, or the mis-expression of the D6 gene. For example, such genetic alterations can be detected by ascertaining the existence of at least one of 1) a deletion of one or more nucleotides from an D6 gene; 2) an addition of one or more nucleotides to a D6 gene; 3) a substitution of one or more nucleotides of a D6 gene, 4) a chromosomal rearrangement of a D6 gene; 5) an alteration in the level of a messenger RNA transcript of a D6 gene, 6) aberrant modification of a D6 gene, such as of the methylation pattern of the genomic DNA, 7) the presence of a non-wild type splicing pattern of a messenger RNA transcript of a D6 gene, 8) a non-wild type level of a D6-protein, 9) allelic loss of a D6 gene, and 10) inappropriate post-translational modification of a D6-protein. As described herein, there are a large number of assay techniques known in the art which can be used for detecting alterations in a D6 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the D6-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a D6 gene under conditions such that hybridization and amplification of the D6-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et all, 1988, Bio/Technology 6:1197), or any other nucleic acid amplification method, followed by the detection of the amplified molecules using techniques well known to those of skill in the art. These detection schemes are especially usefuil for the detection of nucleic acid molecules if such molecules are present in very low numbers.

In an alternative embodiment, mutations in a D6 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in D6 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in D6 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the D6 gene and detect mutations by comparing the sequence of the sample D6 with the corresponding wild-type (control) sequence. Examples of sequencing reactions include those based on techniques developed by Maxim and Gilbert ((1977) *PNAS* 74:560) or Sanger ((1977) *PNAS* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the D6 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type D6 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in D6 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a D6 sequence, e.g., a wild-type D6 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in D6 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat Res* 285:125–144; and Hayashi(1992) *Genet Anal Tech Appl* 9:73–79). Single-stranded DNA fragments of sample and control D6 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a D6 gene.

Furthermore, any cell type or tissue in which D6 is expressed may be utilized in the prognostic assays described herein.

3. Monitoring of Effects During Clinical Trials

Monitoring the influence of agents (e.g., drugs, compounds) on the expression or activity of D6 (e.g., modulation of cellular signal transduction, allergic reactions or regulation of cellular proliferation) can be applied not only in basic drug screening, but also in clinical trials. For example, the effectiveness of an agent determined by a screening assay as described herein to increase D6 gene expression, protein levels, or upregulate D6 activity, can be monitored in clinical trials of subjects exhibiting decreased D6 gene expression, protein levels, or downregulated D6 activity. Alternatively, the effectiveness of an agent determined by a screening assay to decrease D6 gene expression, protein levels, or downregulate D6 activity, can be monitored in clinical trials of subjects exhibiting increased D6 gene expression, protein levels, or upregulated D6 activity. In such clinical trials, the expression or activity of D6 and, preferably, other genes that have been implicated in, for example, a proliferative disorder can be used as a "read out" or markers of the phenotype of a particular cell.

For example, and not by way of limitation, genes, including D6, that are modulated in cells by treatment with an agent (e.g., compound, drug or small molecule) which modulates D6 activity (e.g., identified in a screening assay as described herein) can be identified. Thus, to study the effect of agents on proliferative disorders, developmental or differentiative disorder, or hematopoietic disorder, for example, in a clinical trial, cells can be isolated and RNA prepared and analyzed for the levels of expression of D6 and other genes implicated in the proliferative disorder, developmental or differentiative disorder, or hematopoietic disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of D6 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a D6 protein, mRNA, or genomic DNA in the preadministration sample; (iii) obtaining one or more post-administration samples from the subject; (iv) detecting the level of expression or activity of the D6 protein, mRNA, or genomic DNA in the post-administration samples; (v) comparing the level of expression or activity of the D6 protein, mRNA, or genomic DNA in the pre-administration sample with the D6 protein, mRNA, or genomic DNA in the post administration sample or samples; and (vi) altering the administration of the agent to the subject accordingly. For example, increased administration of the agent may be desirable to increase the expression or activity of D6 to higher levels than detected, i.e., to increase the effectiveness of the agent. Alternatively, decreased administration of the agent may be desirable to decrease expression or activity of D6 to lower levels than detected, i.e to decrease the effectiveness of the agent. According to such an embodiment, D6 expression or activity may be used as an indicator of the effectiveness of an agent, even in the absence of an observable phenotypic response.

C. Methods of Treatment:

The present invention provides for both prophylactic and therapeutic methods of treating a subject at risk of (or susceptible to) a disorder or having a disorder associated with aberrant D6 expression or activity such as asthma, lung allergic inflammation, airway hyperreactivity, or HIV. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the D6 molecules of the present invention or D6 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant D6 expression or activity, by administering to the subject an agent which modulates D6 expression or at least one D6 activity. Subjects at risk for a disease which is caused or contributed to by aberrant D6 expression or activity can be identified by, for example, any or a combination of diagnostic or prognostic assays as described herein. Administration of a prophylactic agent can occur prior to the manifestation of symptoms characteristic of the D6 aberrancy, such that a disease or disorder is prevented or, alternatively, delayed in its progression. Depending on the type of D6 aberrancy, for example, a D6 agonist or D6 antagonist agent can be used for treating the subject. The appropriate agent can be determined based on screening assays described herein. The prophylactic methods of the present invention are further discussed in the following subsections.

2. Therapeutic Methods

Another aspect of the invention pertains to methods of modulating D6 expression or activity for therapeutic purposes. The modulatory method of the invention involves contacting a cell with an agent that modulates one or more of the activities of D6 protein activity associated with the cell. An agent that modulates D6 protein activity can be an agent as described herein, such as a nucleic acid or a protein, a naturally-occurring target molecule of a D6 protein, a peptide, a D6 peptidomimetic, or other small molecule. In one embodiment, the agent stimulates one or more D6 protein activity. Examples of such stimulatory agents include active D6 protein and a nucleic acid molecule encoding D6 that has been introduced into the cell. In another embodiment, the agent inhibits one or more D6 protein activity. Examples of such inhibitory agents include antisense D6 nucleic acid molecules and anti-D6 antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a D6 protein or nucleic acid molecule (e.g., asthma, lung allergic inflammation, airway hyperreactivity, or HIV). In one embodiment, the method involves administering an agent (e.g., an agent identified by a screening assay described herein), or combination of agents that modulates (e.g., upregulates or downregulates)

D6 expression or activity. In another embodiment, the method involves administering a D6 protein or nucleic acid molecule as therapy to compensate for reduced or aberrant D6 expression or activity.

Stimulation of D6 activity is desirable in situations in which D6 is abnormally downregulated and/or in which increased D6 activity is likely to have a beneficial effect. Likewise, inhibition of D6 activity is desirable in situations in which D6 is abnormally upregulated and/or in which decreased D6 activity is likely to have a beneficial effect such with asthma. One example of such a situation is where a subject has a disorder characterized by aberrant inflammatory response. Another example of such a situation is where the subject has a proliferative disease (e.g., rheumatoid arthritis) or a disorder characterized by an aberrant hematopoietic response. Specifically, modulation of D6 activity is desirable in a situation where a subject has asthma, lung allergic inflammation, airway hyperreactivity or HIV.

3. Pharmacogenomics

The D6 molecules of the present invention, as well as agents, or modulators which have a stimulatory or inhibitory effect on D6 activity (e.g., D6 gene expression) as identified by a screening assay described herein can be administered to individuals to treat (prophylactically or therapeutically) disorders (e.g, proliferative or developmental disorders) associated with aberrant D6 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a D6 molecule or D6 modulator as well as tailoring the dosage and/or therapeutic regimen of treatment with a D6 molecule or D6 modulator.

Pharmacogenomics deals with clinically significant hereditary variations in the response to drugs due to altered drug disposition and abnormal action in affected persons. See e.g., Eichelbaum, M., *Clin Exp Pharmacol Physiol*, 1996, 23(10–11):983–985 and Linder, M. W., *Clin Chem*, 1997, 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug target is known (e.g., a D6 receptor of the present invention), all common variants of that gene can be identified in the population and a particular drug response can be associated with one or more genes.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a D6 molecule or D6 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a D6 molecule or D6 modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1
Identification of Murine and Human D6 cDNA

In this example, the isolation and characterization of the cDNA encoding murine and human D6 is described. These D6 genes encode D6 proteins belonging to the G protein-coupled heptahelical receptor superfamily.

Murine D6 cDNA Isolation and Identification

Murine D6 cDNA was isolated from homogenized spleen of a CH3 mouse according to the methods described in Sambrook et al. (1989) *Molecular Cloning: A Laboratory Manual*, 2nd Ed. (Cold Spring Harbor Laboratory, Cold Spring Harbor, N.Y.). Briefly, the following oligonucleotide primers were synthesized from regions of similarity between human CCR-1, CCR-2, and cytomegalovirus US28.for primer #2:

Sense Primers
1 5'-GGGGCICA(A/G)CT(G/C)CT(G/C)CCICC-3' (SEQ ID NO: 9)
2 5'-ACCAC(A/C)ITITTTGA(T/C)TATG-3' (SEQ ID NO: 10)
3 5'-AT(T/C)TA(T/C)CTICTIAACCT(C/G)GC-3' (SEQ ID NO: 11)
Antisense Primers
4 5'-GTIAG(G/C)AGGATGAT(A/G)AA(A/G)AAAAT-3' (SEQ ID NO: 12)
5 5'-GACIAT(A/G)GCCAGGTACC(G/T)GTC-3' (SEQ ID NO: 13)

PCR was performed using variable amounts of $MgCl_2$ (from 1.25 to 2.25 mM), 0.3 mM of each dNTP, and 6 ng/$\mu$l of one sense and one antisense oligonucleotide. Reactions were incubated for 35 cycles at 94° C. for 1 minute, 50–52° C. for 1 minute, and 72° C. for 2 min. Products of expected size were cloned into pCRScript™ (Stratagene, La Jolla, Calif.) and sequenced. 5' and 3' rapid amplification of cDNA ends (RACE) was performed using RACE kits from Life Technologies, Inc. (Paisley, UK) according to their instructions on tissues or cell lines positive for each receptor in RT-PCR reactions. No alternatively spliced forms of the type seen with human CCR-2 were detected. Pfu polymerase (Stratagene) was used on cDNA or genomic DNA according to the manufacturers' instructions, with reactions containing 10% dimethyl sulfoxide and 5% glycerol and oligonucleotides specific to the 5' and 3' ends of the gene. Three separate reactions were performed, and all products were cloned into pCRScript and fully sequenced in both orientations. Sequences were analyzed using GCG software (50): phylogenic relationships were determined using the Distances (Kimura method) and Growtree (Neighbor-joining method) programs.

Human D6 cDNA Isolation and Identification

Fragments of human D6 were generated by degenerate oligonucleotide-primed PCR using the following primers designed from the murine D6 receptor (30) in two regions that show conservation of amino acid sequence between other human and mouse chemokine receptors:

Sense Primers
1: 5'-TG(C/T)GGIATCTT(C/T)TT(C/T)AT(C/T)ACI TG(C/T)ATC-3' (SEQ ID NO:14)
2: 5'-GACAA(A/G)TA(C/T)CTI(GA(A/G)AT(C/T) GTICA(C/T)GC-3' (SEQ ID NO:15)
Antisense Primer
3: 5'-GTACAGIACIGGIGT(A/G)CA(A/G)CA(A/G)TG-3'. (SEQ ID NO:16)

PCR was performed using variable amounts of $MgCl^2$ (from 1.25 to 2.25 nM), 0.3 mM of each dNTP, and 6 ng/$\mu$l of one of the 5' oligonucleotides and hD6hcc. Genomic DNA template isolated from human lymphocytes was used at 1 $\mu$g per reaction. Reactions were incubated for 94° C. for 1 minute, 50–52° C. for 1 minute, and 72° C. for 2 min. Products of expected size were cloned into pCRScript (Stratagene, La Jolla, Calif.) and sequenced. Two different products were cloned: human D6, and a fragment identical to the previously cloned orphan heptahelical receptor, RDC-1. 5' and 3' rapid amplification of the human D6 cDNA ends (RACE) was performed using RACE kits form Life Technologies, Ltd., using oligonucleotide primers designed from the sequenced fragment. Reverse transcribed U937 cDNA was used as a template for the RACE reactions, which had previously been shown to express human D6. Once the start and stop codons were identified, the full-length gene was amplified with Pfu polymerase (Stratagene) in three separate reactions from human lymphocyte DNA. These products were cloned into pCRScript and fully sequenced. The three products were identical.

Characterization of Murine and Human D6

The original first pass sequence of the murine and human D6 clones showed homology to other members of the β chemokine receptor family using the BLAST™ program. The murine D6 nucleotide sequence and predicted amino acid sequence are shown in FIG. 2 (corresponding to SEQ ID NO:4 and SEQ ID NO:5, respectively). The human D6 nucleotide and amino acid sequence are shown in FIG. 1 (corresponding to SEQ ID NO:1 and SEQ ID NO:2, respectively). The human D6 protein (corresponding to amino acids 1–384 of the predicted amino acid sequence, SEQ ID NO:2) shows about 40% identity to eight other human β chemokine receptors (see FIG. 3). The percent identity was calculated using the alignment generated using MegAlign™ sequence alignment software. The initial pairwise alignment step was performed using a Wilbur-Lipmann algorithm with a K-tuple of 1, a GAP penalty of 3, a window of 5, and diagonals saved set to=4. The multiple alignment step was performed using the Clustal algorithm with a PAM 250 residue weight Table, a GAP penalty of 10, and a GAP length penalty of 10.

Both the human and murine D6 proteins contain two G protein docking motifs (corresponding to amino acid residues 141–149 of SEQ ID NO:2 and amino acid residues 140–148 of SEQ ID NO:5, respectively), four conserved cysteine residues (corresponding to amino acid residues 36, 117, 195 and 284 of SEQ ID NO:2 and amino acid residues 35, 116, 194 and 283 of SEQ ID NO:5, respectively), and a single putative N-linked glycosylation site (corresponding to amino acid residues 19–21 of SEQ ID NO:2 and amino acid residues 17–19 of SEQ ID NO:5, respectively). The human and murine D6 proteins also have seven transmembrane domains. In human D6 protein, the transmembrane domains correspond to amino acid residues 67–92, 103–124, 139–159, 178–203, 228–249, 269–292 and amino acid residues 309–331 of SEQ ID NO:2. In murine D6, the transmembrane domains correspond to amino acid residues 66–91, 102–123, 138–158, 177–202, 227–248, 268–291 and amino acid residues 308–330 of SEQ ID NO:5.

Example 2
Tissue Expression of the D6 Gene

Northern Blot Analysis of Murine D6 mRNA

The expression of murine D6 was analyzed using northern blot hybridization. For analysis of murine D6, northern blots were performed onto Hybond N+ (Amersham, Little Chalfont, UK) according to Nibbs et al. (1993) *Mol. Cell Biol.* 13:5582–5592, using full length murine D6 DNA as a probe. The probe DNA was radioactively labeled with $^{32}$P-dCTP using the Ready-To-Go™ kit (Pharmacia) and removing unincorporated nucleotides using NICK Sephadex G-50 columns (Pharmacia). Filters containing total RNA, extracted using Trizol (Life Technologies, Inc.), were probed in hybridization solution and washed to a final stringency of 0.1×SSC, 0.1% SDS.

This initial analysis of murine D6 indicated expression of an approximately 3.2 k6 transcript detectable in lung and at much lower levels in liver and spleen.

Northern Blot Analysis of Human D6 mRNA

For analysis of human D6, full length human D6 cDNA was used as a probe. The probe DNA was radioactively labeled with $^{32}$P-dCTP using the Ready-To-Go™ labeling kit (Pharmacia, St. Albans, UK) and unincorporated nucleotides were removed using NICK-Sephadex G-50 columns (Pharmacia). Filters containing poly A+ mRNA from various human tissues (Cambridge Bioscience, Cambridge, UK) were probed in ExpressHyb™ hybridization solution (Cambridge Bioscience) and washed at high stringency according to manufacturer's recommendations.

Two transcripts of approximately 4 kb and 6 kb were observed at variable levels in several tissues including placenta, liver, lung and thyroid. Highest expression levels were observed in the placenta and the lowest levels of expression were in the thyroid and lung. Prolonged exposure of these blots also demonstrated weak expression of human D6 in small intestine and the mucosal lining of the colon.

RT-PCR Analysis of Murine and Human D6 mRNA

Further expression of murine and human D6 mRNA was analyzed using RT-PCR. RT-PCR was performed using the RNA PCR core kit (Perkin-Elmer, Branchburg, N.J.) and the following primers:

Murine Primers

Sense: 5'-GTGACAGAGAGCCTGGCCTTC-3' (SEQ ID NO:17)

Antisense: 5'-GGAAGAGACAGTAATGAGTAAGGC-3' (SEQ ID NO:1 8)

Human Primers

Sense: 5'-CGT TCA TGC TCA GCC CTA C-3' (SEQ ID NO:19)

Antisense: 5'-CTG GAG TGC GTA GTC TAG ATG C-'3 (SEQ ID NO:20)

For each RNA sample, reverse transcription was done in two tubes, one with and one without reverse transcriptase. 1 µg of heat-denatured total RNA was used per PCR reaction, which had been previously treated with DNase I to remove genomic DNA contaminants (according to Life Technologies, Inc. RACE kits), followed by phenol/chloroform extraction, ethanol precipitation, and 70% ethanol wash. PCR proceeded for 30 cycles of 94° C. for 1 minute, 58° C. for 1 minute, 72° C. for 1 min.

RT-PCR analysis further revealed expression of murine D6 in heart, brain, thymus, ovary, muscle, liver and kidney. No expression was observed, however, in mammary gland or testes. RT-PCR analysis also revealed expression of human D6 in RNA prepared from leukocytes derived from umbilical cord blood and in the primitive erythromyeloid cell lines, K562 and THP-1 monocytic cells.

Multi-probe RNase Protection Analysis of Murine D6 Expression

The mRNA expression of murine D6 was studied during lung allergic inflammation in C57B16 mice in order to determine D6 expression during allergic responses. Lung allergic inflammation was induced according to the protocol described by Gonzalo et al. (1996) *Immunity* 4:1–14 or Coyle et al. (1996) *J. Exp. Med.* 183:1303–1310. Total RNA from the lungs of OVA-treated mice or control littermates at different time points was extracted by single-step method using RNA STAT-60™ from Tel-Test.

Murine D6 mRNA expression was determined by Multi-probe RNase Protection Assay. Briefly, a murine D6 probe was derived by PCR using the following primers:

Sense: 5' GCCGCGGCCCCTGGTGATAG 3' (SEQ ID NO:21)

Antisense: 5' AGCGGTGACTGCAGAAGGCGTAGA 3' (SEQ ID NO:22)

A (32P)-labeled anti-sense probe set was synthesized and hybridized to excess RNA. Free probe and other single-stranded RNA molecules were digested with RNAses. The remaining "RNase-protected" fragment was resolved on a denaturing polyacrylamide gel according to the fragment size, and imaged by autoradiograph and beta imaging. The identity and quantity of each mRNA species in the original RNA sample can then be determined based on the signal intensities given by the appropriately-sized, protected probe fragment bands. Values were created by expressing murine D6 upregulation relative to its expression in normal tissue.

Multi-probe RNase-Protection Analysis revealed the murine D6 is upregulated by 3-fold in the lungs at day 15 during the Gonzalo et al. model of allergic eosinophilia.

In Situ Hybridization Analysis of Murine D6 Expression in Lung Tissue

Murine D6 mRNA expression was determined in lung tissue by in situ hybridization using an oligonucleotide probe designed in the 3' UTR, with the following sequence:

5'-CCAGGAAGCAGAAGGAGGAAGAGACAGTAATG AGTAAGGC-3' (SEQ ID NO:23)

In situ hybridization analysis revealed that murine D6 is expressed by infiltrating mononuclear cells during lung allergic inflammation induced by the protocol described in Gonzalo et al. (1996) *Immunity* 4:1–14.

In Situ Hybridization Analysis of Human D6 Expression in Lung Tissue

Human D6 mRNA expression was also determined by in situ hybridization—using $^{35}$S-labeled oligonucleotide probes as described in Sutherland et al. (1996) *J. Neurosci.* 16(7):2191–2207, using probes with the following sequences:

Probes

1:

5'-TGGAGAAGGCATACAGGATGGGGGAAAAGCA GCAGTGAAA (SEQ ID NO:24)

2:

5'-TGGTCACTCAGGCTGATTTATTCCCCACATCCT TGTT (SEQ ID NO:25)

The tissue used for in situ analysis was broncheolar lavage cytospins collected from patients pre and post-antigenic challenge.

Preliminary results show that human D6 mRNA expression is upregulated in asthmatic patients following antigen challenge.

Example 3

Expression of Recombinant Murine and Human D6 Proteins Transfected Cell Lines

Generation of CHO and HEK 293 Cells Stably Expressing Murine D6

To express the murine D6 gene in CHO cells, the pcDNA3 vector by Invitrogen Corporation (San Diego, Calif.) is used. Full length cDNAs encoding the entire murine D6 protein were excised as BamHI/NotI fragments from the PCRScript vectors and cloned into the pcDNA3 vector.

These vectors were transfected into CHO cells and single cell clones were selected in 1.6 mg/ml geneticin (Life Technologies) as described in Graham et al. (1996) *EMBO J.* 15:6506–6515. Total RNA was extracted from approximately 12 separate clones, Northern blots were performed to asses expression levels and the three highest expressing clones were selected for ligand binding experiments. pcDNA3 containing murine D6 cDNA was transfected into HEK 293 cells using Transfectarm (Promega) according to manufacturers' recommendations. Stably transfected pools of cells were selected in 700 µg/ml geneticin.

Generation of CHO and Human Osteosarcoma Cells Stably Expressing Human D6

Full length cDNA encoding human D6 protein were transfected into CHO cells as described above. Stably transfected CHO cells were selected in 1.6 mg/ml geneticin (Life Technologies).

Hos.CD4 transfectants were generated as described in Lui et al. (1996) *Cell* 86:367–377. Briefly, human D6 was ligated into the pBABE-puro retroviral vector described in Morgenstern et al. (1990) *Nucleic Acid Res.* 18:3587–3596. This vector construct was used to transduce the Hos.CD4 human osteosarcoma cell line stably expressing CD4 cDNA. Transduced cells were selected in 1 µg/ml puromyocin and cell surface expression of human D6 was confirmed by radioiodinated MIP-1α binding and Scatchard analysis.

Example 4

Murine and Human D6 Receptor Binding Assays

Murine D6 Receptor Binding Assays

In order to identify murine D6 as a chemokine receptor, the following binding assays were performed to test the ability of murine D6 to bind murine MIP-1α, human RANTES, human MIP-1β, murine MIP-1β, human MCP-1, murine JE, human MCP-3 and murine C10.

5-µg aliquots of mMIP-1α were labeled on a regular basis with Na$^{125}$I (DuPont NEN) using IODO-GEN (Pierce) as described in Graham et al. (1993) *Cell Growth & Differ.* 4:137–146. Stably transfected CHO cells were plated at $10^5$ cells/well in 24-well plates and incubated overnight at 37° C. After washing with warm PBS, the cells were incubated in 250 µl of binding buffer (special liquid medium plus 10% fetal calf serum, 4 mM glutamine, 0.2% sodium azide, 25 mM HEPES (pH 7.4)) containing variable concentrations of radioiodinated MIP-1 and cold competitor chemokine. Binding proceeded for 90 minutes at 22° C., then each well washed three times in ice-cold PBS and the cell monolayer was then solubilized by the addition of 0.5 ml of 1% SDS. Lysed cells were transferred to a counting vial and bound radioactivity counted for 1 minute in Beckman Gamma 5500B counter. Each data point was assayed in triplicate and each experiment performed at least twice of accuracy. Data was analyzed using Scahot and Scafit programs in LIGAND software (Munson et al. (1980) *Anal. Biochem.* 107:220–239).

Initially, each transfected cell line, and the parental cell line, was tested for binding at 40 and 4 nM $^{125}$I-mMIP-1α. Transfected cells that exhibited a significant increase in binding above background were subjected to a full Scatchard analysis with 12 data points in triplicate with varying concentrations of $^{125}$I-mMIP-1α. $K_d$ values were then confirmed by varying the amount of unlabeled mMIP-1α while maintaining the $^{125}$I-mMIP-1α at approximately the $K_d$ value. Competition experiments with other labeled chemokines were similarly performed and the dissociation constants are presented in Table I.

TABLE I

| murine human MIP-κ | human RANTES | human MIP-1β | murine MIP-1β | human MCP-1 | murine JE | human MCP-2 | human MCP-3 | murine C10 |
|---|---|---|---|---|---|---|---|---|
| ND* | 2 nM | 0.26 nM | 0.77 nM | 52 nM | 1.5 nM | ND* | 5 nM | ND* |

*ND = not displaced

In addition, the ability of murine CCR-1, CCR-3 and CCR-5 to bind the various chemokines was compared with the binding affinities of these chemokines with murine D6. These results present murine D6 as the highest affinity receptor for murine MIP-1α. Murine D6, as demonstrated in Table I, also binds murine and human MIP-1β with $K_d$ values slightly higher than those seen with murine MIP-1α. Other human MCP-1, murine JE and human MCP-3 chemokines also bind to D6 with affinities in the nanomolar range.

Several α-chemokines, including IL-8, KC and MIP-2α, were also tested for their ability to displace murine MIP-1α binding to murine D6. None of these a-chemokines are capable of displacing radiolabeled MIP-1α from D6, thus, indicating that the murine D6 receptor is specific for the β-chemokine family.

Thus, the results of these binding assays demonstrate that murine D6 acts as a high affinity receptor for β-chemokines when it is expressed in CHO cells, binding to murine MIP-1α>human and murine MIP-1β>human RANTES and murine JE>human MCP-3>human MCP-1.

Human D6 Receptor Binding Assays

The following binding assays were performed to determine the ability of human D6 the bind several different chemokines.

The receptor binding assays were carried out as described above for the displacement analysis of murine D6 with cells being plated at $2\times10^5$ cells/well in 24-well plates and incubated overnight at 37° C. prior to binding analysis. Cells were incubated in azide-containing medium (pH 7.4) with a constant amount of radioiodinated murine MIP-1α and displacement analysis carried out using increasing concentrations of unlabeled chemokine ligands. Data was analyzed by the LIGAND program as described above for murine D6.

The results of competition experiments with labeled human chemokines were performed and the dissociation constants of these chemokines are presented in Table II.

TABLE II

| human MIP-1α | human MIP-1β | human RANTES | human MCP-1 | human MCP-2 | human MCP-3 | human MCP-4 | human HCCl | human Eotaxin |
|---|---|---|---|---|---|---|---|---|
| 64 nM | 1.7 nM | 3.6 nM | 16.5 nM | 768 nM | 1.2 nM | 5.9 nM | 27.2 nM | 46 nM |

In addition, competition experiments with various labeled murine chemokines were also performed and the dissociation constants of these chemokines are presented in Table III.

TABLE III

| murine MIP-1α | murine MIP-1β | murine MCP-1 | murine MCP-5 | murine Eotaxin |
|---|---|---|---|---|
| 920 pM | 755 pM | 613 nM | 6.3 nM | 30 nM |

These results indicate that human D6 is a highly promiscuous β-chemokine receptor that displays relatively high affinity binding for the majority of members of the β-chemokine family. The highest affinity ligands for human D6 appear to include murine MIP-1α and MIP-1β.

Example 5
Measuring Intracellular Calcium Flux of Cells Transfected with Murine D6
Intracellular $Ca^{2+}$ Measurements of Cells Transfected with Murine D6

HEK 293 cells stably transfected with murine D6 were harvested by trypsinization, washed with HACM buffer (125 mM NaCl, 5 mM KCl, 1 mM $MgCl_2$, 0.5 mM glucose, 0.025% bovine serum albumin, 20 mM HEPES (pH 7.4)), and loaded in HACM containing 10 µM Fura-2-AM (Sigma) for 60 minutes at 37° C. in the dark. Cells were washed twice in HACM. A 2 ml aliquot was placed in a continuously stirred cuvette at 37° C. in a Perkin-Elmer LS50 Spectrometer, CaCl2 was added to 100 nM and fluorescence was monitored at 340 nm (λem) and 500 nm (λem). Data was collected every 100 ms. Chemokines were added to a final concentration of 100 nM.

Treatment of the transfected cells with 100 nM mMIP-1α, mMIP-1β, or hRANTES generated a detectable increase in $Ca^{2+}$ demonstrating that murine D6 receptor is able to signal upon ligand interaction. hMCP-3 gave a slightly weaker response. In addition, each of the ligands was able to desensitize the cells to subsequent treatment 100 seconds later with a second murine D6 ligand. Untransfected HEK 293 cells were unresponsive to all chemokines tested.

Example 6
Measuring Calcium Flux of Cells Transfected wiht Human D6 and Mutations of Human D6
Preparation of Mutants of Human D6

All mutations were made using PCR using Pfu polymerase (Stratagene). Oligonucleotides were made on an Applied Biosystems 392 DNA/RNA synthesizer. Restriction enzymes were purchased from Life Technologies, Inc., Paisley, UK. The PCR was performed using 1×Pfu polymerase buffer, 10% dimethyl sulphoxide, 5 % glycerol, 5ng/µl of each primer, 0.4 mM of each nucleotide (ATP, GTP, CTP, TTP), 100 ng of human D6 cDNA in pBluescript and 2.5 Units of Pfu polymerase in a final volume of 100 µl. The reactions were allowed to proceed for 25 cycles at 94° C. for 1 minute, 58° C. for 1 minute, 72° C. for 1 minute. The fragments were cloned into human D6 in pBluescript (Stratagene) using appropriate restriction enzymes and fully sequenced to confirm the presence of the mutation and the absence of further mutations introduced as a consequence of the PCR.
Preparation of Mutant N19Q from Human D6

Mutant N19Q was made by converting asparagine 19 of human D6 to glutamine by overlap PCR. The first round of PCR was performed in two separate tubes using the following pairs of oligonucleotide primers:

1: 5' GAGAGAAGCTTGGATCCTCCAACATGGCCG 3' (D6Hind) (SEQ ID NO:39)
2 5' GAAGCTGCTCTGCTCAGAATCGGCAT 3' (NQantisense) (SEQ ID NO:40) and
1: 5' ATGCCGATTCTGAGCAGAGCAGCTTC 3' (NQsense) (SEQ ID NO:41)
2: 5' AGGTTGGAGATGGCCAGATTCAGC 3' (D6D5) (SEQ ID NO:42)

The products from these two reactions were then joined using primers D6Hind and D6D5 in the second round of PCR and 5 µl of the first PCR reactions as templates. The resulting fragment was cloned using Bgl II and Hind III into human D6 in pBluescript.
Preparation of Mutant K142R, E145A from Human D6

Mutant K142R, E145A was made by converting lysine 142 of human D6 to arginine and glutamic acid 145 of human D6 to alanine using overlap PCR. The first two reactions were performed using the following oligonucleotide pairs:

1: 5' TGGTTGAGATCTATCTGCTGAATC 3' (D6Bgl) (SEQ ID NO:43)
2: 5' CATGAACGATCGCCAGGTACCTGTCCAGGCTC 3' (drys) (SEQ ID NO:44) and
1: 5' GAGCCTCAGGTACCTGGCGATCGTTCATG 3' (drya) (SEQ ID NO:45)
2 5' GACACAGCCCATACTATGGTAGC 3' (D6D2) (SEQ ID NO:46)

The products from these two reactions were then joined using primers D6Bgl and D6D2 in the second round of PCR and 5 µl of the first two reactions as templates. The resulting fragment was cloned into human D6 in pBluescript using Bgl II and Sma I.
Preparation of Mutant N92D from Human D6

Mutant N92D was generated by converting asparagine 92 of human D6 to aspartic acid using the following oligonucleotide:

1: 5' TGGTTGAGATCTATCTGCTGAATCTGGC-CATCTCCGACCTTC 3' (D6Bglmu) (SEQ ID NO:47)
2: 5' GACACAGCCCATACTATGGTAGC 3' (D6D2) (SEQ ID NO:46)

The product was cloned into human D6 in pBluescript using Bgl II and Sma I.
Preparation of a Triple Mutant from Human D6

A triple mutant was also generated containing N92D and K142R,E145A. This was done as described for the K142R, E145A mutant except that the D6Bglmu oligonucleotide was used in place of the D6Bgl oligonucleotide.
Preparation of Clones Containing Human D6 Mutants All mutants were cloned into pcDNA3 using Hind III and Not I, transfected into CHO cells (for N19Q) and HEK 293 cells (for the other mutants) and single cell clones generated by selection in G418. High expressors were selected using radioligand binding analysis as described in Nibbs et al. (1997) *J. Biol. Chem.* 272:12495–12504. The HEK 293 transfectants were tested for their ability to flux calcium ions in response to ligand binding as described in Nibbs et al. (1997).
Intracellular $Ca^{2+}$ Measurements of Cells Transfected with Human D6 and Mutations of Human D6

The calcium flux experiments were done as described above for the murine D6 intracellular calcium fluxes. With respect to the results of the calcium fluxes of human D6 and mutants thereof, Table 1 shows the increases in Ca++ intracellularly as a result of incubation with the ligand. Wild type human D6 and mutant N92D do not give any increase. The N19Q mutant was not tested. The triple mutant is N92D,K142R,E145A. Each chemokine was added to a final concentration of 50 nM. The values were calculated using the following formula: $[Ca^{2+}]i$ (in nmol/l)=Kd Fura-2 [(F-Fmin)/(Fmax-F)] where Kd Fura-2=224; Fmax=peak with Triton lysed cells; Fmin=measurement of lysed cells after addition of EGTA; F=baseline fluorescence.

All mutants were equally well expressed on the surface of the cells and there appeared to be no change in the affinity of the receptors for radio-oriented murine MIP-1α. Preliminary results suggest that while the wild type human D6 receptor is unable to induce a calcium flux, the K142R, E145A mutant, and the triple mutant N92D, K142R, E145A are able to generate a weak but detectable flux in response to binding of all ligands known to interact with the wild type human D6 receptor. This response is approximately 20-fold less intense than that seen with human CCR5 or CCR1 in response to ligand binding. The N92D mutant is unable to induce a calcium flux. Thus, introduction of DRYLA into human D6 is able to restore some ability of this receptor to couple to calcium flux. These results are presented in Table IV.

TABLE IV

| Mutant | Ligand | [Ca++] in nmol/l |
|---|---|---|
| K142R, E145A | mMIP-1α | 28.2 |
| K142R, E145A | hRANTES | 19.3 |
| K142R, E145A | hMCP-2 | 22.9 |
| Triple mutant | mMIP-1α | 11.3 |
| Triple mutant | hMCP-2 | 13.7 |
| hCCR5 | hMIP-1α | 412.0 |

Example 7
Production of Anti-Murine D6 and Anti-Human D6 Antibodies

Antibodies against human D6 and murine D6 were generated to study cell surface expression of these receptors as well as their role in blockage experiments.

Monoclonal Antibody Production

Monoclonal antibodies reactive with human D6 were generated by immunizing Balb/C mice with 50 μg of a 36mer synthetic peptide corresponding to the first 36 N-terminal amino acids of SEQ ID NO:2, five times over a period of 10 weeks. This peptide was synthesized and coupled to purified protein derivative of tuberculin by the manufacturer (Research Genetics). The first immunization was intraperitoneal with Freund's complete adjuvant, the second, third and fourth were intraperitoneal with Freund's incomplete adjuvant, and the final immunization was protein alone administered intravenously. Four days after the last immunization, the spleen was taken and cell fusion performed using the cell line SP2/O, as described (Harlow, E and Lane, D. (1988) *Antibodies, A Laboratory Manual* (Cold Spring Harbor Laboratory, Cold Spring Harbor, N.Y.)). Eight monoclonal antibodies reactive with human D6 were identified using untransfected and human D6 transfected L1.2 cells, and immunofluorescent staining and analysis using a FACScan® (Becton Dickinson & Co., Mountain View, Calif.). To assess reactivity of the monoclonal antibodies against transfected cells or leukocytes, indirect immunofluorescence and flow cytometry were used. Cells were washed once with PBS, and resuspended in 100 μl PBS containing 2% human serum and 0.1% sodium azide (staining buffer), 50 μl specific hybridoma culture supernatant, or 50 ug of control hybridoma culture supernatant. After 20 minutes at 4° C., cells were washed twice with staining buffer, and resuspended in 50 μl FITC-conjugated affinity purified F(ab')2 goat anti-mouse IgG (Jackson ImmunoResearch Laboratories). After incubating for 20 minutes at 4° C., cells were washed twice in staining buffer and analyzed on the FACScan® to determine the level of surface expression. Propidium iodide was used to exclude dead cells. These antibodies showed staining of human D6 transfected cells, and no staining of untransfected L1.2 cells.

Polyclonal Antibody Production and Cell Surface Expression

A rabbit polyclonal antibody was made to the N-terminal peptide of human D6 (corresponding to amino acids 7–21 of SEQ ID NO:2). This antibody was used at a concentration of 15 μg/ml to stain THP-1 cells (a human monocytic cell line) as well as B-end cells (murine brain endothelial cell line). A cell line, K293, that was transfected with human D6, was used as a control for cell surface expression. Cells were first blocked with either human IgG or mouse IgG for 15 minutes. The antibody was then added to the cells which were on ice for 30 minutes. The cells were washed twice and a secondary antibody, goat anti-rabbit-FITC was added and incubated on ice for 30 minutes. The cells were washed twice and fixed with 1% formalin in PBS. The samples were read on a FACS Calibur.

This antibody recognizes D6 on both a human and mouse cell line.

Antibody Blocking Analysis

8–10 week old C57BL/6J and Balb/c mice are purchased from the Jackson Laboratory (Bar Harbor, Me.). The mouse model of lung inflammation consists of sensitization phase (OVA 0.1 mg/mouse intraperitoneally on day 0) (Sigma) and an induction of the response phase (2% OVA for 5 minutes intranasally on day 8 and 1% OVA for 20 minutes intranasally on days 15–21) as described in Gonzalo et al. (1996) *Immunity* 4:1–14. PBS is administered, intraperitoneally or intranasally, to mice as a negative control.

For the blocking experiments, mice receive 10 mg/mouse neutralizing polyclonal antibodies against human D6. These antibodies are administered intravenously and 30 minutes before OVA provocation on days 8–21. OVA-treated control mice are injected with the same amount of control antibody at the time points indicated during treatment. Rabbit immunoglobin fraction (Dako Corp., Santa Barbara, Calif.) is used as a control for the anti-human D6 antibody. Three hours after OVA administration on day 21, mice are sacrificed by carbon dioxide asphyxiation and analyzed.

Example 8
Competition Binding Assays for Human D6
Binding Assays with Agonists of Human D6

Several cell lines have been generated by stably transfecting the cells with the human D6 gene. The cell line K293 transfected with either human D6 (wild type), a mutated version of the same gene human D6 (Mut) or an antisense oligonucleotide of human D6 was used for competition binding assays. Natural agonists for human D6 are the ligands MCP-1 or MCP-5. These agonists work at the range of concentration from 1 ng/ml to 500 ng/ml (MCP-1: 0.115 nM–58 nM, MCP-5: 0.1 nM–50 nM) by functional assays. Both agonists bind the extracellular domain of the human D6 receptor and are commercially available from R&D systems.

Cells were washed once with binding buffer and plated at $10^5$ cells/well in 96-well plates with a constant amount (0.75 nM) of $^{125}$I-MCP-1. Displacement analysis was carried out using increasing concentrations of the unlabeled ligand MCP-5. Binding proceeded for 90 minutes at room temperature, then each well was washed three times with washing buffer. Scintillation fluid (50 μl/well) was added and CPM were counted.

These binding assays reveal that MCP-1 and MCP-5 bind human D6 receptor K293 transfectant (adherent cells) showed a clear competition binding curve when $^{125}$I-MCP-1 was used for competition of MCP-5.

Binding Competition Assays with Anti-sense Human D6 Oligonucleotides

In order to block human D6-induced signals, four different human D6 anti-sense oligonucleotides were designed and designated A, B, C and D. An anti-sense oligonucleotide control was also designed. When in vivo blocking experiments were performed, human D6 anti-sense oligonucleotides A and B show some blocking activity (see below).

Human D6 Anti-sense Oligonucleotide Sequences

Oligo A: 5'-TGGGCATGTCCTCGAGCTCT-3' (SEQ ID NO:26)

Oligo B: 5'-TGATCCACACCATGACAATG-3' (SEQ ID NO:27)

control: 5'-TGCGCCTGTCCACGTGCACA-3' (SEQ ID NO:28)

Blockage of MCP-5-induced Peritoneal Leukocyte Accumulation by Human D6 Anti-sense Olios Peritoneal recruitment assays were performed in vivo after intraperitoneal injection of 1 μg per mouse of purified mMCP-5 protein. Two hours after mMCP-5 injection, leukocytes recovered from peritoneal lavage were analyzed and enumerated. A human D6 anti-sense oligonucleotide A, B, C, D or control (200 μg per mouse) were administered intravenously at 12 hours, 4 hours and 1 hour before mMCP-5 injection.

The in vivo administration of human D6 anti-sense oligonucleotides A or B correlates with a decrease in MCP-5-induced peritoneal monocyte/lymphocyte accumulation.

Administration of Human D6 Anti-sense Oligonucleotides During Lung Allergic Inflammation Intranasal Administration of Human D6 Anti-sense Oligonucleotides Allergic inflammation was induced in C57Bl6 mice according to the protocol described by Gonzalo et al. (1996) *Immunity* 4:1–14, or Coyle et al. (1996). *J. Exp. Med.* 183:1303–1310. Briefly, each C57Bl6 mouse was immunized with 0.1 mg intraperitoneally of OVA on day 0. After eight days and again from days 15 to 19, each mouse was administered intranasally the following: 25 μl of 2 mg/ml OVA and 200 μg/25 μl PBS with human D6 anti-sense oligonucleotide A or B or the control anti-sense oligonucleotide. Since CCR2 binds MCP-1 and MCP-5, antibodies against this receptor were also administered 30 minutes before antigen challenge in a group of experimental mice. Three hours after the last OVA challenge on day 19, leukocytes recovered from BAL fluid were analyzed.

The in vivo administration of human D6 anti-sense oligonucleotides A or B during lung allergic inflammation correlates with a 50% decrease in eosinophilia and abrogation of monocyte/lymphocyte migration to the airways.

Example 9

Generation of cDNA Fragments of Murine D6 from Sorted Bone Marrow Cells

To more specifically examine the patterns of murine D6 expression within the hemopoietic system, the expression of murine D6 was investigated using amplified cDNA fragments generated from sorted populations of hemopoietic cells, including a line negative fraction containing primitive cells. The resulting lineage specific cDNA populations were used to determine expression of murine D6 in these populations.

Murine D6 cDNA Production

Bone marrow cells from the femurs of 20 mice were isolated into PBS containing 2% fetal calf serum (PBS/FCS). 5×10$^6$ cells were used directly for poly(A) mRNA preparation (see below). The remaining cells were diluted to 2.5×10$^7$ cells/ml, layered onto an equal volume of 1.077 g/ml Nycodenz solution (Nycomed, Oslo, Norway) and spun at 1,000×g for 30 minutes at 22° C. The low density cells at the interface were removed, spun for a second time through the density gradient, washed twice in PBS/FCS, and resuspended to 1×10$^6$ cells/ml in PBS/FCS. Different cell types were then sorted sequentially in the following order by addition of rat antibodies, Gr-1, B220, CD5/CD8, and Mac-1 (Pharmingen, San Diego, Calif., except Mac-1, Caltag, San Francisco, Calif.) followed by magnetic separation with sheep anti-rat M-450 beads (Dynal, Oslo, Norway), according to the manufacturers' instructions. After the four antibody positive cell fractions were purified, remaining unbound cells were designated lineage negative (lin–). Poly(A) mRNA was then isolated from the six cell populations (total bone marrow, Gr-1+, B220+, CD5/CD8+, Mac-1+, and lin–) using the Micro-Fast Track™ kit (Invitrogen) and cDNA prepared, according to the suppliers instructions, with the Copykit (Invitrogen), cDNA was digested with AluI, the enzyme was heat-inactivated and the cDNA fragments were phenol/chloroforn extracted and ethanol precipitated.

Linker Preparation

The following specific pairs of oligonucleotide linkers were used for each cDNA sample to minimize carry over contamination:

Bone Marrow

1: 5'-ACAGTCCCATGGTACAAGTTCAGCA-3' (SEQ ID NO:29)

2: 5'-GAACTTGTACCATGGGACTGT-3' (SEQ ID NO:30)

Granulocyte (Gr-1)

1: 5'-GAACTCGGATCCCATGTGAAGGTGT-3' (SEQ ID NO:31)

2: 5'-CTTCACATGGGATCCGAGTTC-3' (SEQ ID NO:32)

B-cells (B220)

1: 5'-AACCGTAGATCTGCTGCACACCAAC-3' (SEQ ID NO:33)

2: 5'-GTGTGCAGCAGATCTACGGTT-3' (SEQ ID NO:34)

T-cells (CD5/CD8)

1: 5'-TAGACCAAGCTTAGACTGACATCCT-3' (SEQ ID NO:35)

2: 5'-AGTTACACGTCTAGAATGGCT-3' (SEQ ID NO:36)

Lineage negative (lin–)

1: 5'-TAGTCCGAATTCAAGCAAGAGCACA-3' (SEQ ID NO:37)

2: 5'-CTCTTGCTTGAATTCGGACTA-3' (SEQ ID NO:38)

Each set of linker pairs (6 μg of each oligonucleotide, heat denatured at 90° C. for 2 minutes and cooled to 4° C.) were kinased in 1×polynucleotide kinase buffer (NBL Gene Science Ltd., Cramlington, UK) containing 1 mM dATP and 1 μl of [γ-$^{32}$P]dATP (Amersham) with 20 units of polynucleotide kinase (NBL) at 37° C. for 1 hour. The reaction was placed 70° C. for 5 minutes, allowed to cool over 2 hours to 22° C. to anneal the complementary linkers, and stored at –20° C.

Ligation of Linkers and PCR Amplification of cDNA Fragments

The duplexed, kinased linkers were ligated onto the corresponding cDNA according to Sambrook et al., in 1×ligase buffer (NBL) containing 1 mM hexamminecobalt chloride and 0.5 mM spermidine, at 16° C. for 20 hours. Linkers were separated from cDNA by adding glycerol to 20% and briefly electrophoresing each sample on a 2% low melting point agarose TAE gel. DNA separate from the unincorporated linkers (~100–1000 base pairs) was excised in a gel volume of approximately 0.5 ml. PCR was performed directly on 5 µl of this slice melted at 70° C. in a reaction containing 0.4 mM of each dNTP, 16 ng/µl of the cell type-specific B oligonucleotide (see above), and 7.5 units of AmpliTaq™. Reactions were incubated for 35 cycles at 94° C. for 1 minute, 52° C. for 1 minute, and 72° C. for 3 minutes.

Southern Blotting

Visually estimated equal quantities (approximately 5 µg) of the separate PCR products from each population of sorted cells were separated on a 1.2% agarose gel that was subsequently treated twice for 15 minutes each with 1.5. m NaCl, 0.5 m NaOH and then neutralized two times for 30 minutes each in 1.5 m NaCl, 0.5 m Tris (pH 7.5), 1 mM EDTA. DNA was transferred to Hybond N+, fixed prehybridized, hybridized, washed, and exposed as described for Northern blots. Filters were stripped in 0.1% SDS at 100° C. prior to reprobing. Full-length murine D6 cDNA was used as a probe for each of the chemokine receptors. Other probes used were murine T cell receptor Cβ cDNA and murine immunoglobulin H cDNA (provided by Dr. M. Stewart, University of Glasgow), murine lysozyme M (provided by Dr. M. Cross, CRC Paterson Institute, Manchester), v-fms (provided by Dr. A. Ford, LRF Chester Beatty Labs., London), murine CD34 cDNA (provided by Dr. G. May, LRF Chester Beatty Labs., London), and murine β-actin (provided by D. Jarmin, Beatson Institute, Glasgow).

The results of these experiments reveal expression of murine D6 in the T cell and monocyte/macrophage lineages. Murine D6 expression was also detected in the XS52 Langerhans cell line suggesting that the murine D6 receptor may be a normal component of the Langerhans/dendritic cell receptor population. In addition, murine D6 receptor expression was detectable in primitive lineage negative hematopoietic cells suggesting a role for the D6 gene in MIP-1α-induced stem cell inhibition. Murine D6 is easily detected showing strong enrichment in lin– cells relative to total bone marrow to levels similar to that seen with CD34.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid molecule comprising a nucleotide sequence which encodes a polypeptide comprising the amino acid sequence of SEQ ID NO:2, or a complement of said isolated nucleic acid molecule.

2. An isolated nucleic acid molecule comprising a nucleotide sequence which encodes a polypeptide comprising the amino acid sequence of SEQ ID NO:5, or a complement of said isolated nucleic acid molecule.

3. An isolated nucleic acid molecule comprising a nucleotide sequence encoding a polypeptide consisting of the amino acid sequence of SEQ ID NO:2 or 5, or a complement of said isolated nucleic acid molecule.

4. An isolated nucleic acid molecule comprising the nucleotide sequence of SEQ ID NO:1, or a complement of said isolated nucleic acid molecule.

5. An isolated nucleic acid molecule comprising the nucleotide sequence of SEQ ID NO:3, or a complement of said isolated nucleic acid molecule.

6. An isolated nucleic acid molecule comprising the nucleotide sequence of SEQ ID NO:4, or a complement of said isolated nucleic acid molecule.

7. An isolated nucleic acid molecule comprising a nucleotide sequence of SEQ ID NO:6, or a complement of said isolated nucleic acid molecule.

8. An isolated nucleic acid molecule consisting of the nucleotide sequence of SEQ ID NO:1, 3, 4, or 6, or a complement of said isolated nucleic acid molecule.

9. An isolated nucleic acid molecule comprising at least 500 nucleotides of the nucleotide sequence of SEQ ID NO:1, or a complement of said isolated nucleic acid molecule.

10. An isolated nucleic acid molecule comprising at least 500 nucleotides of the nucleotide sequence of SEQ ID NO:3, or a complement of said isolated nucleic acid molecule.

11. An isolated nucleic acid molecule comprising at least 500 nucleotides of the nucleotide sequence of SEQ ID NO:4, or a complement of said isolated nucleic acid molecule.

12. An isolated nucleic acid molecule comprising at least 500 nucleotides of the nucleotide sequence of SEQ ID NO:6, or a complement of said isolated nucleic acid molecule.

13. An isolated nucleic acid molecule consisting of at least 500 nucleotides of the nucleotide sequence of SEQ ID NO:1, or a complement of said isolated nucleic acid molecule.

14. An isolated nucleic acid molecule consisting of at least 500 nucleotides of the nucleotide sequence of SEQ ID NO:3, or a complement of said isolated nucleic acid molecule.

15. An isolated nucleic acid molecule consisting of at least 500 nucleotides of the nucleotide sequence of SEQ ID NO:4, or a complement of said isolated nucleic acid molecule.

16. An isolated nucleic acid molecule consisting of at least 500 nucleotides of the nucleotide sequence of SEQ ID NO:6, or a complement of said isolated nucleic acid molecule.

17. A vector comprising the nucleic acid molecule of any one of claims 1, 2, 3, 4, 5, 6, 7, 8, 9, 10, 11, 12, 13, 14, 15, or 16.

18. The vector of claim 17, which is a recombinant expression vector.

19. An isolated host cell transfected with the nucleic acid molecule of any one of claims 1, 2, 3, 4, 5, 6, 7, 8, 9, 10, 11, 12, 13, 14, 15, or 16.

20. The isolated host cell of claim 19 which is a mammalian host cell.

21. A method for expressing a polypeptide comprising culturing the host cell of claim 19 under conditions in which a polypeptide encoded by the nucleic acid molecule is expressed.

22. The method of claim 21, further comprising isolating the polypeptide from the host cell.

23. A method for producing a polypeptide comprising culturing the host cell of claim 19 under conditions in which the nucleic acid molecule is expressed and isolating the polypeptide from the host cell.

24. An isolated nucleic acid molecule comprising the nucleic acid molecule of any one of claims 1, 2, 3, 4, 5, 6, 7, 8, 9, 10, 11, 12, 13, 14, 15 or 16 and a nucleic acid sequence encoding a heterologous peptide.

25. A kit comprising a nucleic acid molecule of any one of claims 1, 2, 3, 4, 5, 6, 7, 8, 9, 10, 11, 12, 13, 14, 15, or 16 and instructions for use.

* * * * *

UNITED STATES PATENT AND TRADEMARK OFFICE
CERTIFICATE OF CORRECTION

PATENT NO. : 6,287,805 B1
DATED : September 11, 2001
INVENTOR(S) : Gerard J. Graham et al.

It is certified that error appears in the above-identified patent and that said Letters Patent is hereby corrected as shown below:

<u>Title page,</u>
Item [75], please delete "Jose-Angel Gonzalo, Cambridge; Jose-Carlos Gutierrez-Ramos, Swampscott, both of MA (US)."

Signed and Sealed this

Thirtieth Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,287,805 B1
DATED : September 11, 2001
INVENTOR(S) : Gerard J. Graham et al.

It is certified that error appears in the above-identified patent and that said Letters Patent is hereby corrected as shown below:

<u>Title page,</u>
Item [73], please delete "Millennium Pharmaceuticals, Inc." and insert
-- CRC Technology Limited. --

Signed and Sealed this

Twentieth Day of May, 2003

JAMES E. ROGAN
*Director of the United States Patent and Trademark Office*